(12) United States Patent
Clarke et al.

(10) Patent No.: US 12,727,991 B2
(45) Date of Patent: Sep. 8, 2026

(54) OCULAR IMPLANT SUPPORT DEVICES AND METHODS OF USE

(71) Applicant: Long Bridge Medical, Inc., South San Francisco, CA (US)

(72) Inventors: Matthew Clarke, South San Francisco, CA (US); Ayman Naseri, South San Francisco, CA (US); Matthew Tice, South San Francisco, CA (US); Jacob Osecheck, South San Francisco, CA (US)

(73) Assignee: Long Bridge Medical, Inc., South San Francisco, CA (US)

( * ) Notice: Subject to any disclaimer, the term of this patent is extended or adjusted under 35 U.S.C. 154(b) by 414 days.

(21) Appl. No.: 18/511,340

(22) Filed: Nov. 16, 2023

(65) Prior Publication Data

US 2024/0180691 A1 Jun. 6, 2024

Related U.S. Application Data

(60) Provisional application No. 63/512,857, filed on Jul. 10, 2023, provisional application No. 63/426,152, filed on Nov. 17, 2022.

(51) Int. Cl.
*A61F 2/16* (2006.01)

(52) U.S. Cl.
CPC ...... *A61F 2/1651* (2015.04); *A61F 2002/169* (2015.04); *A61F 2002/16902* (2015.04);
(Continued)

(58) Field of Classification Search
CPC .............. A61F 2/1651; A61F 2002/169; A61F 2220/0033; A61F 2230/0006; A61F 2250/0063
See application file for complete search history.

(56) References Cited

U.S. PATENT DOCUMENTS

| | | | |
|---|---|---|---|
| 3,673,616 | A | 7/1972 | Fedorov et al. |
| 3,866,249 | A | 2/1975 | Flom |

(Continued)

FOREIGN PATENT DOCUMENTS

| | | | |
|---|---|---|---|
| CA | 2928918 | A1 | 3/2017 |
| CN | 2328346 | Y | 7/1999 |

(Continued)

OTHER PUBLICATIONS

Alwitry, Amir (n.d.) IC-8 pinhole IOL. 1 page. https://amaralwitry.com/about/our-procedures/premium-lenses-refractive-procedures/ic-8-pinhole-iol.

(Continued)

*Primary Examiner* — Richard G Louis
(74) *Attorney, Agent, or Firm* — Mintz Levin Cohn Ferris Glovsky and Popeo, P.C.

(57) ABSTRACT

An implantable scleral suspension device for use with an intraocular lens, an artificial iris, or an implantable miniature telescope (IMT) in an eye. The device includes an elastic support structure having a central aperture extending through the support structure between an anterior surface of the support structure and a posterior surface of the support structure. The central aperture is defined by an inner perimeter surface. A plurality of fixation arms extend outward from the outer perimeter surface, each arm configured for sutureless scleral fixation and to be placed under tension to locate and stabilize the device within the eye. A thickness of the support structure along the inner perimeter surface defining the central aperture is greater than a thickness of the support structure near the outer perimeter surface. Related devices, systems, and methods are also provided.

21 Claims, 20 Drawing Sheets

(52) U.S. Cl.
CPC ................ *A61F 2220/0033* (2013.01); *A61F 2230/0006* (2013.01); *A61F 2250/0063* (2013.01)

(56) References Cited

U.S. PATENT DOCUMENTS 3,922,728 A 12/1975 Krasnov
3,925,825 A 12/1975 Richards et al.
3,986,214 A 10/1976 Krasnov
4,014,049 A 3/1977 Richards et al.
4,073,014 A 2/1978 Poler
4,110,848 A 9/1978 Jensen
4,118,808 A 10/1978 Poler
4,168,547 A 9/1979 Konstantinov et al.
4,190,049 A 2/1980 Hager et al.
4,215,440 A 8/1980 Worst
4,242,762 A 1/1981 Tennant
4,254,511 A 3/1981 Chase et al.
4,262,370 A 4/1981 Hartstein
4,298,996 A 11/1981 Barnet
4,429,421 A 2/1984 Levy
4,437,194 A 3/1984 Hahs
4,576,607 A 3/1986 Kelman
4,585,457 A 4/1986 Kalb
4,617,023 A 10/1986 Peyman
4,629,460 A 12/1986 Dyer
4,718,905 A 1/1988 Freeman
4,737,322 A 4/1988 Bruns et al.
4,790,847 A 12/1988 Woods
4,878,910 A 11/1989 Koziol et al.
4,932,971 A 6/1990 Kelman
5,026,396 A 6/1991 Darin
5,152,787 A 10/1992 Hamblen
5,222,981 A 6/1993 Werblin
5,258,025 A 11/1993 Fedorov et al.
5,275,624 A 1/1994 Hara et al.
5,326,347 A 7/1994 Cumming
5,336,262 A 8/1994 Chu
5,466,233 A 11/1995 Weiner et al.
5,476,512 A 12/1995 Sarfarazi
5,507,805 A 4/1996 Koeniger
5,628,795 A 5/1997 Langerman
5,628,798 A 5/1997 Eggleston et al.
5,697,973 A 12/1997 Peyman et al.
5,752,960 A 5/1998 Nallakrishnan
5,776,191 A 7/1998 Mazzocco
5,843,184 A 12/1998 Cionni
6,027,531 A 2/2000 Tassignon
6,066,171 A 5/2000 Lipshitz et al.
6,113,633 A 9/2000 Portney
6,136,026 A 10/2000 Israel
6,152,959 A 11/2000 Portney
6,228,115 B1 5/2001 Hoffmann et al.
6,261,321 B1 7/2001 Kellan
6,264,693 B1 7/2001 Ross
6,299,641 B1 10/2001 Woods
6,342,058 B1 1/2002 Portney
6,398,809 B1 6/2002 Hoffmann et al.
6,409,763 B1 6/2002 Brady
6,443,985 B1 9/2002 Woods
6,488,708 B2 12/2002 Sarfarazi
6,551,354 B1 4/2003 Ghazizadeh et al.
6,596,026 B1 7/2003 Gross et al.
6,616,691 B1 9/2003 Tran
6,616,692 B1 9/2003 Glick et al.
6,660,036 B2 12/2003 Cumming
6,685,741 B2 2/2004 Landreville et al.
6,767,363 B1 7/2004 Bandhauer et al.
6,797,004 B1 9/2004 Brady et al.
6,881,225 B2 4/2005 Okada
6,921,415 B2 7/2005 Callahan et al.
6,972,033 B2 12/2005 McNicholas
7,125,422 B2 10/2006 Woods et al.
7,223,288 B2 5/2007 Zhang et al.
7,300,464 B2 11/2007 Tran
7,311,194 B2 12/2007 Jin et al.
7,354,451 B2 4/2008 Koch
7,416,561 B2 8/2008 Worst et al.
7,462,194 B1 12/2008 Blake
7,569,048 B2 8/2009 Brown
7,597,678 B2 10/2009 Brown
7,662,179 B2 2/2010 Sarfarazi
7,763,069 B2 7/2010 Brady et al.
7,794,498 B2 9/2010 Pinchuk
7,806,929 B2 10/2010 Brown
7,806,930 B2 10/2010 Brown
7,875,270 B2 1/2011 Zhang
7,931,686 B2 4/2011 Vaudant et al.
8,012,204 B2 9/2011 Weinschenk, III et al.
8,109,998 B2 2/2012 Cumming
8,128,693 B2 3/2012 Tran et al.
8,162,927 B2 4/2012 Peyman
8,216,305 B2 7/2012 Salvati et al.
8,273,123 B2 9/2012 Ben Nun
8,377,125 B2 2/2013 Kellan
8,551,164 B2 10/2013 Willis et al.
8,585,758 B2 11/2013 Woods
8,663,235 B2 3/2014 Tassignon
8,764,823 B2 7/2014 Cumming
8,778,022 B2 7/2014 Blum et al.
8,821,166 B2 9/2014 Akura et al.
8,852,275 B2 10/2014 Park
8,888,845 B2 11/2014 Vaquero et al.
8,900,300 B1 12/2014 Wortz
8,920,495 B2 12/2014 Mirlay
8,932,351 B2 1/2015 Dell
8,945,215 B2 2/2015 Basinger
8,956,408 B2 2/2015 Smiley et al.
9,034,035 B2 5/2015 Betser et al.
9,039,762 B2 5/2015 Hong et al.
9,072,600 B2 7/2015 Tran
9,078,744 B2 7/2015 Van Noy
9,084,673 B2 7/2015 Dell
9,095,424 B2 8/2015 Kahook et al.
9,125,736 B2 9/2015 Kahook et al.
9,198,752 B2 12/2015 Woods
9,289,287 B2 3/2016 Kahook et al.
9,326,845 B2 5/2016 Ichikawa et al.
9,333,072 B2 5/2016 Ichikawa
9,339,375 B2 5/2016 Lee et al.
9,358,103 B1 6/2016 Wortz et al.
9,364,316 B1 6/2016 Kahook et al.
9,364,318 B2 6/2016 Beer
9,387,069 B2 7/2016 Kahook et al.
9,398,949 B2 7/2016 Werblin
9,421,088 B1 8/2016 Kahook et al.
9,439,754 B2 9/2016 Wortz
9,445,891 B2 9/2016 Ichikawa
9,445,892 B2 9/2016 Brown
9,468,523 B2 10/2016 Dell
9,498,325 B2 11/2016 Salvati et al.
9,504,558 B2 11/2016 Wortz et al.
9,517,127 B2 12/2016 Wortz et al.
9,522,060 B2 12/2016 Wortz et al.
9,622,857 B2 4/2017 Coroneo
9,629,711 B2 4/2017 Cumming
9,681,945 B2 6/2017 Shahinpoor et al.
9,681,946 B2 6/2017 Kahook et al.
9,713,526 B2 7/2017 Rombach
9,744,027 B2 8/2017 Jansen
9,757,227 B2 9/2017 Kushlin et al.
9,763,771 B1 9/2017 Wortz et al.
9,877,825 B2 1/2018 Kahook et al.
9,925,037 B2 3/2018 Wortz et al.
9,925,040 B2 3/2018 Kahook et al.
9,962,256 B2 5/2018 McCafferty
10,004,591 B2 6/2018 Ichikawa
10,010,405 B2 7/2018 Hayes
10,080,648 B2 9/2018 Kahook et al.
10,085,886 B2 10/2018 Schuele et al.
10,201,415 B2 2/2019 Aharoni et al.
10,271,944 B2 4/2019 Ichikawa et al.
10,271,945 B2 4/2019 Wortz et al.
10,286,107 B2 5/2019 Kahook et al.

(56) References Cited

U.S. PATENT DOCUMENTS 10,299,910 B2 5/2019 Cady
10,383,721 B2 8/2019 Marcos Celestino et al.
10,433,950 B2 10/2019 Shadduck
10,449,036 B2 10/2019 Christie et al.
10,470,873 B2 11/2019 Ichikawa et al.
10,524,900 B2 1/2020 Beer
10,548,713 B2 2/2020 Aharoni
10,575,943 B2 3/2020 Ingram
10,603,162 B2 3/2020 Wortz et al.
10,765,509 B2 9/2020 Olson et al.
10,799,340 B2 10/2020 Collins et al.
10,973,624 B1 4/2021 Clarke et al.
11,364,110 B2 6/2022 Webb
11,382,736 B2 7/2022 Zacher et al.
11,759,311 B2 9/2023 Whitsett
11,833,029 B2 12/2023 Dudee
2002/0087210 A1 7/2002 Stenger et al.
2002/0103535 A1 8/2002 Portney
2002/0161433 A1 10/2002 Baikoff et al.
2003/0055499 A1 3/2003 Nguyen et al.
2003/0158560 A1 8/2003 Portney
2003/0158599 A1 8/2003 Brady et al.
2003/0220652 A1 11/2003 Israel
2004/0042073 A1 3/2004 Pynson
2004/0064182 A1 4/2004 Kelman
2004/0148022 A1 7/2004 Eggleston
2004/0236422 A1 11/2004 Zhang et al.
2004/0249455 A1 12/2004 Tran
2005/0021138 A1 1/2005 Woods
2005/0021140 A1 1/2005 Liao
2005/0085907 A1 4/2005 Hanna
2005/0177229 A1 8/2005 Boxer Wachler
2006/0047340 A1 3/2006 Brown
2006/0235515 A1 10/2006 Chassain
2007/0027541 A1 2/2007 Aharoni et al.
2007/0032868 A1 2/2007 Woods
2007/0123982 A1 5/2007 Yablonski et al.
2007/0162115 A1 7/2007 Hermeking
2007/0260308 A1 11/2007 Tran
2008/0086208 A1 4/2008 Nordan
2008/0154364 A1 6/2008 Richardson et al.
2009/0171458 A1 7/2009 Kellan et al.
2009/0198247 A1 8/2009 Ben Nun
2009/0204209 A1 8/2009 Tran
2010/0030331 A1 2/2010 Zhang et al.
2010/0057095 A1 3/2010 Khuray et al.
2010/0094415 A1 4/2010 Bumbalough
2010/0121444 A1 5/2010 Ben Nun
2010/0131059 A1 5/2010 Callahan et al.
2010/0152848 A1 6/2010 Williamson et al.
2010/0262234 A1 10/2010 Tran et al.
2011/0071628 A1 3/2011 Gross et al.
2011/0295368 A1 12/2011 Betser
2011/0313521 A1 12/2011 Angelopoulos
2011/0313522 A1 12/2011 Hayes
2011/0313523 A1 12/2011 Hayes
2012/0290086 A1 11/2012 Malyugin et al.
2012/0303119 A1 11/2012 Callahan et al.
2012/0330415 A1 12/2012 Callahan et al.
2013/0116781 A1 5/2013 Ben Nun
2013/0190868 A1 7/2013 Kahook et al.
2014/0094908 A1 4/2014 Zaldivar et al.
2014/0121768 A1 5/2014 Simpson
2014/0316520 A1 10/2014 Barsam et al.
2014/0330375 A1 11/2014 McCafferty
2014/0371851 A1 12/2014 Aharoni
2014/0371852 A1 12/2014 Aharoni et al.
2015/0025627 A1 1/2015 Christie et al.
2015/0127102 A1 5/2015 Wortz
2015/0202040 A1* 7/2015 McCafferty .............. A61F 2/16
623/6.43
2015/0265398 A1 9/2015 Hartkens et al.
2015/0305857 A1 10/2015 Ichikawa
2015/0366656 A1 12/2015 Wortz et al.
2015/0366659 A1 12/2015 Wortz et al.
2016/0000558 A1 1/2016 Honigsbaum
2016/0128828 A1 5/2016 Dalvi
2016/0157995 A1 6/2016 Beer
2016/0184089 A1 6/2016 Dudee et al.
2016/0256260 A1 9/2016 Wortz et al.
2016/0256262 A1 9/2016 Wortz et al.
2016/0256267 A1 9/2016 Wortz et al.
2016/0256315 A1 9/2016 Wortz et al.
2016/0331520 A1 11/2016 Beer
2016/0338825 A1 11/2016 Wortz et al.
2016/0361156 A1 12/2016 Brown
2017/0020662 A1 1/2017 Shadduck
2017/0049560 A1 2/2017 Cherne
2017/0258575 A1 9/2017 Wortz et al.
2017/0319332 A1 11/2017 Kahook et al.
2017/0348095 A1 12/2017 Wortz et al.
2018/0014928 A1 1/2018 Kahook et al.
2018/0110613 A1 4/2018 Wortz et al.
2018/0263757 A1 9/2018 Wanders
2018/0271642 A1 9/2018 Wortz et al.
2018/0338825 A1 11/2018 Aharoni
2019/0015197 A1 1/2019 Wortz et al.
2019/0076236 A1 3/2019 Scharioth et al.
2019/0076239 A1 3/2019 Wortz et al.
2019/0083235 A1 3/2019 Wortz
2019/0091009 A1 3/2019 Collins et al.
2019/0125944 A1 5/2019 Wiley
2019/0133754 A1 5/2019 Dalvi
2019/0151079 A1 5/2019 Zaldivar
2019/0223998 A1 7/2019 de Juan, Jr. et al.
2019/0254809 A1 8/2019 Dworschak et al.
2019/0269499 A1 9/2019 Ellis
2019/0269500 A1 9/2019 de Juan, Jr. et al.
2019/0343621 A1 11/2019 Wortz et al.
2019/0380828 A1 12/2019 Wortz
2020/0000575 A1 1/2020 Kojima
2020/0022840 A1 1/2020 Kahook et al.
2020/0121446 A1 4/2020 Cady
2020/0253721 A1 8/2020 Cuevas et al.
2020/0276011 A1 9/2020 Akura
2020/0323626 A1 10/2020 Akinay et al.
2021/0137674 A1* 5/2021 Webb ...................... A61L 27/50
2021/0315687 A1 10/2021 Brodie et al.
2021/0338416 A1 11/2021 Clarke et al.
2021/0338417 A1 11/2021 Clarke et al.
2021/0353406 A1 11/2021 Brodie et al.
2022/0000605 A1 1/2022 Clarke et al.
2022/0079744 A1 3/2022 Arrieta
2022/0211487 A1 7/2022 Clarke et al.
2022/0362010 A1 11/2022 Akura
2023/0031555 A1 2/2023 Wortz et al.
2023/0127407 A1 4/2023 So
2024/0058115 A1 2/2024 Kim et al.

FOREIGN PATENT DOCUMENTS

CN 101031257 A 9/2007
CN 101325925 A 12/2008
CN 102090942 A 6/2011
CN 102090946 A 6/2011
CN 102970942 A 3/2013
CN 204698755 U 10/2015
CN 110811924 A 2/2020
DE 20 2016 105 208 U1 11/2016
DE 10 2019 115 408 B3 9/2020
EP 0 106 488 A1 4/1984
EP 0 346 245 A1 12/1989
EP 0 089 335 B2 3/1993
EP 0 931 521 A1 7/1999
EP 1037572 A1 9/2000
EP 1 138 282 A1 10/2001
EP 1 341 485 B1 11/2006
EP 2422746 A1 2/2012
EP 3 061 420 A1 8/2016
EP 3 158 974 A1 4/2017
EP 2 117 465 B1 7/2017
EP 3 171 821 B1 3/2020
EP 3700466 A1 9/2020
FR 2997624 A1 5/2014

(56) References Cited

FOREIGN PATENT DOCUMENTS

| | | | |
|---|---|---|---|
| FR | 3 033 694 | A1 | 9/2016 |
| GB | 124500 | A | 4/1919 |
| IT | 102014902224032 | A1 | 7/2015 |
| JP | 2006-525824 | A | 11/2006 |
| JP | 4892156 | B2 | 3/2012 |
| JP | 2013123616 | A | 6/2013 |
| JP | 5383782 | B2 | 1/2014 |
| JP | 2014090772 | A | 5/2014 |
| JP | 2015-223341 | A | 12/2015 |
| JP | 2019-063534 | A | 4/2019 |
| KR | 20030051903 | A | 6/2003 |
| KR | 10-2011-0075018 | A | 7/2011 |
| KR | 10-1555298 | B1 | 9/2015 |
| RU | 2132667 | C1 | 7/1999 |
| RU | 86462 | U1 | 9/2009 |
| RU | 2367380 | C2 | 9/2009 |
| RU | 2440076 | C1 | 1/2012 |
| TW | 201630576 | A | 9/2016 |
| WO | WO-99/56670 | A1 | 11/1999 |
| WO | WO-00/30566 | A1 | 6/2000 |
| WO | WO-2006/103674 | A2 | 10/2006 |
| WO | WO-2007/005893 | A2 | 1/2007 |
| WO | WO-2008/077795 | A2 | 7/2008 |
| WO | WO-2008/108525 | A1 | 9/2008 |
| WO | WO-2010/091420 | A1 | 8/2010 |
| WO | WO-2011/101310 | A1 | 8/2011 |
| WO | WO-2013/112589 | A1 | 8/2013 |
| WO | WO-2014/197170 | A1 | 12/2014 |
| WO | WO-2015/026226 | A1 | 2/2015 |
| WO | WO-2016/071755 | A1 | 5/2016 |
| WO | WO-2016/159910 | A1 | 10/2016 |
| WO | WO-2016/182520 | A1 | 11/2016 |
| WO | WO-2017/212352 | A1 | 12/2017 |
| WO | WO-2019/050925 | A1 | 3/2019 |
| WO | WO-2019/094768 | A1 | 5/2019 |
| WO | WO-2019/097099 | A1 | 5/2019 |
| WO | WO-2019/106011 | A1 | 6/2019 |
| WO | WO-2019/208746 | A1 | 10/2019 |
| WO | WO-2019/235912 | A1 | 12/2019 |
| WO | WO-2020/086312 | A1 | 4/2020 |
| WO | WO-2020/086631 | A1 | 4/2020 |
| WO | WO-2020/086312 | A8 | 7/2020 |
| WO | PCT/US2023/79993 | | 11/2023 |

OTHER PUBLICATIONS

Can, E. (2018). "Flapless and sutureless intrascleral fixation of posterior chamber intraocular lens for correction of aphakia." Journal of Cataract and Refractive Surgery, 44(8), 929-931.

Entokey. (Nov. 21, 2017). Intraocular Lens Implantation in the Capsular Bag and Posterior Capsulotomy Techniques. Retrieved Sep. 16, 2024, from https://entokey.com/intraocular-lens-implantation-in-the-capsular-bag-and-posterior-capsulotomy-techniques/ 4 pages.

Gabor, S.G. et al. (2007). "Sutureless intrascleral posterior chamber intraocular lens fixation." Journal of Cataract and Refractive Surgery, 33(11), 1851-1854.

Hu, Z. X. et al. (2018). "Sutureless Intrascleral Haptic-Hook Lens Implantation Using 25-Gauge Trocars." Journal of Ophthalmology, 2018, 9250425. 5 pages. A27.

Omega Ophthalmics. (n.d.) The Gemini Refractive Capsule TM Revolutionary, Not Evolutionary. 1 page. https://www.omegaophthalmics.com/video/.

Schaaf, Tracy. (Oct. 23, 2018). 'In MedTech History'—Ophthalmic Implants—Part 2. MyStrategist. 3 pages. https://www.mystrategist.com/blog/article/ophthalmic-part-2.

U.S. Appl. No. 17/190,169, filed Mar. 2, 2021, US 20210338417.

U.S. Appl. No. 17/284,561, filed Apr. 12, 2021, US20210353406.

U.S. Appl. No. 17/284,578, filed Apr. 12, 2021, US 20210315687.

U.S. Appl. No. 17/396,048, filed Aug. 6, 2021, US 20220000605.

U.S. Appl. No. 17/576,573, filed Jan. 14, 2022, US 20220211487.

U.S. Appl. No. 18/485,214, filed Oct. 11, 2023, US 20240033072.

U.S. Appl. No. 18/485,218, filed Oct. 11, 2023, US 20240033073.

U.S. Appl. No. 18/369,693, filed Sep. 18, 2023, US 20240074846.

U.S. Appl. No. 18/369,694, filed Sep. 18, 2023, US 20240074847.

U.S. Appl. No. 18/615,908, filed Mar. 25, 2024, US 20240225817.

Carlevale Lens (Carlo Carlevale) by Soleko, "Scleral Suturefree IOL—Product Description." Alyko Medical, www.alykomedical.com/en-GB/products/implants/scleral-sutureless-iol-34097888. Accessed Oct. 29, 2020. 1 page.

Carlevale, C., et al. (Nov. 15, 2018), "New IOL dedicated for scleral fixation," Ocular Surgery News. Web. Nov. 2, 2020. 4 pages. https://www.healio.com/news/ophthalmology/20181113/new-iol-dedicated-for-scleral-fixation?M_BT=3592487855654.

Hao, Y. et al. (2001). "Intracapsular IOL implantation of cataract with subluxation of lens." Journal of Ocular Trauma and Occupational Eye Diseases (with Ophthalmology Surgery), Issue 05, Sep. 30, 2001. 2 pages. [English abstract translation—p. 2].

* cited by examiner 2100
2104
2105
2107
2108
2109
2112
2115
2117
2120a
2120b
2120c
2125
2126
2127
2130
Tp
Ts
$W_i$
$W_e$
$D_I$
$L_i$
$L_e$
$D_d$
$D_a$
B
C

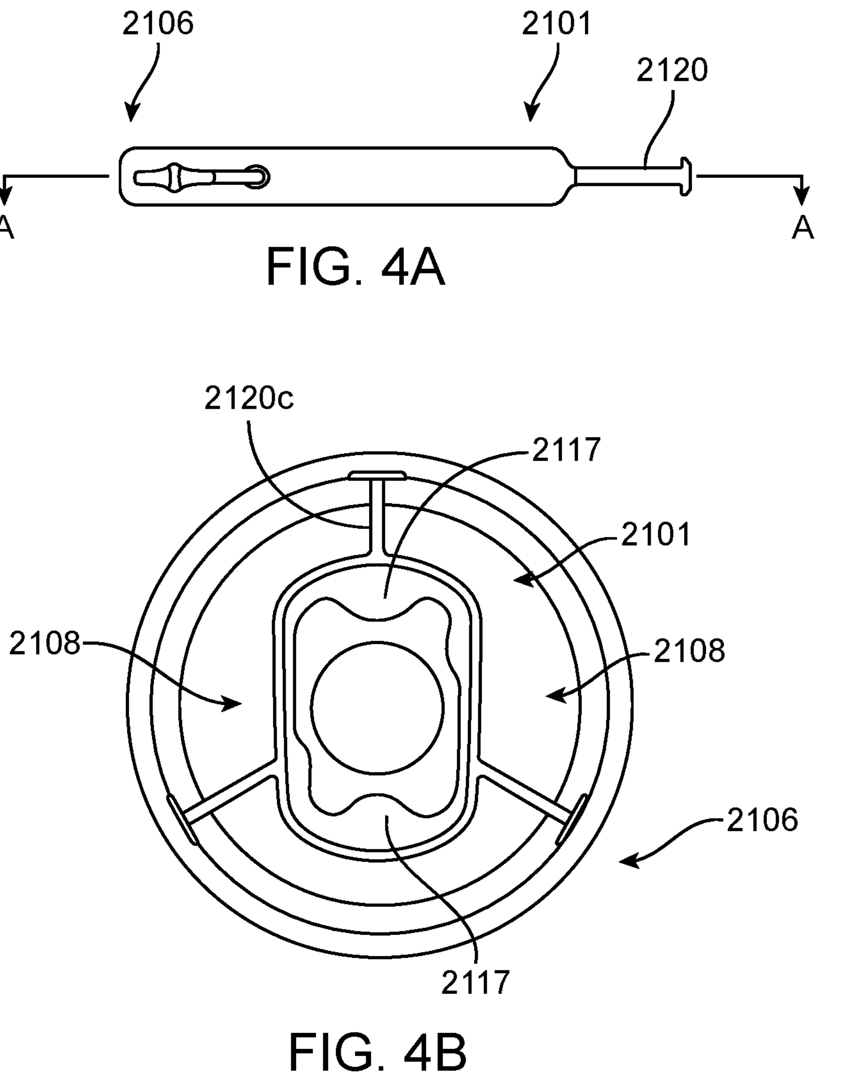
FIG. 4A
FIG. 4B
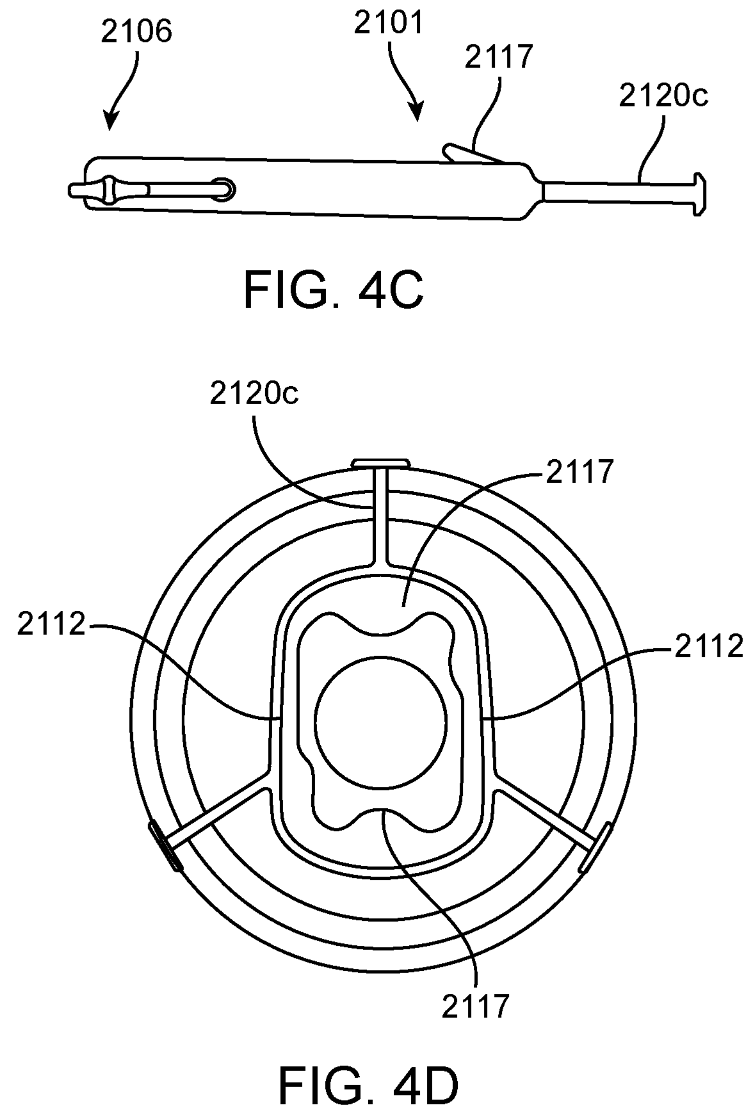
FIG. 4C
FIG. 4D 1310
1320
1324
1324
2100
2125
2125
2120
2120
1322
1322

OCULAR IMPLANT SUPPORT DEVICES AND METHODS OF USE

CROSS-REFERENCE TO RELATED APPLICATIONS

This application claims the benefit of priority to U.S. Provisional Application Ser. No. 63/426,152, filed Nov. 17, 2022; and 63/512,857, filed Jul. 10, 2023. The entire contents of these applications are incorporated by reference in their entireties.

BACKGROUND

The present disclosure relates generally to the field of ophthalmics, more particularly to delivery devices for implantation of ophthalmic devices for supporting and positioning optical implants, such as optical elements including intraocular lenses (IOLs), miniature telescopes, magnifiers, and camera elements, as well as other devices such as sensors in the eye.

Implantation of optical elements, such as IOLs, miniature telescopes, and others, requires support within the eye to hold them in the correct position. Often, this is achieved through the native capsular bag suspended by the zonules (fine, thread-like structures). However, these support structures can be compromised either due to intrinsic factors such as pseudoexfoliation, Marfan, or Weill-Marchesani syndromes, or extrinsic factors such as trauma. Additionally, lens support can be compromised iatrogenically either during the time of surgery (either anterior or posterior segment surgery) or as a late complication of previous surgery, for example by capsular phimosis.

The management of secondary IOL placement in the absence of sufficient capsular or zonular support continues to evolve. Currently, the only FDA approved solution is placement of an anterior chamber IOL (ACIOL). The ACIOL is a larger lens with the ability to sit anterior to the iris, however over time these lenses can cause Uveitis-Glaucoma-Hyphema (UGH) syndrome as well as endothelial cell loss and corneal decompensation, and as a result are contraindicated in many patients. Modified capsule tension rings (Cionni or Ahmed) can be used off-label to provide sutured scleral support to a partially weakened capsule. However, in cases of substantial capsule or zonular compromise the lens must be secured without use of these native supporting structures. Other off-label techniques can be employed, such as iris suturing IOL, but this is technically difficult and can lead to iris pigment loss causing glaucoma. Lastly, scleral suturing IOLs with islets is technically complex, risks rotation, and the durability of the sutures is unknown; there are reported cases of breakage and lens subluxation. Additionally, all of these techniques force the surgeon to use an alternative lens type, instead of their preferred lens for the patient. Lastly, the decision of timing is critical, as frequently lens calculations are inadequate during the initial vitrectomy/lensectomy yet there is the desire to not subject the patient to additional posterior segment surgery, so non-ideal lenses are frequently implanted.

Other intraocular devices are difficult to implant in a patient where capsular bag support is limited or lacking entirely, particularly where such devices are heavy in relation to the surrounding anatomy. For example, some patients who have lost central vision due to age-related macular degeneration may benefit from some restoration of their visual field by placement of an implantable miniature telescope (IMT). IMTs can be substantially heavier than a conventional intraocular lens and, like, IOLs are impaired by tilt or inadvertent movement of the device within the eye. Thus, fixation and stabilization of the heavier device is particularly problematic.

SUMMARY

In an aspect, described is an implantable device for supporting an implantable miniature telescope in an eye. The device includes a support structure including an outer perimeter surface of an outer perimeter wall having a non-circular shape, wherein the outer perimeter wall comprises two opposed side wall portions and two opposed end wall portions, each of the opposed end wall portions integrally coupled to each of the opposed side wall portions at a rounded corner to form the outer perimeter wall having the non-circular shape. A central aperture extends through the support structure between an anterior surface of the support structure and a posterior surface of the support structure. A thickness of the support structure defining the central aperture is greater than a thickness of the support structure near the outer perimeter surface. The device includes a plurality of fixation arms configured to be placed under tension to locate and stabilize the device within the eye. The thickness of the support structure defining the central aperture can be about 200-2000 microns thick. The thickness of the support structure near the outer perimeter surface can be less than about 200 microns. The central aperture can be sized to receive a carrier of a miniature telescope at least partially therethrough so as to mate the miniature telescope with the support structure.

In an interrelated aspect, provided is a system for implantation in an eye including a miniature telescope having an optically clear, outer carrier and an optical element located within the optically clear carrier; and a scleral suspension device configured to mate with the miniature telescope. The scleral suspension device includes a support structure having an outer perimeter wall and a central aperture extending through the support structure between an anterior surface of the support structure and a posterior surface of the support structure; and a plurality of fixation arms configured to be placed under tension to locate and stabilize the device within the eye. The carrier of the miniature telescope has an outer diameter configured to be inserted at least in part through the central aperture of the support structure to mate the carrier with the scleral suspension device so as to align the optical element of the miniature telescope for focusing on the retina of the eye.

The carrier can mate with the central aperture by a snap-fit. An external surface of the carrier can incorporate a posterior mating feature and an anterior stop. The posterior mating feature can be configured to allow the carrier to mate with the support structure by insertion through the central aperture in an anterior-to-posterior direction and configured to impair withdrawal of the carrier from the central aperture in a posterior-to-anterior direction following mating. The posterior mating feature can have a ramped posterior-facing surface such that an outer diameter of the posterior mating feature gradually increases from a posterior-most end towards an anterior-most end. The outer diameter of the posterior mating feature at the posterior-most end can be less than an inner diameter of the central aperture and the outer diameter of the posterior mating feature at the anterior-most end can be greater than the inner diameter of the central aperture. The posterior mating feature can be fully annular and surround a full circumferences of a posterior end region of the outer carrier. The posterior mating feature can be formed by a plurality of distinct material feature located at multiple points around a circumference of a posterior end region of the outer carrier. The anterior stop can be shaped and sized to prevent insertion of the anterior stop through the central aperture from an anterior-to-posterior direction or from a posterior-to-anterior direction.

In an interrelated aspect, provided is an implantable scleral suspension device for use with an implantable miniature telescope (IMT) in an eye including an elastic support structure. The support structure has an outer perimeter wall having an outer perimeter surface extending between an anterior surface of the support structure and a posterior surface of the support structure; and a central aperture extending through the support structure between the anterior surface of the support structure and the posterior surface of the support structure. The central aperture is defined by an inner perimeter surface of the support structure. A plurality of fixation arms extend outward from the outer perimeter surface of the support structure, each arm of the plurality of fixation arms is configured for sutureless scleral fixation and to be placed under tension to locate and stabilize the device within the eye. A thickness of the support structure along the inner perimeter surface defining the central aperture is greater than a thickness of the support structure near the outer perimeter surface.

The thickness of the support structure along the inner perimeter surface defining the central aperture can be about 200-2000 microns thick. The thickness of the support structure near the outer perimeter surface can be less than about 200 microns. The thickness of the support structure defining the central aperture can prevent tilt of the IMT supported by the scleral suspension device. The central aperture can be sized to receive a carrier of an IMT at least partially therethrough so as to mate the IMT with the support structure. The central aperture can have a diameter that is about 2 mm to about 6 mm.

The device can further include at least one awning positioned over the anterior surface of the support structure. The at least one awning forms at least one recess anterior to the anterior surface of the support structure. The at least one awning positioned over the anterior surface of the support structure can define an anterior opening of the device. The at least one recess can be adapted to receive a portion of the IMT. An anterior surface of the IMT can project anterior relative to the awning of the device and a posterior surface of the IMT can remain within the recess of the device. An anterior surface of the IMT can project anterior relative to the awning of the device and a posterior surface of the IMT can project posterior to the device.

The device can be part of a system that further includes the IMT. The IMT and the scleral suspension device can be co-molded as an integrated implantable device. The IMT and the scleral suspension device can be separate devices configured to be assembled prior to use. The IMT and the scleral suspension device can be separate devices configured to be assembled prior to insertion in the eye. The IMT and the scleral suspension device can be separate devices configured to be assembled after insertion in the eye.

The IMT can include an optically clear, outer carrier; and an optical element located within the outer carrier. The IMT can further include one or more fixation elements configured to mate with at least a region of the scleral suspension device. When mated with the scleral suspension device, a posterior surface of the outer carrier can engage the anterior surface of the support structure and the optical element of the miniature telescope optically can align with the central aperture. The optical element of the IMT can have a length sized to protrude in one or both anterior and posterior directions relative to the scleral suspension device. The IMT can further include a haptic, the haptic of the IMT can include a rigid flange that is sized to engage a region of the support structure of the suspension device. The IMT can engage with the device in a manner that eliminates any need for a haptic on the IMT. The outer carrier of the IMT can include an optically clear material. The optically clear material can include PMMA. The outer carrier of the IMT can be cylindrical having a circular cross-sectional shape.

An outer surface of the outer carrier can include a snap-fit feature configured to mate with the central aperture of the support structure. The outer carrier of the IMT can incorporate a posterior mating feature and an anterior stop. The posterior mating feature can be designed to insert through the central aperture in an anterior-to-posterior direction and provide significant resistance to withdrawal from the central aperture from a posterior-to-anterior direction. The posterior mating feature can include a flange having a barbed shape that preferentially slides anterior-to-posterior compared to posterior-to-anterior. The posterior mating feature can include a ramped shape designed to insert through the central aperture in an anterior-to-posterior direction. An outer diameter of an anterior-most end of the posterior mating feature can be sized to approximate an inner diameter of the central aperture and a posterior-most end of the posterior mating feature can be sized to approximate an outer diameter of the outer carrier. A material of the posterior mating feature can be flexible and configured to deform upon application of a force against a posterior region of the posterior mating feature and resist deformation upon application of a force against an anterior region of the posterior mating feature. The posterior mating feature can surround a full circumference of a posterior end region of the outer carrier. The posterior mating feature can be formed by at least two or more distinct mating feature located at multiple points around a circumference of a posterior end region of the outer carrier. The anterior stop can be fully annular and surround a full circumference of an anterior end region of the outer carrier. The anterior stop can be formed by at least two or more distinct mating feature located at multiple points around a circumference of an anterior end region of the outer carrier. The anterior stop and the posterior mating feature can be integral with the carrier of the IMT. The anterior stop and the posterior mating feature can be assembled with the carrier of the IMT at a time of use. A position of the anterior stop and/or the posterior mating feature relative to the carrier can be adjustable. The optical element located within the outer carrier can include at least one lens configured to magnify an image on a retina of the eye.

Each fixation arm of the plurality of fixation arms can be coupled to a trans-scleral anchor for sutureless scleral fixation of the device within the eye. At least one fixation arm of the plurality of fixation arms can be biased to curve between an origin portion and a terminal end of the at least one fixation arm so that upon placement of the device into the eye and prior to scleral fixation of the at least one fixation arm, a portion of the at least one fixation arm is visible to a user through a pupil of the eye. At rest, the device can include at least one fixation arm of the plurality of fixation arms in a folded configuration, and the at least one fixation arm is flexible and is biased towards the folded configuration. The folded configuration can include the origin portion extending away from the support structure and the anchor of the terminal portion positioned over or under at least one of a portion of the support structure and a portion of the central aperture, and a bend between the origin portion and the terminal portion.

The outer perimeter wall can have an elongate shape having a long axis and a short axis. The outer perimeter wall can have a non-circular shape. The outer perimeter wall can include two opposed side wall portions and two opposed end wall portions. Each of the opposed end wall portions can be integrally coupled to each of the opposed side wall portions at a rounded corner to form the outer perimeter wall having the non-circular shape. The inner perimeter surface defining the central aperture can be substantially cylindrical.

In an interrelated aspect, provided is an implantable device for supporting an intraocular implant in an eye including a support structure having an outer perimeter surface of an outer perimeter wall having a non-circular shape. The outer perimeter wall includes two opposed side wall portions and two opposed end wall portions. Each of the opposed end wall portions are integrally coupled to each of the opposed side wall portions at a rounded corner to form the outer perimeter wall having the non-circular shape. The support structure includes an anterior surface extending inwardly towards the central axis of the support structure from an anterior portion of the outer perimeter surface. The anterior surface has at least two awning portions. Each of the awning portions are positioned adjacent to one of the two opposed end wall portions of the outer perimeter wall. At least one of the awning portions includes a first visualization feature extending radially inwardly within a horizontal plane towards the central axis so as to be visible behind an iris during implantation of the device in the eye. The support structure includes a posterior surface extending inwardly towards the central axis from a posterior portion of the outer perimeter surface; and a central aperture extending through a full thickness of the support structure. The device includes a plurality of fixation arms configured to be placed under tension to locate and stabilize the device within the eye. A first fixation arm of the plurality of fixation arms extends outward from an origin at the outer perimeter wall of the support structure. The outer perimeter wall at the origin has a radius and the radius changes when the first fixation arm is placed under tension. The visualization feature of the at least one awning portion is located away from the origin.

The visualization feature can extend substantially within the horizontal plane prior to and after placing the at least one fixation arm under tension. The visualization feature can deflect inwardly away from the horizontal plane after placing the at least one fixation arm under tension. The outer perimeter wall can have a variable cross-sectional thickness. A thickness of the outer perimeter wall at the origin of the first fixation arm can be less than a thickness of the outer perimeter wall at an origin of at least a second fixation arm of the plurality of fixation arms. The origin of the first fixation arm can be at a first of the opposed end wall portions and the origin of the second fixation arm can be near a second of the opposed end wall portions. A thickness of the outer perimeter wall near a location of the visualization feature can be less than the thickness of the outer perimeter wall at the origin of the first fixation arm. Each of the at least two awning portions can further include an additional projection extending inwardly from the outer perimeter wall to at least partially cover a portion of an implant haptic when the implant haptic is placed into the device underneath the awning. Each of the plurality of fixation arms can be coupled to a trans-scleral anchor for sutureless scleral fixation of the device within the eye. The outer perimeter wall can include a major axis and a minor axis. The two opposed side wall portions can extend substantially along a direction of the major axis and the two opposed end wall portions can extend substantially along a direction of the minor axis. The two opposed end wall portions can be convex projecting away from the central axis. Each of the two opposed side wall portions can have a length less than a length of each of the two opposed end wall portions.

The outer perimeter wall can taper towards a trailing end of the device so that a width of the device near the trailing end is narrower than a width of the device near a leading end. The trailing end can include a first end wall portion of the two opposed end wall portions. The first end wall portion can be convex and project away from the central axis between two of the plurality of fixation arms. The leading end can include a second end wall portion of the two opposed end wall portions. The second end wall portion can be convex and project away from the central axis and a leading fixation arm can project outward from the second end wall portion. The two opposed side wall portions can extend along the major axis. An inner perimeter of the posterior surface can bound a closed, substantially circular shape of the central aperture. The central aperture can include a diameter smaller than a diameter of an optical portion of the implant. In use, the visualization feature can be directly visualized by user through a pupil of the eye. A perimeter portion of each of the at least two awning portions can form a portion of a non-circular perimeter of an anterior aperture. The anterior aperture can have a dimension larger than a diameter of an optical portion of the implant. The anterior aperture can have an area greater than an area of a closed, substantially circular shape of the central aperture bounded by the posterior surface. The visualization feature can project inward towards the central axis to narrow a dimension of the anterior aperture. The device can have an elongate shape having a major axis and a minor axis. The dimension of the anterior aperture that is narrowed can be a distance between central-most edges of the anterior aperture along the major axis of the device. The distance can be at least about 5.0 mm up to about 7.0 mm. A thickness of the support structure through the posterior surface can be about 0.05 mm to about 1.5 mm. The support structure can be substantially planar.

Each of the at least two awning portions can have a smooth geometry configured to protect an iris of the eye from irritation by the awning portions and the implant. At least one fixation arm of the plurality of fixation arms can be biased to curve between an origin portion and a terminal end of the fixation arm so that upon placement of the device into a posterior chamber of the eye and prior to trans-scleral fixation of the anchor at least a portion of the one fixation arm is visible to a user through a pupil of the eye. The awning portions at an origin of any of the plurality of fixation arms can project inwardly toward the central axis by less than about 1 mm. The visualization feature can extend radially inwardly from a location near the outer perimeter wall that increases in radius or that does not change in radius upon placing the plurality of fixation arms under tension. The at least one awning portion can include a second visualization feature. The first and second visualization features can be positioned on either side of the origin. Applying tension on the first fixation arm can draw the origin outward away from the central axis causing the radius to get smaller and the first and second visualization features to angle toward one another while remaining substantially within the horizontal plane. The intraocular implant supported by the device can be an intraocular lens, artificial iris, or an implantable miniature telescope.

In some variations, one or more of the following can optionally be included in any feasible combination in the above methods, apparatus, devices, and systems. More details are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking, the figures are not to scale in absolute terms or comparatively but are intended to be illustrative. Also, relative placement of features and elements may be modified for the purpose of illustrative clarity.

FIG. 4A is a side view of a device placed under a minimum amount of tension;

FIG. 4B is a top plan view of the device of FIG. 4A;

FIG. 4C is a side view of the device of FIG. 4A placed under a maximum amount of tension illustrating device distortion causing lift of the visualization feature;

FIG. 4D is a top plan view of the device of FIG. 4C;

Figures 1A, 1B, 1C:
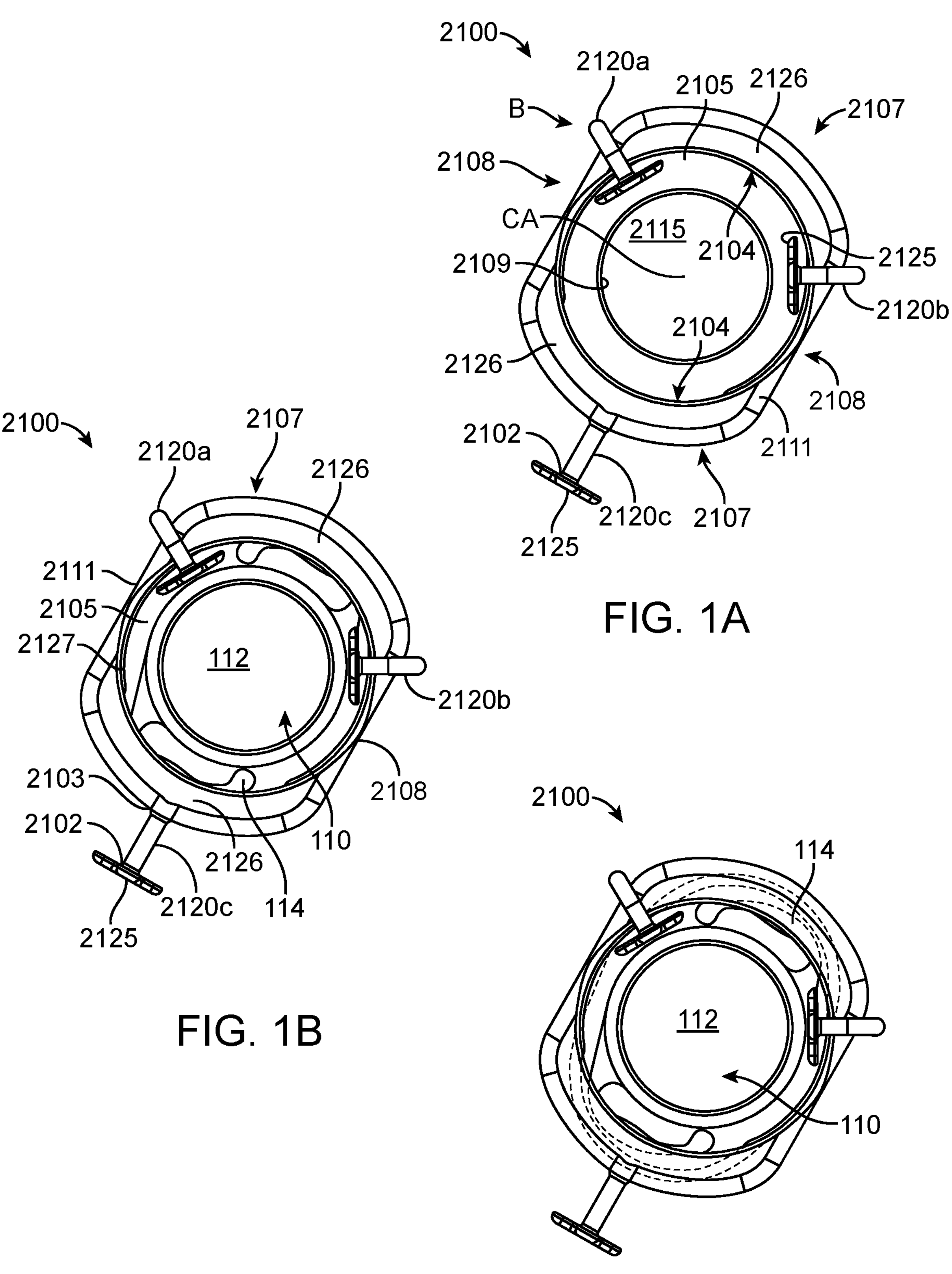
FIGS. 1A-1C are top-down views of an implementation of a device configured to accommodate an IOL.

It should be appreciated that the drawings herein are for illustration only and are not meant to be to scale.

DETAILED DESCRIPTION

The present disclosure relates generally to the field of ophthalmics, more particularly to delivery of ophthalmic devices, including artificial support structures for supporting and positioning intraocular implants having optical elements, such as implantable miniature telescopes (IMT), magnifiers, cameras, intraocular lenses (IOLs), and the like in the eye, particularly when zonular and capsular support has been compromised.

The most common treatment for aphakia caused by removal of a cataractous lens is placement of an IOL within the native lenticular capsular bag. The capsular bag, which has an anterior component and a posterior component thus creating an inner chamber, is supported by zonules, thus providing a stable structure for IOL support. In some cases, the posterior aspect of the capsular bag is incompetent or ruptured during cataract surgery, necessitating a more reliable platform for positioning an IOL. If the anterior aspect of capsular bag and its associated zonules are intact, an IOL may be placed between the anterior capsule and the iris, a position referred to as the "sulcus." In another subset of cataract surgery cases, the anterior capsule is incompetent, or the zonules are incompetent, making sulcus placement unsafe or impossible. The devices described herein can be implanted into a posterior chamber of an eye that lacks an intact capsular bag. The devices described herein can create an artificial anterior capsule with artificial zonular fixation. The devices described herein can provide a stable platform structure fixated to the eye and thereby recapitulate the native anterior capsular and zonular apparatus allowing for placement of an IOL in the artificially constructed sulcus.

The devices described herein can solve problems of other support/positioning techniques known in the art. Anterior chamber intraocular lenses placed in front of the iris can cause corneal decompensation, glaucoma, and bleeding over time due to their instability in the eye. Lenses sutured to the iris is technically difficult to implant and increases the risks of bleeding and glaucoma due to chafing of the iris. Lenses may also be sutured to the sclera, which is also technically difficult. In some cases, suture erosion/breakage requires additional surgery and risk potentially blinding infection.

The devices described herein can be implanted in a sutureless manner, which eliminates the risk of suture breakage. A sutureless trans-scleral fixation method allows for easier placement and secure attachment without concern for loosening or breaking of sutures. The devices described herein stably hold IOLs providing a reliable refractive result based on known position without concern. The devices also allow for posterior segment placement that greatly reduces risk of damage to iris, angle, or cornea. Implantation posterior to iris and cornea eliminates or reduces risk of corneal injury, iris bleeding and glaucoma. The devices described herein reduce the risk of complications compared to current technologies such as ACIOL, Iris-sutured lens, or Scleral-sutured lens. The devices described herein are designed to accommodate and provide support to a wide variety of intraocular lenses. Thus, the lens of choice can be implanted at the time of surgery or at a later date. The devices described herein replicate a natural lens capsule and in some implementations are particularly suitable for implantation into a posterior chamber of an eye lacking an intact capsular bag. For example, the devices described herein can create an artificial anterior capsule with artificial zonular fixation providing a scaffold or stable platform structure and an artificially constructed sulcus where the anterior component of the capsular bag and/or zonules of the natural lens are incompetent. The fixation arms can be externalized as needed for scleral support/fixation. In interrelated aspects, the devices need not incorporate trans-scleral fixation arms and can be supported substantially by the anterior segment of the capsular bag, if present.

A variety of tools are known to position devices within the eye, such as injectors for implantation of intraocular lenses. IOL injectors typically include a cartridge for holding the IOL and a plunger to urge the IOL out of the cartridge and into the eye. The mechanism by which the IOL is loaded and deployed in the eye can vary. Disclosed herein are delivery devices that are compatible with any of a variety of IOL inserter systems to deploy the support devices described herein. The delivery devices described herein can be used to deploy any of the support devices described herein whether they incorporate fixation arms are not and whether they are substantially planar or include an internal recess for mating with the IOL being supported.

The implant support devices and their delivery devices will be described in more detail below. It should be appreciated that the implant supported by the devices described herein can vary and that reference to one type of implant herein, such as an IOL, is not intended to be limiting. Other implants that incorporate a lens but are not considered IOLs are considered as well, including for example, implantable miniature telescopes (IMT), magnifiers, or intraocular cameras.

Additionally, where the implants are described as having a lens or optical element, it should be appreciated that other implants can be supported by the devices described herein although they may not incorporate a lens or optical element, including a biological sensor (e.g., pressure, temperature, glucose sensors). Thus, the devices described herein may be referred to interchangeably as a lens support device or a scleral suspension device and the like.

Scleral Suspension Devices

FIGS. 1A-1D and FIGS. 2A-2F show implementations of a scleral suspension device for supporting an intraocular implant 2100. The device 2100 can include a support structure or posterior platform 2105 upon, against, or within which an intraocular implant having an optical element, such as an IOL or IMT, can be supported, a central opening or aperture 2115, and one or more fixation arms 2120. The central aperture 2115 prevents the device 2100 from interfering with the patient's vision and is adapted to permit passage of light through the aperture 2115 as well as the optical element, such as IOL 110 positioned on the device 2100 or a miniature telescope positioned on, within, or through the aperture 2115 (see FIGS. 9, 10A-10D, and 11E-11K). The size of the central aperture 2115 allows light to pass through the device without any optical disturbance. The light may pass through the device towards the retina and is affected only by the optics of the optical element. The one or more fixation arms 2120 can locate and stabilize the device 2100 within the eye. The posterior platform 2105 can include an outer perimeter wall 2111 and an inner perimeter wall 2109 and the central aperture 2115 can be bound by the inner perimeter wall 2109. The posterior platform 2105 can be generally ring-shaped although the outer perimeter wall 2111 of the posterior platform 2105 need not be circular as will be discussed in more detail below. The outer perimeter wall 2111 of the posterior platform 2105 can be substantially non-circular where the inner perimeter wall 2109 is substantially circular.

FIGS. 1A-1C show top-down views of the device 2100 showing the posterior platform 2105, the central aperture 2115, and three fixation arms 2120. The posterior platform 2105 can serve as a support for the IOL 110 during optimal implantation and as a guard against the IOL falling into the posterior segment during implantation. The posterior platform 2105 can take the place of a native lenticular capsular bag, particularly where the anterior aspect and associated zonules are incompetent making sulcus placement of an IOL unsafe or impossible. Placement of the posterior platform 2105 in a patient without a competent capsular bag can create an anterior capsule device. The fixation arms 2120 can provide artificial zonular fixation stabilizing the support structure as a stable platform for placement of an intraocular lens within the artificially constructed sulcus. FIG. 2D shows the cornea 5, iris 10, ciliary body 15, sclera 20, and the pupil 30 defined centrally through the iris 10.

In some implementations, the posterior platform 2105 can be substantially flat or planar. The posterior platform 2105 can have an anterior-facing surface directed towards a front of the eye when the posterior platform 2105 is in use and a posterior-facing surface towards a back of the eye when the posterior platform 2105 is in use. The planar posterior platform 2105 can act as a support against which the optical element can be positioned. The planar anterior and posterior surfaces need not include any projections, channels, or capturing components to hold the optical element relative to it. For example, the posterior platform 2105 can create an artificial anterior segment of the capsular bag for the optical element to be positioned against, but need not hold the optical element within an interior surface. Thus, the optical element can remain fully external to the posterior platform 2105 during use and no projections, overhangs, or other surfaces positioned relative to the optical element aside from the substantially planar surfaces of the posterior platform 2105. Thus, each of the anterior-facing and posterior-facing surfaces can be substantially smooth planar surfaces that are free of any projections or overhangs above the surfaces. Each of the anterior-facing and posterior-facing surfaces can also be free of any indentations, grooves, divots, or openings other than the central aperture 2115 extending through it. The substantially flat posterior platform 2105 can taper towards the central aperture 2115. The tapered edge or inner wall 2109 defining the aperture 2115 has an anterior-to-posterior thickness that is less than an anterior-to-posterior thickness of the support structure away from the aperture 2115.

In other implementations, the posterior platform 2105 can incorporate one or more projections extending away from at least one of the anterior-facing surface and the posterior-facing surface. In still other implementations, the posterior platform 2105 can optionally or additionally include a recess in at least one of the anterior-facing or posterior-facing surfaces that is sized and shaped to receive the optical element (see FIGS. 1A-1C and others described in more detail below). In still other implementations, the posterior platform 2105 can be thicker near a central region and define a central aperture 2115 that has an extended anterior-to-posterior depth to receive at least a portion of an implant, such as a miniature telescope or other optical element as will be described in more detail below (sec, e.g., FIGS. 9, 10A-10D, and 11E-11K). The platform thickness between an anterior surface and a posterior surface of the platform 2105 can be variable such that the greatest thickness of the platform 2105 can be the central part of the platform 2105 through which the central aperture 2115 extends (i.e., inner wall 2109). The part of the platform 2105 that is the thinnest can be a peripheral region near where the fixation arms project outward away from the platform 2105 (i.e., outer wall 2111). The thickness of the platform 2105 tapers from the thicker, central aperture to the thinner, outer perimeter. The centrally thicker platform 2105 prevents or reduces the risk of tilt and decentration.

The recess can form a lip surrounding the central aperture 2115 that is sized to engage with and support a perimeter of the optic against the lip (see FIG. 1C). The recess in the central 6.0-7.0 mm part of the posterior platform 2105 can limit the translational movement of the optic. The recess can additionally incorporate a concave, dished out section to increase the interfacial surface area of the optical element with the posterior platform 2105. The recess can incorporate one or more features that additionally prevent rotational motion around the visual axis or the central axis CA of the device. FIGS. 1A-1D, 2A-2C illustrate additional implementations of a device incorporating a recess within which an optical element may be received and are described in more detail below.

Whether the posterior platform 2105 is recessed or not and/or incorporates one or more projections from its surface or not, the anterior-to-posterior thickness of the posterior platform 2105 is minimized to avoid impacting the iris 10. In some implementations, the posterior platform 2105 has an anterior-to-posterior thickness that is uniformly thin from the central aperture 2115 to the outer perimeter (sec, e.g., FIG. 2C). In other implementations, the posterior platform 2105 has an anterior-to-posterior thickness that is non-uniform and is thicker near the central aperture and thinner near the outer perimeter. This non-uniform thickness where the posterior platform 2105 tapers moving outward away from the central aperture 2115 is particularly helpful in preventing tilt of an optic mated within the central aperture 2115.

The central aperture 2115 can extend through the full thickness of the posterior platform 2105 from the anterior-facing surface through to the posterior-facing surface such that the posterior platform 2105 additionally includes an inner wall 2109 having an inner perimeter surface defining the central aperture 2115 and an outer wall 2111 having an outer perimeter surface defining the overall shape of the posterior platform 2105. This can provide a substantially annular shape to the posterior platform 2105. However, the annular posterior platform 2105 need not be circular on both its inner and outer perimeter surfaces. The inner perimeter surface can have a circumference and form a uniform, substantially circular shape whereas the outer perimeter surface can form a substantially non-circular shape. The inner perimeter surface need not be perfectly circular and can also be somewhat oval or elongate while still different from the substantially non-circular shape of the outer perimeter surface. As will be discussed in more detail below, the non-circular shape of the outer perimeter surface comprises a plurality of shorter sides or lobes 2107 projecting outward from a plurality of elongate sides 2108. The plurality of lobes 2107 can project radially away from the central aperture 2115. The plurality of elongate sides 2108 can be substantially flat or concave as described elsewhere herein. In some implementations, the device includes at least three fixation arms 2120 coupled to the posterior platform 2105 that are configured to be placed under tension to locate and stabilize the device within the eye. Each of the three fixation arms 2120 can extend outward from a respective one of the plurality of elongate sides 2108. The posterior platform 2105, thus, can have a width between the outer perimeter surface and the inner perimeter surface that varies around the circumference. The central aperture 2115 is designed to allow for vision through the device. In some implementations, the posterior platform 2105 is substantially flat and the optical element sits on the anterior-facing surface (or posterior-facing surface) of the posterior platform 2105, but is not held or contained by the central aperture 2115. In other implementations, the posterior platform 2105 is generally planar, but includes a recess 2104 surrounding the central aperture 2115 such that the optical element sitting on the anterior-facing surface of the posterior platform 2105 engages a lip formed by the recess 2104. In still further implementations, the posterior platform 2105 mates with the optical element, which is received at least in part within the central aperture 2115 extending through the posterior platform 2105. The posterior platform 2105 can have a first thickness between the anterior-facing surface and the posterior-facing surface defining the central aperture 2115 and a second thickness defining the outer wall 2111 that is less than the first thickness.

The thickness of the posterior platform 2105 between the anterior-facing surface and the posterior-facing surface can be between about 0.05 mm and 1.5 mm, or between about 0.15 mm and 1.0 mm, or between about 0.1 mm and 0.5 mm, or between about 0.2 mm and 0.4 mm. The thickness of the posterior platform 2105 can be thinner than 0.15 mm and still provide sufficient support for an optical element, for example, due to the fixation arms 2120 being under tension. In some implementations, the thickness of the posterior platform 2105 at the central aperture 2115 can be greater than 0.2 mm up to about 2 mm and the thickness of the posterior platform 2105 at the outer wall 2111 can be less than 0.2 mm down to about 0.15 mm. The inner perimeter surface or inner wall 2109 defining the central aperture 2115 can be smooth and free of any concavity, groove, channel, or other surface feature. In some implementations, the inner perimeter surface or inner wall 2109 is convex and projects towards a central axis CA of the device and the outer perimeter surface or outer wall 2111 is also convex and projects away from the central axis CA of the device. The convex inner and outer perimeter surfaces formed by the inner and outer walls 2109, 2111 can create a cross-sectional shape to the posterior platform 2105 when taken across a center of the central aperture 2115 that forms a pair of rounded rods. In some implementations, the anterior-facing surface and the posterior-facing surface each taper towards the central aperture 2115 such that the inner perimeter surface of the inner wall 2109 is shaped as a single narrow ridge or point projecting towards the central axis CA of the device.

The central aperture 2115 can also be the only aperture extending through the support 2105 such that the support 2105 has only a single aperture extending through its full thickness. The inner diameter of the aperture 2115 is designed to be generally universal for a wide range of optical elements, such as different IOL types. The aperture 2115 is sized so the support 2105 avoids overlapping substantially with the optic of the IOL. Conventional IOLs typically have optics with an outer diameter of 6 mm although this size can vary depending on the IOL. A device having a central aperture 2115 inner diameter that is less than 5.0 mm down to about 4.0 mm can be used with some IOLs. A device having a central aperture 2115 inner diameter that is between 5.0 mm to about 6.0 mm can be used with most IOLs such that the device is nearly universal for use with any conventional haptic-stabilized IOL. The minimum inner diameter of the aperture 2115 can be greater than about 4.0 mm, greater than about 4.5 mm, greater than about 5.0 mm, greater than about 5.5 mm, greater than about 6.0 mm, greater than about 6.5 mm, up to about 7.0 mm, up to about 8.0 mm, up to about 9.0 mm, up to about 10 mm and any range in between. In some implementations, the implant being supported by the scleral suspension device 2100 is designed to insert at least partially through the central aperture 2115 (see FIG. 10C-10D). The central aperture 2115 in this implementation can be about 2 mm-6 mm, 3 mm-5 mm, or about 3.5 mm-4.5 mm.

One or more of the fixation arms 2120 can be substantially straight between their origin with the posterior platform 2105 and their terminal ends. The straight fixation arm, which can be the leading fixation arm 2120*c* from the perspective of direction of implantation into an eye, can extend along a single longitudinal axis between the origin 2103 and terminal end 2102 without any bends or curves away from the single longitudinal axis. The straight fixation arm(s) 2120*c* can extend orthogonal to the outer perimeter surface of the posterior platform 2105 outer wall 2111. The longitudinal axis of the straight fixation arm(s) 2120*c* can be positioned orthogonal to the outer perimeter surface of the outer wall 2111. The plane of the anterior-facing surface of the posterior platform 2105 and the longitudinal axis of the straight fixation arm(s) 2120*c* can be parallel to one another as can the plane of the posterior-facing surface of the support structure and the longitudinal axis.

The one or more fixation arms 2120 are preferably trans-scleral fixation arms that are designed to be atraumatically externalized and held in place by its geometry and mechanical properties alone, i.e., not requiring sutures or glue. The fixation arms 2120 are configured to be placed under tension to locate and stabilize the device within the eye, preferably along at least 3 points of fixation. The externalized portion or anchor 2125 (also referred to herein as an anchoring footplate or footplate) at a peripheral end (also referred to herein as a terminal end or a terminal portion) of the fixation arm 2120 can sit sub-conjunctivally to anchor the arm 2120 in position. The anchor 2125 of the fixation arm 2120 can have a sturdy, but low-profile geometry to remain stable and not re-enter the eye and minimally erode the conjunctiva. Additionally, the fixation arms 2120 of the device 2100 may be manufactured in a way to facilitate easy visualization and manipulation of the device prior to surgery. At least one of the fixation arms 2120 may be manufactured to have a geometry that is substantially non-planar at rest and then be manipulated into a planar configuration during the implantation procedure and, for example, when placed under tension.

The device 2100 can include one, two, three, or more fixation arms 2120. In a preferred implementation, the device 2100 includes three fixation arms 2120 that are arranged symmetrically or equidistant around the perimeter of the posterior platform 2105. The fixation arms 2120 can center the posterior platform 2105 and provide sufficient support for long-term stability. In some implementations, that may be accomplished by a single fixation arm 2120. In other implementations, the one or more fixation arms includes three fixation arms 2120 symmetrically arranged around a perimeter of the support structure. The fixation arm 2120 can be constructed from a semi-rigid material or may have a geometry that provides sufficient structural rigidity.

The device 2100 can also include just two fixation arms 2120. These fixation arms 2120 may be under equal and opposite tension when implanted and anchored trans-sclerally. Alternatively, the fixation arms 2120 may be asymmetric such that one fixation arm 2120 is under tension and the other fixation arm 2120 has a rigidity and length that it functions as a rigid spacing element. A fixation element that is rigid or capable of applying a spring force can rely on penetration of the adjacent tissue or being wedged into place. A tensioned fixation element can rely on a slight stretch or expansion of the material once placed. One or both of the fixation arms 2120 may be produced with an inward biased configuration in which the fixation arm is biased towards an anterior projecting curve or a folded configuration as described elsewhere herein. The fixation arms 2120 may have a paddle like geometry that resists rotation when engaged with ocular tissue.

The device 2100 can also include three or more fixation arms 2120. Three fixation arms 2120 can provide the device 2100 with a defined fixation plane that is substantially parallel to the Z-plane (vertical plane) of the eye. The fixation arms 2120 can be designed and deployed in a manner that puts each fixation arm 2120 in equal and opposite tension. Alternatively, one or more fixation arms 2120 may be designed to have a rigidity and length allowing to behave as a rigid spacing element. Zero, one, two, or all three or more of the fixation arms 2120 can be manufactured with an inward biased design or biased towards a center of the device or the central axis CA of the device (see FIGS. 1A-1D, 2A-2C). The inwardly biased fixation arms 2120 can extend from the support structure and have a folded configuration prior to implantation. At least one, but fewer than all, of the fixation arms may be biased or curved as described herein. At least two, but fewer than all may be biased or curved as described herein. In some implementations, all the fixation arms 2120 may be biased or curve. The device can include three fixation arms, wherein two of the three fixation arms are flexible and biased towards a folded configuration, and a third fixation arm is less flexible than the other two and is biased towards an unfolded configuration. The folded configuration of each of the fixation arms can bias the terminal end portion of the fixation arms towards a central axis CA of the device. The support structure can be biased towards a substantially flat or planar configuration while the fixation arm(s) is biased towards the folded configuration that is not substantially flat or planar.

Once implanted and fixed trans-sclerally, the inwardly biased arms are unbent or unfolded away from their folded, inwardly biased configuration. In a preferred implementation, two fixation arms 2120 have an inward bias geometry and the third fixation arm 2120 has increased cross-sectional area-increasing its rigidity. The inwardly biased fixation arms 2120 can incorporate a bend between an origin of the arm with the posterior platform 2105 and their terminal end. The two bent fixation arms 2120 can be biased towards the central axis CA of the device towards a folded configuration.

In an implementation, the device 2100 can include at least three fixation arms 2120. Prior to implantation, one of the at least three fixation arms can extend in an unfolded configuration from the support structure and at least two of the at least three fixation arms extend in a folded configuration from the support structure. And, prior to implantation, one of the at least three fixation arms can be biased towards the unfolded configuration and at least two of the at least three fixation arms can be biased toward the folded configuration. After implantation, each of the arms biased toward the folded configuration can be unfolded.

Each of the fixation arms 2120 can include an origin portion 2103 at the posterior platform 2105 and a terminal end portion 2102 coupled to an atraumatic anchor 2125 for sutureless, trans-scleral fixation. Prior to trans-scleral fixation of the anchors 2125, one of the plurality of fixation arms 2120 (up to all of the fixation arms 2120) can include a curved fixation arm 2120 that is curved between its origin portion 2103 and its terminal end 2102 forming a bend B (see FIGS. 1A-1D) enabling visualization of at least a portion of the curved fixation arm 2120 through the pupil 30 of the eye. After trans-scleral fixation of the anchors 2125, each of the plurality of fixation arms 2120 can be tensioned between the origin portion and the terminal end to align the support structure relative to the Z-plane of the eye. The posterior platform 2105 is adapted to provide support for an intraocular lens. The central aperture 2115 extending through the full thickness of the posterior platform 2105 is adapted to permit passage of light through both the central aperture 2115 and the optical element supported by the posterior platform 2105. The curved fixation arm 2120 can curve anteriorly such that a portion of the arm 2120 such as the terminal end 2102 and/or its atraumatic anchor 2125 is positioned over at least a portion of the posterior platform 2105 (e.g., the upper surface of the posterior platform 2105 and/or over a region of the central aperture 2115). Alternatively, the curved fixation arm(s) 2120 can curve posteriorly such that a portion of the arm 2120 such as the terminal end 2102 and/or its atraumatic anchor 2125 is positioned under at least a portion of the posterior platform 2105 (e.g., the lower surface of the posterior platform 2105 and/or under a region of the central aperture 2115).

Two of the three fixation arms 2120 curve inward such that they are biased towards a folded configuration at rest. The arms 2120 extend outward substantially orthogonally from the posterior platform 2105, such as from their origin 2103 at the posterior platform 2105 and make a turn (anteriorly or posteriorly) forming a curve between the origin 2103 and the terminal ends 2102 of the arms 2120. The curve of the arm 2120 can result in the terminal end 2102 of the arm 2120 being positioned nearer to its own origin portion 2103. In some implementations, the arm 2120 curves in an anterior direction such that the terminal end 2102 of the arm 2120 is positioned anterior to the arm's origin portion 2103 or over at least a portion of the anterior-facing surface of the posterior platform 2105 near the arm's origin portion 2103. In other implementations, the arms 2120 can curve in a posterior direction such that the terminal end 2102 of the arm 2120 is positioned posterior to the arm's origin portion 2103 or under at least a portion of the posterior-facing surface of the posterior platform 2105 near the arm's origin portion 2103. In an implementation, the anchors 2125 of the curved fixation arms 2120 can curve away from a first plane of the support structure (e.g., Z-plane of the eye) into a second plane that is parallel to the first plane. The second plane can be anterior or posterior to the first plane depending on whether the arms 2120 curve anteriorly or posteriorly. The curve can be in a direction that is substantially transverse (e.g., X-plane) to the plane of the posterior platform 2105 (e.g., Z-plane). The dilated pupil (depending on whether adult or pediatric patient) can have a diameter up to about 8 mm. The curve positions the anchors 2125 of the curved fixation arms 2120 to be positioned within a diameter of a circle in that second plane that is visible within the diameter of a dilated pupil so as to not impede visualization by the opaque iris, for example, between about 3 mm up to about 7.5 mm, more preferably about 7 mm. The anchor 2125 of each of the curved fixation arms 120 can be positioned a distance from the center of the device, for example, about 1.5 mm, 2.0 mm, 2.5 mm, 3.0 mm, up to an no greater than about 3.5 mm, or no greater than about 4.0 mm from the center of the device. The curved arms 2120 provide for positioning the terminal end portions 2102 and/or the anchors 2125 within this diameter or this distance from the center of the device allowing for case of visualization. The third of the three fixation arms 2120 is biased into a straight or unfolded configuration at rest. The third arm 2120 extends outward orthogonally from its origin 2103 at the posterior platform 2105 and makes no turn or bend. Rather, the entire third arm 2120 is entirely straight and extends substantially along a single axis. The two fixation arms that, at rest, were biased towards a folded configuration are now in an unfolded configuration, for example, by tensioning the arms 2120 via the trans-scleral anchors being externalized.

The fixation arms 2120 may be uniformly distributed around the device 2100 to provide uniform tension. Alternatively, the fixation arms 2120 may be oriented in a non-uniform distribution, for example, with three fixation arms 2120 that are 90 degrees from one another. In this circumstance two of the fixation arms 2120 would be 180 degrees from each other, providing opposing tension; while the third fixation arm 2120 serves primarily to prevent the device 100 from rotating.

The posterior platform 2105 can provide several functions. The posterior platform 2105 can have a surface (anterior-facing surface or posterior-facing surface) forming a stable platform against which an IOL 110 can be placed during use. The posterior platform 2105 can take the place of a capsular bag, particularly one where the posterior and/or anterior aspects of the bag are ruptured or otherwise incompetent. Its geometric and mechanical function not only supports the IOL 110 when in use, it can also serve to assist in the centration of an IOL 110 in the case of an asymmetric eye or asymmetric surgical procedure. The posterior platform 2105 can be coupled to the one or more fixation arms 2120. Where the posterior platform 2105 provides artificial anterior capsule support for the IOL, the fixation arms 2120 provide artificial zonular apparatus. Thus, the device provides a stable platform structure fixated to the eye recapitulating the native anterior capsule and zonular apparatus that would normally allow for placement of an IOL. The posterior platform 2105 geometry and mechanical properties can be designed to allow the fixation arms 2120 to function as intended and withstand any torsional or tensile forces that may be imparted by the fixation arms 2120.

The fixation arms 2120 and posterior platform 2105 are designed such that a properly fixated device 2100 will position the central aperture 2115 in a manner that will not interfere with the patient's vision. The surgeon can place an IOL 110 on through the posterior platform 2105 thereby providing the patient with their needed refractive correction.

The ciliary body 15 has a substantially circular or elliptical shape, with the vertical axis being 0.5 mm longer than the horizontal axis on average. The posterior platform 2105 can interface with a patient's ciliary body to provide centration of the device 2100 within the eye. A substantially round or elliptical posterior platform 2105 can provide centration with the similarly round or elliptical ciliary body. However, matching of the shapes and 360 degree contact between the posterior platform 2105 and the ciliary body can lead to inflammation or damage, which could negatively impact aqueous production. In a preferred implementation, the posterior platform 2105 has a continuous inner circumference forming a uniform, substantially circular (or near circular) shaped inner wall 2109 defining the central aperture 2115 and an outer perimeter surface forming a substantially non-circular shaped outer wall 2111 providing the support structure 2105 with a substantially non-circular geometry. The non-circular outer geometry of the posterior platform 2105 can provide centration of the device 2100 without 360 degree contact with the ciliary body along the substantially non-circular shaped outer perimeter surface. The shape of the posterior platform 2105 can provide sufficient contact between the posterior platform 2105 and the ciliary body to aid in centration and support of an IOL 110 without causing inflammation and damage. In some implementations, the shape of the posterior platform 2105 allows for contact with the ciliary body that is about 120 degrees or less, preferably between 1 and 45 degrees, or between 1 and 20 degrees. Limiting the contact to 120 degrees or less significantly reduces the risk of inflammation or impairment of aqueous production. A substantially non-circular or elliptical posterior platform 2105 allows allow for gentle contact between the device 2100 and the ciliary body that provides centration without requiring an exact match with the patient's specific dimensions. The radius of curvature of the posterior platform 2105 can be less than that of the ciliary processes. Thus, the posterior platform 2105 can contact the ciliary processes at 3 distinct points rather than across a calculable range. For example, when in use, the substantially non-circular shaped outer perimeter surface of the posterior platform 2105 can contact the ciliary processes at these three distinct points. In other implementations, the lobes 2107 of the device 2100 are positioned near, but avoid contacting eye tissues (e.g., the ciliary body) once each fixation arm 2120 is implanted and placed under tension. This arrangement allows for the lobes 2107 to help in centration of the device and to avoid over-tensioning one arm 2120 relative to another arm 2120. If a fixation arm 2120 is pulled too far during externalization of its anchor 2125, the neighboring lobes 2107 on either side of that fixation arm 2120 may abut against the ciliary body during implantation urging the posterior platform 2105 away from the ciliary body and promoting the device 2100 into a more central alignment. Once implanted, the lobes 2107 of the device can be positioned near eye tissue (e.g., the ciliary body) with or without touching the eye tissue. The tensioned fixation arms 2120 can pull on the posterior platform 2105 substantially equally around its perimeter. The tension applied around the posterior platform 2105 can substantially align a central axis CA of the device 2100 extending through the central aperture 2115 with the visual axis of the eye and allow for the planar surface of the posterior platform 2105 to be stabilized substantially parallel to the Z-plane (vertical plane) of the eye. The central axis CA of the device 2100 need not be perfectly aligned (coincident) with the visual axis of the eye.

The non-circular outer wall 2111 of the posterior platform 2105 can include a plurality of shorter sides or lobes 2107 projecting outward (i.e., in a convex manner) from a plurality of elongate sides 2108 that are substantially flat or concave. This can form an outer wall 2111 of the posterior platform 2105 having an alternating pattern of convex lobes and concave or flat sides. In an implementation, the posterior platform 2105 can include two convex lobes 2107 projecting between two flat or slightly concave elongate sides 2108.

In the implementations shown in FIG. 1A through FIG. 2A, the lobes 2107 form rounded ends of the device rather than the corners. The non-circular shape of the device is generally trapezoidal, rounded rectangle, or stadium shaped. The shape can include two elongate sides 2108 that are substantially straight along at least a portion of their length and connected by two lobes 2107 that form opposing curved semi-circular ends of the device. The elongate sides 2108 can bow outwardly along a curve for at least a portion of their length and can be straight for at least a portion of the length. FIG. 2F illustrates a perimeter 2111 or footprint of a device (excluding any fixation arms) showing four sides of the device. A first lobe 2107 forms the trailing end 2106 of the device, which can have a slightly narrower width (e.g., about 7.0 mm from side wall 2112 to opposite side wall 2112) compared to the width of the second lobe 2107 forming the leading end 2101 of the device (e.g., about 7.4 mm from side wall 2112 to opposite side wall 2112). The taper can create a width difference between leading end 2101 and trailing end 2106 that is about 0.1 mm to about 1.0 mm, preferably about 0.20 mm and roughly about a 0.5-5.0 degree angle from the center line of the device. The elongate sides 2108 of FIG. 2F can, but need not be straight along their entire length or lie parallel to one another. The two elongate sides 2108 are connected to the two lobes 2107 by four rounded corners 2123. The rounded corners 2123 can, but need not all have the same radius of curvature R'. The rounded corner 2123 in the upper left quadrant of FIG. 2F has a radius of curvature R' that is about 0 to about 3.5 mm, preferably about 1.67. The rounded corner in the upper right quadrant of FIG. 2F is its mirror image having the same radius of curvature of the rounded corner 2123 on the opposite side of the axis of symmetry along the major axis A of the device. The rounded corner 2123 in the lower left quadrant of FIG. 2F can, but need not have the same radius of curvature R' as the rounded corners 2123 in the upper quadrants, for example, about 0 to about 3.5 mm, preferably about 1.67. The rounded corners 2123 in the lower quadrants can be the same so that they are mirror images of one another on the opposite side of the axis of symmetry along the major axis A of the device. However, the corners 2123 in the upper and lower quadrants on opposite sides of the minor axis of the device need not be mirror images of one another. Meaning the minor axis extending generally along line Z shown in FIG. 2F need not be a line of symmetry. The lobes 2107 can have different radius of curvature R compared to the radius of curvature R' of the respective corners 2123. The radius of curvature R can be anywhere from a flat line to a radius of about 3.5 mm. A "lobe" as used herein can include a rounded corner of the device or an end of the device where the end projects or is curved outwardly relative to the center axis of the device. The rounded corners can, but need not have the same radius of curvature. The lobes also need not have the same shape and/or length so that a first end of the device may be slightly wider than the opposite end of the device (see, for example, FIGS. 1D and 2F).

The lobes 2107 can act as bumpers against the ciliary body and/or within the ciliary sulcus to provide anti-rotation function in the Z-plane and/or prevent displacement within the Z-plane to maintain proper alignment between the central aperture 2115 and the eye's visual axis. The plurality of fixation arms 2120 can be positioned on the elongate sides 2108 and the plurality of lobes 2107 project outward between the plurality of fixation arms 2120. The fixation arms 2120 each can have a length that is longer than a distance the lobes 2107 project outward. The fixation arms 2120 can have a uniform length relative to one another or can have different lengths, which will be described in more detail below. As mentioned above, the posterior platform 2105 can have a circular inner wall 2109 defining the central aperture 2115. The plurality of lobes 2107 projecting outward from the central aperture 2115 provides a varying thickness in the plane of the central aperture 2115 between the inner wall 2109 and outer wall 2111. The thickness of the posterior platform 2105 between the inner wall 2109 and the outer wall 2111 at the location of the substantially flat elongate sides 2108 is less than a thickness of the support structure between the inner wall 2109 and the outer wall 2111 at the location of the short sides or lobes 2107. The number of lobes 2107 of the posterior platform 2105 can vary providing the support structure with any of a variety of non-circular shapes including rounded triangle, rounded rectangle, rounded pentagon, rounded hexagon, trefoil, quatrefoil, cinquefoil, trapezoid, stadium shape, cyclogon, egg, lens, triquestra, vesical piscis, reuleaux polygon, or other geometric or free-form etc. The projections or corners of these non-circular geometries can be rounded to provide gentle, non-penetrating contact with ciliary tissue such as the ciliary body. Alternatively, the device 2100 can be designed to utilize the pars plana or scleral wall for centration assistance. In this implementation, the device 2100 can be positioned posterior to the ciliary processes.

In still further implementations, the posterior platform 2105 may have an overall shape that tapers from a leading end to a trailing end. For example, the device 100 can be configured for insertion through an incision such that a leading end of the posterior platform 2105 (i.e., the end of the device inserted first through the incision) is wider leading end than trailing end such that the overall shape tapers from leading end to trailing end (sec, for example, FIG. 1D, 2A). The leading end of the posterior platform 2105 can be a region of the posterior platform 2105 coupled to the leading fixation arm 2120*c*. The trailing end of the posterior platform 2105 can be a region of the posterior platform 2105 located between the two trailing fixation arms 2120*a*, 2120*b*. The region near the leading fixation arm 2120*c* can have a width that is greater than the region between the trailing arms 2120*a*, 2120*b*. This tapered shape from leading end to trailing end of the device 2100 results in it taking on a desired shape when loaded onto an insertion tool and stretch into an insertion configuration, which will be described in more detail below. The taper from leading end to trailing end can exist regardless of the overall shape of the posterior platform 2105.

The anchors 2125 can be coupled to or positioned at an outer terminus of the fixation arms 2120. These geometries are designed to be easily externalized by the surgeon and to stabilize tension on the device throughout its useful life. The anchors 2125 can have a generally low profile and can have a geometry (e.g., rounded) designed to limit conjunctival erosion and eyelid irritation. The terminal end of the fixation arm 2120 can have an anchor 2125 configured to be positioned external to the sclera 20 to secure the posterior platform 2105 and prevent centripetal slippage. The geometry of the anchor 2125 allows for the surgeon to pass the anchor 2125 through a puncture or incision in the sclera 20 using forceps, trocars or other surgical tool. The anchor 2125 can have a geometry that resembles a nail head, a T-bar, a multi-pronged shaped, or any other geometry that can preferentially be passed through the sclera 20 in a first direction and resist pulling out the direction of insertion to maintain its external position when the arm 2120 is placed under the tension anticipated through the lifetime of the device. The anchor 2125 is designed to have a profile and geometry that does not cause irritation to the eyelid or conjunctiva throughout the useful life of the device 2100. As such, preferred geometries will have minimal thickness profiles with smooth, rounded and/or tapering edges. The anchor 2125 can have a substantially constant thickness or can have a thickness that various over its length, as discussed in more detail below.

The anchors 2125 described herein are configured to be both easily externalized and resistant to re-internalization following externalization. The anchors can be designed such that they are graspable using an ophthalmic tool (e.g., 23, 25, or 27 gauge). A geometry that is ideal for grasping with an ophthalmic tool may not necessarily be ideal for firm fixation. The anchors 2125 can have variations in thickness, width, and/or height. The anchors 2125 can include a central portion and one or more graspable portions at a periphery of the central portion. The central portion can be arranged to lie over the wound (sclerotomy) through which the anchor 2125 was inserted and the graspable portions arranged immediately adjacent the wound. The central portion can have increased thickness, height, and/or width compared to the graspable portions at the periphery. The increased thickness, height, and/or width of the central portion can add bulk to the area over the wound and thereby reduce the likelihood that tension on the fixation arm pulls the anchor 2125 back through the wound. The central portion of the anchor 2125 may have a thickness along a longitudinal axis of the arm 2120 that is greater than a thickness of the graspable portion. For example, the thickness can be between about 1.2 to 5.0 times as thick as a thickness of the graspable portion. In other implementations, the central portion may have a width or height that is between about 1.2 to 5.0 times as wide or as high as the graspable portions. The geometry of the bulkier area is designed to resist deformation when under the tensile forces associated with normal use of the device. The bulkier central portion can collapse inward to fold over onto the terminal end of the arm 2120 to which it is attached during externalization. Once the arms 2120 are placed under tension, the bulkier central portion is incapable of being folded over away from the terminal end of the arm 2120 onto itself, which prevents the externalized anchor 2125 from being pulled back through the wound. Thus, the central portion can be pulled through the wound in the first direction (outward from the eye) despite its greater bulk, but is prevented from being pulled through the wound in the second opposite direction (inward towards the eye) because of its greater bulk. Fixation arms 2120 extending to the eye wall can be difficult to manipulate as they can be blocked from view by the peripheral iris 10, limbus and sclera 20. As discussed above, one or more of the fixation arms 2120 can be inwardly biased toward a folded configuration. Each of the fixation arms 2120 may extend initially from the posterior platform 2105 outward in an orthogonal direction and then curve or fold anteriorly (or posteriorly) such that the terminal ends of the fixation arms 2120 are positioned over at least a portion of the fixation arm 2120, the posterior platform 2105, or the central aperture 2115 extending through the posterior platform 2105. At least a portion of the bent fixation arms (i.e., the terminal ends and/or the anchors 2125) can be more easily visualized through a dilated pupil and visualization is not impeded by the opaque iris 10. This inward (centripetal) bias also allows the bent fixation arms 2120 to be safely grasped and manipulated during device implantation. Each of the fixation arms 2120 of the device 2100 can have inward bias toward a folded configuration or just a selection of the fixation arms 2120 can have inward bias (e.g., one, two, up to less than all fixation arms 2120).

The fixation arm 2120 can also be molded to incorporate a bend or curve between its origin with the posterior platform 2105 and the terminal anchor 2125 (see FIGS. 1A-1D, 2A-2C). The bent fixation arm(s) 2120 can be biased towards a folded configuration. For example, one or more of the fixation arms 2120 can bend between 90 degrees and 270 degrees from its origin with the posterior platform 2105 in a radial and centripetal direction. The terminal end of the bent fixation arms 2120 thus, lie in a different plane from a plane of the posterior platform 2105. When in a resting state prior to being positioned in the eye, the terminal end of at least a first fixation arm 2120 of the plurality of fixation arms 2120 can incorporate a bend between its origin with the support structure and its terminal end forming a bent arm. The bent arm can extend at least a first distance from its origin orthogonal to the posterior platform 2105. The bent arm can then curve upward (anteriorly) away from the plane of the posterior platform 2105 at least another distance. The bent arm 2120 can then curve back towards its origin or towards the central axis CA of the device. This can result in the terminal end of the bent arm 2120 lying in a different plane than the plane of the posterior platform 2105. The curve or bend in the arm 2120 can be projecting outward away from the central axis CA and away from both the arm's origin 2103 and terminal end 2102. The trans-scleral anchor 2125 and/or a terminal portion of the fixation arm 2120 can be positioned over or anterior to at least a portion of the posterior platform 2105 or positioned over at least a portion of the central aperture 2115. Alternatively, the bent arm(s) 2120 can curve downward (posteriorly) away from the plane of the posterior platform 2105 at least a distance and the trans-scleral anchor 2125 or a terminal portion of the fixation arm 2120 can be positioned under or posterior to at least a portion of the posterior platform 2105 and/or under or posterior to at least a portion of the central aperture 2115. The folded configuration (whether the arms 2120 curve anteriorly or posteriorly) allows for at least a portion of the bent fixation arms 2120 such as the terminal ends of the bent fixation arms 2120 and/or their anchors 2125 to be visualized through the pupil and not impeded by the opaque iris. Only one arm 2120 of the fixation arms 2120, two arms 2120 of the fixation arms 2120, or all of the fixation arms 2120 can incorporate a curve.

Once the device is positioned and anchored in the eye, the fixation arms 2120 are placed under tension such that the bent arm is unfurled away from this folded configuration and is no longer bent. The terminal end of the arm 2120 is urged away from this resting state in which the arm 2120 is in a folded configuration to urge the bent fixation arm into a straight or unfolded configuration.

The bend of the folded configuration can be a gradual, smooth bend having a radius of curvature or can bend to form one or more distinct angles along a length of the arm 2120. The bend can be tight enough to avoid projecting too far anterior while still capable of being unfurled or placed into an unfolded configuration with relative ease without imparting undue stress on the posterior platform 2105. The inward biased geometry can have a curve that is between about 0.10 mm to about 2.5 mm radius of curvature on the inner curve (anterior-facing side) and between about 0.6 mm to about 3.0 mm radius of curvature on the outer curve (posterior-facing side). In an implementation, the biased fixation arm 2120 curves a full radius of 180 degrees and has an inward biased geometry that is about 0.63 mm radius of curvature on the inner curve and about 1.13 mm on the outer curve such that the posterior platform 2105 and the biased fixation arm are spaced by about 1.25 mm. The start point of the curve (near the origin 2103 with the posterior platform 2105) and the end point of the curve (near the terminus 2102 at the trans-scleral anchor 2125) can have a plurality of radiuses such that the curve changes over the length of the fixation arm 2120. The curve of the biased fixation arms 2120 can have an average curvature between about 0.15 mm to about 2 mm on the inner curve.

The bent fixation arms 2120, after implantation and prior to fixation with the scleral wall, can be visible through the pupil when in an unstressed (resting) state. This visibility allows the surgeon to easily engage the anchor 2125. When the surgeon engages the fixation arms 2120 by grabbing the body of the fixation arm 2120 or anchor 2125, the surgeon can unfurl the fixation arm 2120 away from the resting, folded configuration in a way to bring it substantially on plane with the posterior platform 2105. These fixation arms 2120 can have a flexibility such that the stresses stored in the material in the deployed state will not impart torsional or tensile forces upon the posterior platform 2105 in a way that compromises device function. The fixation arm(s) 2120 can be molded to have a 90-270 degree turn from its lens support origin in a tangential and centripetal direction. The fixation arm(s) 2120 can incorporate elastic materials or deformable hinges to facilitate this manipulation without substantially altering the geometry of the posterior platform 2105. The fixation arm 2120 can have a length such that when the fixation arm 2120 bends 180 degrees back towards its origin with the posterior platform 2105, the terminal end 2102 of the fixation arm 2120 can be positioned over at least a portion of the posterior platform 2105. Each of the fixation arms 2120 of the device 2100 can have a bend or just a selection of the fixation arms 2120 can have a bend (e.g., one, two, up to less than all fixation arms 120).

The visibility of one or more regions of the device can be improved also by modifying the material of the device components. The device can be formed of silicone elastomer, fluorosilicone elastomer, urethane, flexible acrylic, copolymers or combinations, or other biocompatible elastomers. The material of the device as a whole or one or more distinct regions of the device can be made translucent or opaque for visualization purposes. For example, where the material selected for the fixation arms, anchors, platform, awnings, or other region of the device is normally transparent, one or more additives may be included in the material to make it translucent or opaque. The additive can be a pigment or dye, polymerized or unpolymerized, so that the device or device component is readily visible by a user within the eye. A white pigment or dye added to an otherwise clear silicone elastomer forming the anchor of one or more of the fixation arms 2120 so that they are more easily seen and grasped during externalization. One or more regions of the chassis of the device may also be opaque with a dye or pigment so that the optical element can be manipulated relative to the device with visual confirmation of the location of the optical element components. An IOL haptic, for example, can be positioned behind a tab or awning of the device that is made opaque so that the haptic is not visible following implantation. The size of the anterior opening prevents the opacity of the one or more device features, such as the tab or awning, from significantly impacting a user's vision while the device is implanted.

One or more of the fixation arms 2120 of the devices described herein can be manufactured to have a non-planar geometry at rest and may be biased towards the folded configuration that allows for easy viewing of at least a portion of the fixation arm 2120 through a pupil once the device 2100 is implanted, but prior to externalization of the anchor 2125. The fixation arm 2120 having this configuration can be more easily grasped and manipulated by a user so that it can be urged into an unfolded configuration for sutureless fixation. A fixation arm 2120 manufactured to have a bias in a resting state or that is curved or bent in a resting state includes a fixation arm 2120 having that shape when the device 2100 is outside the eye and ready for implantation. In some implementations, the fixation arm 2120 can take on the curved, folded, or bent shape after implantation in the eye (e.g., the posterior chamber), but before fixation of the anchors. For example, one or more fixation arms 2120 can be formed of a material that has a first shape outside the eye, takes on a curved shape upon implantation in the eye that is different from the shape of the arm 2120 prior to implantation in the eye, and that can be unfolded into a substantially straight shape upon externalization of the anchor 2125.

A fixation arm 2120 that has the bias towards a folded or curved shape (e.g., having a bend along its length between its origin portion 2103 and its terminal end 2102) can be visualized through the pupil, grasped, and manually unfolded and/or stretched to fix the anchor 2125 of the arm 2120 trans-sclerally. The configuration and/or radius of curvature of the curve, bend, or fold as well as the directional orientation of the curve, bend, or fold can vary so long as at least a portion of the fixation arm 2120 (e.g., the anchor 2125 and/or the terminal end portion coupled to the anchor 2125) is visible to a user through the diameter of the pupil of the patient, preferably a dilated pupil of the patient. In some implementations, this means at least a portion of the fixation arm 2120 is positioned over at least a portion of the posterior platform 2105 and radially inward of its outer wall 2111. The distance the portion of the arm 2120 extends radially inward of the outer wall 2111 can vary. The portion can extend to be over a location adjacent to the outer wall 2111 that is not over the outer wall 2111 in the orientation a central axis CA extending anterior-to-posterior through the central opening 2115. In this implementation, the distance between the central axis CA of the device to the portion extending over is greater than the distance between the central axis CA of the device and the outer wall 2111. The portion can extend to be over the outer wall 2111. In this implementation, the distance between the central axis CA of the device to the portion is the same as the distance between the central axis CA of the device and the outer wall 2111. The portion can extend to be over a location radially inward to the outer wall 2111. In this implementation, the distance between the central axis CA of the device to the portion is less than the distance between the central axis CA of the device and the outer wall 2111. The portion can extend to be over the central opening 2115. In this implementation, the distance between the central axis CA of the device to the portion is less than the distance between the central axis CA of the device and the inner wall 2109 defining the central opening 2115.

A portion of the fixation arm (e.g., the terminal end and/or the anchor 2125) can be positioned over a portion of the posterior platform 2105 and at the same time also over a portion of the central opening 115. For example, the anchor 2125 can have a dimension such that at least a portion of the anchor 2125 is positioned over at least a portion of the posterior platform 2105 and another portion of the anchor 2125 is positioned over at least a portion of the central opening 2115.

The fixation arms 2120 biased towards a curved configuration can curve towards an inner or a central portion of the device, including, but not limited to, the actual center of the device or the central axis CA. The center of the device 2100 is the center of the circle formed by the central aperture 2115 (in the instance where the central aperture 2115 is circular). The central axis CA of the device extends through the center of that circle in an anterior-to-posterior direction (i.e., a top-to-bottom direction). If the central aperture 2115 is substantially non-circular, the center of the device is a symmetrical center of the central aperture 2115 along the central axis CA extending anterior-to-posterior direction. A fixation arm that is biased into a folded or curved configuration such that its anchor extends towards a center of the device or towards the central axis CA of the device need not require an axis through the anchor of the arm to intersect the actual center or intersect the central axis CA of the device. "Toward the center" or "toward the central axis" regarding the inwardly biased fixation arms includes an arm having a curve so that the terminal end of the fixation arm extends back toward a portion of the device in a generally inward direction as opposed to the terminal end of the straight fixation arm, which extends in a generally outward direction away from the support structure. The curved fixation arm can be biased toward any central portion of the device and need not point directly at the actual center of the device. The curved fixation arms can be angled relative to the actual center.

Where the fixation arms are described as being "folded" or "bent" or "curved" or having a configuration that is "folded" or "bent" or "curved", the angle of the fixation arms relative to a longitudinal axis along its length can change gradually and uniformly, or can change more sharply or abruptly such that an angle is formed. The folded configuration can describe the inward bias of the fixation arm at rest or prior to implantation where the fixation arm extends outward from the support structure along a first axis and curves anteriorly or posteriorly relative to a plane of the support structure back towards a central portion of the device. The support structure of the device when implanted is configured to lie substantially parallel to the Z-plane (vertical plane) of the eye. The folded configuration can include a geometry in which the fixation arm curves away from this plane of the support structure (e.g., within a transverse plane) so that at least a portion of the fixation arm is positioned anterior to another portion of the device (e.g., over itself, the support structure, and/or the central opening). The folded configuration need not mean the fixation arm portions are over and also in contact with each other. Preferably, the portions of the fixation arm are spaced a distance away from each other, the distance being along the central axis CA of the device. The folded configuration also need not mean a creased or sharply angled folding. The folded configuration can mean a radius of curvature exists between the origin of the fixation arm at the support structure and the terminal end of the fixation arm.

A portion of the arm 2120 that is positioned over at least a portion of the posterior platform 2105 can include that portion being over as well as positioned radially inward of an outer wall 2110 of the posterior platform 2105. The portion of the arm 2120 that is positioned over at least a portion of the posterior platform 2105 can include that portion being positioned radially inward of and over the central opening 2115. In these instances, "radially inward" need not also mean within the same plane. Preferably, the portion of the arm 2120 is positioned over the portion of the support structure within a different plane from the plane of the support structure. The portion of the fixation arm 2120 (e.g., anchor 2125 and/or terminal end 2102) can terminate anterior or posterior to the posterior platform 2105 at a diameter that is central to the outer perimeter of the posterior platform 2105. The portion can be located over the portion of the support structure relative to the central axis CA of the device that extends anterior-to-posterior through the central opening 2115. Where the portion of the fixation arm 2120 is described as being over the portion of the support structure, the portion of the fixation arm 2120 may also be over the central opening 2115 defined by the posterior platform 2105.

Where a portion of the arm 2120 is described herein as being "over" another portion of the device 2100 (e.g., itself, the posterior platform 2105, and/or the central opening 2115), the portion of the arm 2120 can generally overlap that portion of the device in space and need not require a particular direction relative to the retina. Thus, "over" may be used generically herein to refer to an overlap in the space surrounding the device and can, but need not require the spatial overlap to be in a generally anterior direction relative to the retina. A portion that is described as being "over" another portion can, during use, be positioned posterior to it relative to the retina. The arm 2120 that is biased into the folded configuration may only be referred to herein as "over" or "overlapping" another part of the device even though it may also, during use, be positioned "under" or "posterior" to another part of the device relative to the retina. For the sake of simplicity, each alternative may not be reiterated at each instance throughout the disclosure. The arms can be curved to position at least a portion of the arm over an anterior-facing portion of the device such that the portion is generally vaulted above the device along the central axis CA. The arms can be curved to position at least a portion of the arm over a posterior-facing portion of the device such that the portion is generally vaulted below the device along the central axis CA. The arms can be curved to position at least a portion of the arm within the same plane so that it is neither over the anterior-facing portion nor over the posterior-facing portion of the device. Any of a variety of configurations of the fixation arms are considered herein so that at least a portion of the arms are visible through a dilated pupil. The mechanisms can vary by which the bent fixation arms 2120 that are biased towards the folded configuration become unfolded to take on a straight configuration. The arms can be unfolded mechanically, electromagnetically, and/or thermally.

In some implementations, the fixation arm 2120 may be unfolded mechanically along a single axis of the arm. The fixation arm 2120, at rest, need not be biased into a folded configuration that has a bend or that curves. For example, the fixation arm 2120 may be biased into a folded configuration in which the arm 2120 is compressed longitudinally along a single axis. The arm 2120 be extend along the single axis orthogonally outward from the support structure between its origin portion 2103 and its terminal end portion 2102. The length of the arm 2120 in the folded configuration can be shorter between origin portion 2103 and terminal end portion 2102 such that the anchor 2125 of the arm 2120 is positioned more centrally within a smaller diameter than when in the unfolded configuration. Once the device is implanted in the eye, but before externalization of the anchor 2125, the arm 2120 may be telescoped outward to extend its length such that it can be externalized. The mechanical unfolding by telescoping can be due to nested components of the arm 2120 sliding over each other to provide greater length when unfolded or a shorter length when folded. The mechanical unfolding by telescoping can also be due to a single clastic component configured to fold into itself for a shorter length for visualizing through the pupil and unfold out of itself for a longer length during externalization.

In some implementations, the fixation arm 2120 may be unfolded or folded thermally. For example, the fixation arm 2120 can be in a first shape at room temperature (folded or straight) and change to a second shape at body temperature or thereabouts (heated to 35° C.). This can also be effected by chemical means (e.g., hydration) or mechanical means (cutting a restrictive feature).

The fixation arm 2120 can be produced from elastic or inelastic material. For example, the fixation arm 2120 can be formed of an inelastic material and have a 3-dimensional shape that provides for the elasticity. The 3-dimensional shape can vary as described elsewhere herein, including a C-shape, Z-shape, S-shape, or other 3-dimensional shape. The fixation arm 2120 provides sufficient support to maintain an IOL 110 or other device while not imparting excessive force on scleral tissue. An optimal design would have a wide operable range of tensions and stability in order to be able to meet both parameters in eyes of varying sizes and with incisions in varying locations. One means of modifying the fixation arm design is to incorporate spring-like structures. These can include traditional compression based haptic designs like J-Loop, C-Loop, Closed Loop, Kellman Haptics, plate haptics, or other haptic designs common to IOLs. Alternatively, the device 2100 can incorporate a tension-based haptic such as a simple linear elastic cord. Alternatively, the tension design can be modified with a V-shaped, Z-shaped or S-shaped feature to decrease the tensile resistance of the fixation arm 2120.

The fixation arm 2120 can have a texture or features that allows it to be pulled through sclera in one direction, but there is resistance in the opposite direction to minimize the chance of slippage the fixation arm 2120. The texture or feature can be provided by the material itself or designed into the fixation arm 2120. For example, the fixation arm 2120 can be barbed and formed from a material integrated into an outer structure. In this way, a barbed internal structure may be able to function as a barb while hiding the sharp edges commonly associated with a barb. An example would be a rigid plastic structure embedded in a soft elastomeric structure.

The fixation arms 2120 can be formed of a flexible material that has memory and is not malleable. The flexible material of the fixation arms 2120 can include any of a variety of biocompatible elastomers including silicone elastomer, fluorosilicone elastomer, urethane, flexible acrylic, copolymers or combinations, polyurethanes, hydrophobic acrylics, hydrophilic acrylics, Nylon, Polyimide, PVDF, natural polyisoprene, cis-1,4-polyisoprene natural rubber (NR), trans-1,4-polyisoprene gutta-percha, synthetic polyisoprene (IR for isoprene rubber), Polybutadiene (BR for butadiene rubber) Chloroprene rubber (CR), polychloroprene, Neoprene, Baypren etc., Butyl rubber (copolymer of isobutylene and isoprene, IIR), Halogenated butyl rubbers (chloro butyl rubber: CIIR, bromo butyl rubber: BIIR), Styrene-butadiene Rubber (copolymer of styrene and butadiene, SBR), Nitrile rubber (copolymer of butadiene and acrylonitrile, NBR), also called Buna N rubbers Hydrogenated Nitrile Rubbers (HNBR) Therban and Zetpol, EPM (ethylene propylene rubber, a copolymer of ethylene and propylene) and EPDM rubber (ethylene propylene diene rubber, a terpolymer of ethylene, propylene and a diene-component), Epichlorohydrin rubber (ECO), Polyacrylic rubber (ACM, ABR), Silicone rubber (SI, Q, VMQ), Fluorosilicone Rubber (FVMQ), Fluoroclastomers (FKM, and FEPM) Viton, Tecnoflon, Fluorel, Aflas and Dai-El, Perfluoroelastomers (FFKM) Tecnoflon PFR, Kalrez, Chemraz, Perlast, Polyether block amides (PEBA), Chlorosulfonated polyethylene (CSM), (Hypalon), Ethylene-vinyl acetate (EVA), Thermoplastic elastomers (TPE), resilin and elastin, Polysulfide rubber, and Elastolefin.

The arms 2120 made of a flexible material that is formed into a shape can be flexed away from the formed shape, but has memory to return to the formed shape. In other words, the flexible fixation arms 2120 can be flexed or unfolded away from their folded configuration, but cannot be urged into a different shape that is retained without some kind of anchoring fixation. For example, one or more of the flexible fixation arms 2120 can be formed into a bent shape. For example, the arm can include a 180 degree bend from its origin 2103 with the posterior platform 2105 to the terminal end 2102 near the anchor 2125. The arm 2120 can maintain this bent shape when the device is at rest and no forces are applied to the arm 2120 such that the arm 2120 is biased towards a folded configuration. In other words, the arm 2120 in its unbiased state is bent. The bent fixation arm 2120 can be flexed away from this bent shape to take on a straight shape or an unfolded configuration such that the entire arm 2120 extends and is positioned straight relative to the longitudinal axis L. When flexed into a straight shape, the arm 2120 is biased to return to the bent shape or the folded configuration. If the flexing force on the fixation arm 2120 is released, the arm 2120 will return to its resting bent shape. However, when in use, the fixation arm 2120 is anchored trans-sclerally and the anchor 2125 at the terminal end 2102 of the arm 2120 positioned outside the sclera. The arm 2120 is tensioned to remain in the straight shape.

The one or more fixation arms 2120 can have a Young's modulus that is less than about 1000 MPa, or less than about 500 MPa, or less than about 250 MPa, or less than about 100 MPa, or less than about 50 MPa, or less than about 25 MPa. The one or more fixation arms 2120 can have a Young's modulus that is less than about 20 MPa, for example, between about 0.01-about 1.0 MPa, or between about 0.5-about 5.0 MPa. The fixation arms 2120 can be very soft and apply very little force because they are designed to be under tension to anchor the posterior platform 2105 rather than having a compression spring force to anchor the posterior platform 2105 or a more rigid penetrating force that a barb or other fixation haptic can provide.

In some implementations, the fixation arms 2120 can each have a length between the origin 2103 and the terminal end 2102 that is about 2 mm to about 6 mm. The fixation arms 2120 each can have the same length or can have different lengths from one another. The length of the fixation arms 2120 that extends through the sclera can having a thickness or width that is minimized to reduce the overall size of the wound through which the arms 2120 extend. The maximum width of the trans-scleral portion of the fixation arms near the terminal end 2120 where the anchor 2125 is positioned can be no greater than about 2.0 mm, no greater than about 1.5 mm, no greater than about 1.0 mm, no greater than 0.75 mm, no greater than 0.50 mm.

FIGS. 1A-1D and FIG. 2A show implementations of a device 2100 having two fixation arms **2120*a*, 2120*b* that have inward bias and a third fixation arm 2120*c* that does not have inward bias and is straight. Additionally, the third fixation arm 2120*c* has a geometry that makes it less flexible than the other fixation arms 2120*a*, 2120*b*. The third fixation arm 2120*c* can incorporate a region between the origin 2103 and terminal end 2102 that is wider than the other two fixation arms 2120*a*, 2120*b* and can have a higher cross-sectional area. A region of a fixation arm 2120 can be narrower near the terminal end 2102 and wider away from the terminal end 2102 of the arm 2120. The width of the arm 2120 away from the terminal end 2102 can provide a degree of bulk and stability while the width near the terminal end 2102 can minimize the trans-scleral portion of the arm 2120**.

Each fixation arm **2120*a*, 2120*b*, 2120*c* can be positioned one at a time during the surgical procedure. As described elsewhere herein, the leading fixation arm 2120*c* can be a straight configuration and the trailing fixation arms 2120*a*, 2120*b* can be curved. The weight of the device can cause the first implanted or leading fixation arm 2120*c* to bend following externalization such that the device 2100 tilts posteriorly toward the retina. In this scenario, a surgeon can locate the device in a more posterior position. However, this can increase the risk of intraoperative tissue damage due to the manipulation of tools near the retina. In some implementations, the leading fixation arm 2120*c* can be mechanically and/or geometrically reinforced to reduce the likelihood of posterior drift. The leading fixation arm 2120*c* can be produced out of a material that is resistant to such deformation. The material can be any implant grade plastic or metal that can cantilever the device following externalization of the anchor 2125 of the leading fixation arm 2120*c*. Suitable materials include, but are not limited to, PMMA, rigid silicones, nylon, hydrophilic and hydrophobic acrylics, PEEK, polyimide, stainless steel, titanium, Nitinol, and others. The more rigid material can be used to form the entire leading fixation arm 2120*c* or just a portion of the leading fixation arm 2120*c*. The leading fixation arm 2120*c* may be formed of a softer material embedded with a more rigid material. In an implementation, the leading fixation arm 2120*c* can include a region of mechanical reinforcement between its origin 2103 at the posterior platform 2105 and its terminal end 2102 where it is coupled to an anchor 2125. The region can achieved by increasing a thickness of the fixation arm 2120*c* or embedding a rigid section of plastic into a softer material. The region can have an increased thickness designed to specifically reduce the likelihood that the device 2100 drifts posteriorly, while not impacting the ability externalizing the anchor 2125 of the fixation arm 2120. For example, the fixation arm 2120 can have a tapered thickness designed to limit deflection in the posterior direction. The tapered geometry can be thinnest near the footplate anchor 2125 and thicken centrally. The posterior surface of the fixation can serve to bias the device anteriorly relative to the eye. The angle of contact of the posterior surface of the fixation arm 2120 and the wound can bias the device 2100 in a way that reduces the practical risk of a posterior deflection of the fixation arm 2120**. Additional bulk can further limit the deflection of the device and the proximity to the retina.

The trans-scleral fixation arm 2120 and/or anchor 2125 can have a photoreactive or hydroreactive element that assists in the sizing or fixation of the fixation arm. By swelling or shrinking a portion of the fixation arm, the geometry of the fixation arm can be expanded or contracted to intra-operatively or post-operatively adjust the length of the fixation arm. Alternatively, by expanding the anchor following the externalization of the fixation arm, the anchor will become more effective in providing secure fixation with reduced risk of slippage.

The cross anchor of the fixation arm can slide along the fixation arm 2120 with some resistance. By adjusting the fixation arm 2120 intraoperatively, the surgeon can size the device 2100 specifically for a given patient. Custom sizing reduces the risk of slippage and modulation of the effective lens position. Once the fixation arm 2120 is set to the appropriate tension, the excess material can be removed such as by trimming.

The device 2100 can be made of a material or contain a geometry that can serve as a drug delivery device, including a refillable drug delivery device. A securely fixated device accessible in the subconjunctival space would provide an opportunity to deliver drugs to the posterior and anterior segments. Examples of therapeutics can include one or more drugs for lowering intraocular pressure (glaucoma medications), steroids, biologic medications such as anti-vascular endothelial growth factor (anti-VEGF), gene therapy, anti-bacterial, anti-viral, chemotherapeutic, and non-steroidal anti-inflammatory medications, among others to treat ocular or systemic diseases.

The devices described herein can be used together with IOLs having any of a variety of conventional designs, including multi-piece as well as one-piece designs. IOL 110 can include a central optic 112 and two haptics 114 (sec, e.g., FIGS. 1B and 1C). The haptics 114 can be conventional open loop haptics such as C-loop, J-loop, modified J-loop, or other haptics. The IOL 110 may be positioned above (or below) the central opening 2115 of the device so that the central axis CA extending anterior-to-posterior through the central opening 2115 extends through the optic 112 of the IOL 110. The haptics 114 of the IOL 110 may project upwards or anteriorly away from (or toward, if positioned below) the posterior platform 2105 as described elsewhere herein. One-piece IOLs can have open loop haptics similar to conventional three-piece IOLs do. One-piece IOLs may also incorporate monobloc-plate style haptics. Where the device is shown with one type of IOL (e.g., the multi-piece IOLs or one-piece IOL shown in FIGS. 1B and 1C), it should be appreciated that another type of IOL can be mated with the device. The devices described herein can be used with any type of IOL as described elsewhere herein, including multi-piece as well as one-piece designs. Similarly, the haptics of the IOL can be of any of a variety of configurations. Other sorts of implants having an optical element can incorporate a haptic system to ensure fixation within an eye, including, for example, IMTs. The devices described herein can be used together with any of a variety of implants having haptic designs.

The posterior platform 2105 can have a geometry adapted to mate with a perimeter of the optical element or with one or more haptics of the optical element. The geometry can include a concavity, recess, channel, or groove forming at least a portion of an inner perimeter of the support structure.

The posterior platform 2105 can support the IOL 110, for example, taking the place of a native lenticular capsular bag. The device 2100 can include one or more leaflets or awnings 2126 positioned over an anterior-facing surface of the posterior platform 2105 so that one or more recesses 2104 are formed within which at least a portion of the IOL 110 may be positioned. The recesses 2104 may at least partially surround the central aperture 2115 and be sized to accommodate at least a portion of the IOL, such as the haptics 114. FIGS. 1B and 1C show the IOL 110 engaged with the device 2100. The optic 112 of the IOL 110 is positioned over the central opening 2115 and a perimeter region of a posterior-facing surface of the optic 112 is positioned against the anterior-facing surface of the posterior platform 2105. Each of the haptics 114 of the IOL 110 can be positioned substantially within the respective recesses 2104 and a majority of the optic 112 of the IOL 110 remains outside the recesses 2104. The recesses 2104 can be defined by an anterior-facing surface of the posterior platform 2105 and the overhanging leaflet or awning 2126. The volume of the recesses 2104 formed by the space between the anterior-facing surface of the posterior platform 2105 and the posterior-facing surface of the awning 2126 is sufficient to receive the respective one of the haptics 114 in both depth anterior-to-posterior as well as distance away from the central axis CA of the opening 2115. The awnings 2126 can have a smooth geometry and can serve to protect the iris from any sharp edges of the IOL once positioned on the device 2100. Additionally, the central-facing surfaces of the awnings 2126 (facing toward a center axis CA of the device 2100) can additionally serve to provide a surface against which the haptics 114 may abut. These surfaces can provide counter pressure to the haptics and thereby aid in centering the IOL 110 on the device 2100. The awnings 2126 also can limit Z-axis movement of the haptics 114 and help to secure the IOL 110 to the device 2100. The reliable fixation of the IOL, including one-piece IOLs, allow for the use of IOLs that require tight centration tolerances (e.g., torics, multi-focal lenses, extended depth of focus (EDOF) IOLs, and accommodating IOLs).

The IOL 110 may be positioned within the device 2100 prior to implantation in the eye or after implantation in the eye. Similarly, the IOL 110 may be removed from the device 2100 and replaced postoperatively. In some implementations, the IOL 110 is pre-loaded within the device and the loaded device injected into the eye using an IOL injector. The devices can be assembled together within the operating room and injected together or the devices can be injected separately and mated once inside the eye. Methods of implantation of the device will be described in more detail below.

Figure 1D:
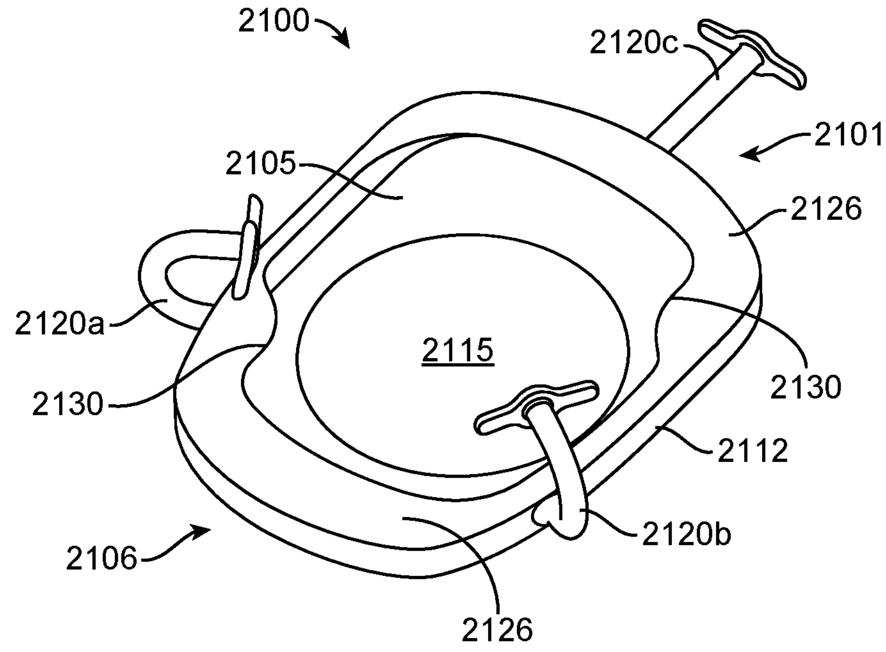
FIG. 1D shows an interrelated implementation of the device of FIGS. 1A-1C.

The device 2100 can have an outer perimeter 2111 that has a major axis and a minor axis. Thus, the inner perimeter 2109 may define a circular central aperture 2115 and the outer perimeter 2111 may define a non-circular shape. The recesses 2104 formed by the awnings 2126 are positioned opposite one another relative to the major axis so that the span of the IOL 110 haptics 114 may be accommodated within the recesses 2104. The non-circular outer perimeter 2111 in FIGS. 1A-1D is a rounded rectangle. Where a shape is referred to here as being "rectangular" it should be appreciated that the shape need not have corners that form right angles or that the sides be perfectly parallel with one another. The term is used to suggest a particular non-circular shape that is elongate having a pair of opposing sides that are longer than a pair of opposing ends to have a major or long axis and a minor or short axis. The rounded rectangle or stadium shape may have two substantially flat or slightly curved, elongate sides 2108 and two substantially rounded, short sides or lobes 2107. The shape of the outer perimeter wall can be symmetrical along each line of symmetry that would be present in the geometric shape. For example, a stadium shape or rounded rectangle geometrically includes two lines of symmetry due to the opposing sides being parallel and the opposing ends being identical. However, the opposing sides of a stadium shape device need not be parallel and the opposing ends can have a slightly altered shape compared to one another. The opposing elongate sides 2108 of the device can be non-parallel so that the trailing end 2106 of the stadium shaped device is narrower than the opposite leading end 2101 of the device (see FIG. 2F). The outer perimeter 2111 of this stadium shaped device would not be symmetrical along one of two lines of symmetry that would normally be present in a rectangle or stadium shape. The elongate sides 2108 of the rounded rectangle or stadium shaped perimeter need not be parallel. FIG. 2F shows elongate sides 2108 that bow outward slightly along their length such that they are not perfectly parallel as are dotted lines P, P'. The elongate sides 2108 intersect the parallel lines P, P' near the trailing end 2106 of the device and diverge out from parallel lines P, P' moving toward leading end 2101. FIG. 2F illustrates a footprint of a device highlighting a shape of its outer perimeter 2111. It should also be appreciated that other features of the device such as the awnings, haptic covers, and fixation arms can impact the lines of symmetry as well. In some embodiments, the device as a whole (including awnings, haptic covers, and fixation arms) has no line of symmetry.

The recesses 2104 formed by the awnings 2126 may project out over the anterior-facing surface of the posterior platform 2105 such that they are positioned generally opposite one another along a major axis of the rectangle and spaced to accommodate the span of the IOL 110 haptics 114. For example, the awnings 2126 may project out over the anterior-facing surface of the posterior platform 2105 on the short sides of the rounded rectangle (i.e., at the location of the lobes 2107) to accommodate the span of the IOL therebetween within the recesses 2104 along the long sides 2108.

Although the span of the recesses 2104 can accommodate the span of the IOL haptics 114, the span of the recesses may be slightly undersized compared to the span of the IOL haptics 114 so that the haptics 114 are placed under slight compression by the inner bearing surfaces of the side walls 2112. The IOL 110 can rest in a position relative to the device 2100 such that the haptics 114 are at least partially flexed. If the haptics 114 are flexed too severely due to the fit being too tight, the optic 112 of the IOL 110 can become distorted. If the haptics 114 are not in contact with the side walls 2112 due to the fit being too loose, the optic 112 of the IOL 110 may not be stable relative to the device such that it shifts and/or falls out of the device 2100. The one or more recesses 2104 can be sized to accommodate at least a portion of the IOL 110, for example, along as a thickness aspect within the Z-axis), as an arc length to provide wiggle room for IOL rotation relative to the device 2100 during implantation, or as a width providing a degree of coverage to hide the haptic edge from contacting the iris. The depth of the recesses 2104 between an inner surface of the awnings 2126 and the anterior-facing surface of the platform 2105 can be between about 0.05 mm and about 1.50 mm. The width across the platform 2105 between side walls 2112 along the minor axis can be between about 5.0 and about 11.0. The span between opposing recesses 2104 can be between about 7.5 mm and about 12.5 mm. In another implementation, the length of the platform is about 10.2 mm, the width is about 7.0 mm, and the depth is about 0.60 mm. In further implementations, the platform along the long axis of the device can have an external length of about 9.2 mm and an internal length along the same axis that is about 8.5 mm such that a thickness of the side wall is about 0.7 mm. In still further implementations, the platform along the long axis can be increased to about 11 mm and an internal length along the same axis that is about 9.8 mm. As a result, the side wall is thicker at about 0.6 mm on each side or a 1.2 mm delta when both sides are counted. The thickness of the side walls 2112 can be uniform around the perimeter of the device or can vary in thickness as will be discussed in more detail below. The increased cavity length can provide more space within which the IOL can be manipulated that, combined with the increased side wall thickness, provides an overall length of the device that is increased. The device can be fixated through the pars plana and thus, posterior to the apex of the ciliary body, such that even if the device on the plane of the ciliary apex is too wide, there can still be space for implanting the larger IOL housing (see FIG. 2D).

Figure 3A:
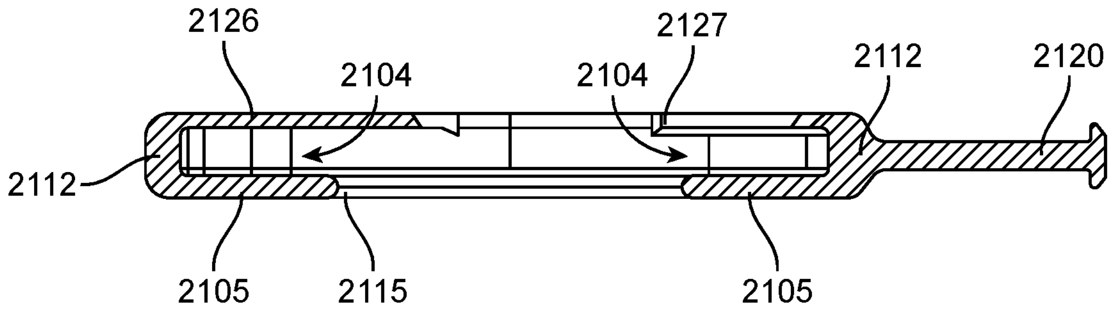
FIGS. 3A-3C are cross-sectional side views of various devices showing different anterior-to-posterior positions of a fixation arm relative to the chassis of the device.
Figure 3B:
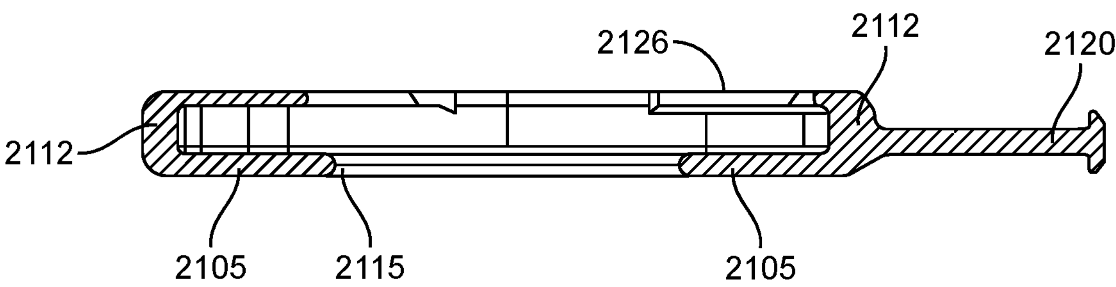
Figure 3C:
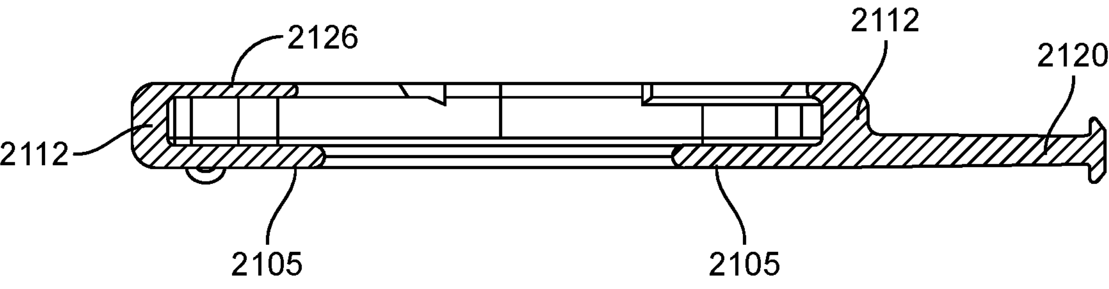

Three fixation arms 2120 can be coupled to a region of the device such as the posterior platform 2105 or region of the device that is located more anteriorly than the posterior platform 2105 such as a portion of the side wall 2112. FIGS. 3A-3C are cross-sectional views of a device illustrating different anterior-to-posterior positions of a fixation arm 2120 relative to the chassis side wall 2112. FIG. 3A shows the arm 2120 extending from location of the side wall 2112 that is generally centrally such that one half of the device projects anterior to the arm 2120 and one half of the device projects posterior to the arm 2120. FIG. 3B shows the arm 2120 extending from location of the side wall 2112 that is generally more posterior such that the portion of the device that projects anterior to the arm 2120 is greater than the portion of the device that projects posterior to the arm 2120. FIG. 3C shows the arm 2120 extending from a most posterior region of the device. The arm 2120 is shown extending from the posterior platform 2105 such that a majority of the device projects anterior to the arm 2120. The more posterior position of the fixation arm 2120 stabilizes the device reducing Z-axis deformation when the fixation arms 2120 of the device are placed under maximum tension. Each of the fixation arms 2120 on the device can be positioned relative to the side wall 2112 at a similar anterior-to-posterior location. In some implementations, the leading fixation arm 2120*c* that is not bent may be positioned at a different anterior-to-posterior location compared to the anterior-to-posterior location of the trailing fixation arms 2120*a*, 2120*b*. For example, the leading fixation arm 2120*c* may be positioned more posteriorly on its side wall compared to the trailing fixation arms 2120*a*, 2120*b* or vice versa.

At least one of the fixation arm 2120*a*, 2120*b* can be biased into the folded configuration as described elsewhere herein. One fixation arm 2120*c* can be a leading fixation arm that extends along a single axis orthogonally relative to the posterior platform 2105 so that its terminal end 2102 coupled to the anchor 2125 projects outward away from the center axis CA of the aperture 2115. The leading fixation arm 2120*c* can be coupled to the posterior platform 2105 at a location of a lobe 2107 and the other fixation arms 2120*a*. 2120*b* can be coupled away from the lobe 2107 of the leading fixation arm, for example, on opposite elongate sides 2108 so that the opposite short lobes 2107 projects outward between the arms 2120*a*, 2120*b* (see FIGS. 1A-1B and 1D). This arrangement can create an overall tapered shape to the posterior platform 2105 from leading end to trailing end, with the trailing end of the platform 2105 somewhat narrower than the leading end of the platform 2105. FIG. 1D shows the posterior platform 2105 and awnings 2126 forming a chassis having a rectangular shape that has a leading end 2101 and a tapered trailing end 2106. The trailing end 2106 of the chassis between the trailing fixation arms 2120*a*, 2120*b* may be narrower than a width of the leading end 2101 of the chassis near the leading fixation arm 2120*c*. The trailing end 2106 of the chassis can be at least about 0.2 mm, about 0.3 mm, about 0.4 mm, about 0.5 mm, about 1.0 mm, about 1.5 mm, about 2.0 mm narrower than a width of the leading end 2101 of the chassis.

The non-circular shape of the outer perimeter 2111 may have a plurality of lobes 2107 projecting outward from a plurality of elongate sides 2108 as described elsewhere herein. Each of the three fixation arms 2120 can extend outward from a respective one of the plurality of elongate sides 2108. The awnings 2126 may project out over the anterior-facing surface of the posterior platform 2105 such that they are positioned generally opposite one another. A first awning 2126 may be positioned near, for example, an origin 2103 of the leading fixation arm 2120*c* and a second awning 2126 may be positioned on a lobe 2107 between the other two fixation arms 2120*a*. 2120*b*. The span of the recesses 2104 defined by the awnings 2126 and the posterior platform 2105 is sufficient to accommodate a span of the IOL haptics 114 therebetween (see FIG. 1C).

The central opening 2115 may have a diameter as described elsewhere herein so that the optic 112 of the IOL may be supported on the anterior-facing surface of the posterior platform 2105 without the optic 112 slipping through its diameter (e.g., between about 4 mm up to about 6 mm). The IOL may be inserted within the recesses 2104 under the awnings 2126. Thus, the diameter between the first and second opposing awnings 2126 is sufficient for IOL insertion. IOLs are typically foldable and therefore the diameter between the first and second awnings 2126 can vary widely. In some implementations, the opposing awnings 2126 are fully connected to one another along the elongate sides 2108. The opposing awnings 2126 can include extensions along each of the elongate sides 2108 forming a complete overhanging surface above the posterior platform 2105 that defines an upper aperture 2127. The upper aperture 2127 can have a diameter that is larger than a diameter of the central aperture 2115 of the posterior platform 2105. For example, the upper aperture 2127 can be greater than about 6 mm so that the IOL can be manipulated into place and fully unfurl into position with the recesses 2104. The diameter of the upper aperture 2127 can be greater than 6 mm up to about 8 mm. The central aperture 2115 is preferably circular, but the anterior opening 2127 need not be circular. The anterior opening 2127 can have any of a variety of geometric or free-form shapes. In some implementations, the anterior opening 2127 can incorporate one or more out-croppings configured to extend over and cover selected areas of the IOL 110, as described in more detail elsewhere herein. The anterior opening 2127 can also incorporate one or more centrally-extending features to directly visualize the device 2100 through the pupil during implantation even if the pupil narrows in size mid-surgery. The centrally-extending features can project to define at least one narrower diameter around the circumference of the anterior opening 2127 that is less than about 7 mm down to about 5 mm, preferably about 6 mm.

The IOL 110 may be positioned against the posterior platform 2105 above the central aperture 2115 so that the central axis CA extending anterior-to-posterior through the central aperture 2115 extends through the optic 112 of the IOL 110. Light is permitted to pass through the aperture 2115 as well as the IOL 110 positioned on the posterior platform 2105. The central aperture 2115 can be substantially co-axial with the optical axis of the IOL 110 once the IOL is positioned against the posterior platform 2105. The central aperture 2115 has a diameter sized to allow the optic 112 of the IOL to be supported on the anterior-facing surface of the posterior platform 2105 without the IOL 110 falling through into the posterior chamber. The diameter of the central aperture 2115 avoids the posterior platform 2105 from overlapping substantially with the optic 112 of the IOL 110 so that it allows light to pass through the device without any optical disturbance as it passes towards the retina. The diameter of the aperture 2115 is designed to be generally universal for a wide range of IOL types. Conventional IOLs typically have optics with an outer diameter of 6 mm although this size can vary depending on the IOL. A central aperture 2115 having a diameter that is less than 5.0 mm down to about 4.0 mm, preferably about 4.75 mm, can be used with some IOLs. A central aperture 2115 having a diameter that is between 5.0 mm to about 6.0 mm can be used with most IOLs such that the device is nearly universal for use with any conventional haptic-stabilized IOL. The minimum inner diameter of the aperture 2115 can be greater than about 3.0 mm, greater than about 3.5 mm, greater than about 4.0 mm, greater than about 4.5 mm, greater than about 5.0 mm, greater than about 5.5 mm, greater than about 6.0 mm, greater than about 6.5 mm, up to about 7.0 mm, up to about 8.0 mm, up to about 9.0 mm, up to about 10 mm, up to about 15 mm, and any range in between. The central aperture 2115 inner diameter can be between about 4 mm to about 8 mm, or between about 4 mm up to 6 mm. The inner diameter of the central aperture 2115 can approach the outer diameter of a common IOL optic 112, for instance at least about 5.5 mm or 6.0 mm. In an implementation, the minimum inner diameter of the aperture 2115 can be small enough to create a pin-hole effect to create an extended depth of focus. In this implementation, the inner diameter of the aperture 2115 can be less than about 3.0 mm down to about 1.5 mm, including 2.0 mm and 2.5 mm inner diameter.

The aperture diameter can be selected to maintain a particular hoop strength to limit the risk of accidentally passing the IOL through the aperture 2115 upon implantation. Smaller aperture diameters can increase the hoop strength compared to larger aperture diameters. A stiffer chassis or housing limits distortion of the aperture 2115 when placed under tension and/or compression. The increased stiffness of the IOL housing can also facilitate easier insertion of the IOL following fixation in the eye. In other implementations, the implant preferably extends at least in part through the aperture 2115 when positioned within the device. In these implementations, the aperture 2115 is prevented from distortion while mated with the implant even though the aperture 2115 may undergo some distortion during insertion of the implant through or into the aperture 2115. Regardless, the configuration, once the implant and the device are positioned relative to one another and relative to the eye anatomy, the aperture 2115 and other parts of the device supporting the implant are generally stiff enough to prevent distortion and undergoing changes in shape that would negatively impact the patient's visual quality through the optical element(s) of the system.

The posterior support structure or platform 2105 of the device 2100 can have an anterior-facing, support surface directed towards a front of the eye when the platform 2105 is in use and a posterior-facing surface directed towards a back of the eye against the capsular bag when the platform 2105 is in use. The posterior platform 2105 can provide several functions. The posterior platform 2105 can have a surface (the anterior-facing surface or posterior-facing surface) forming a stable platform against which an IOL 110 can be placed during use. The posterior platform 2105 can take the place of a capsular bag and can set the effective lens position of the IOL 110 within the eye. The geometric and mechanical function of the posterior platform 2105 not only supports the IOL 110 when in use, it can also serve to assist in the centration of an IOL 110 in the case of an asymmetric eye or asymmetric surgical procedure. The posterior platform 2105 provides artificial anterior capsule support for the IOL and a stable platform structure in the eye recapitulating the native anterior capsule. The posterior platform 2105 can be substantially flat or planar between the anterior-facing surface and the posterior-facing surface. The thickness of the posterior platform 2105 between the anterior-facing surface and the posterior-facing surface can be minimized while still providing sufficient support to the IOL. The thickness can be between about 0.02 mm and 1.5 mm, or between about 0.5 mm and 1.0 mm. The posterior platform 2105 can be about 0.2 mm. The thickness of the posterior platform 2105 can be thinner than 0.2 mm and still provide sufficient support for an IOL. For example, the posterior platform 2105 can be reinforced with a stiffer material to reinforce it and limit its distortion despite being only 0.2 mm thick. Alternatively, the posterior platform 2105 can have an increased thickness (e.g., about 0.50 mm up to about 1.0 mm) and the material thickness sufficient to limit distortion of the device even when placed under tension and/or compression. Increased stiffness of the support structure can facilitate easier insertion of the IOL following implantation. This can additionally increase the hoop strength of an aperture 2115 extending through the posterior platform 2105 as described in more detail below, which can limit the risk of the IOL accidentally passing through the aperture 2115 upon implantation of the IOL in the device 2100. Reinforcement of the devices described herein to avoid distortion and risk of the IOL passing through the device is discussed in more detail below. In some implementations, a central region of the device defining the aperture 2115 may have a greater thickness than a perimeter region of the device such that the region supporting the implant is prevented from distortion and inadvertent tilt of flip of the implant being supported. For example, an IMT may be inserted at least partially through the aperture 2115 and supported by a thicker central region of the device that is shaped to mate with a corresponding waist of the IMT (see FIGS. 10C-10D).

Figures 2A, 2B, 2C:
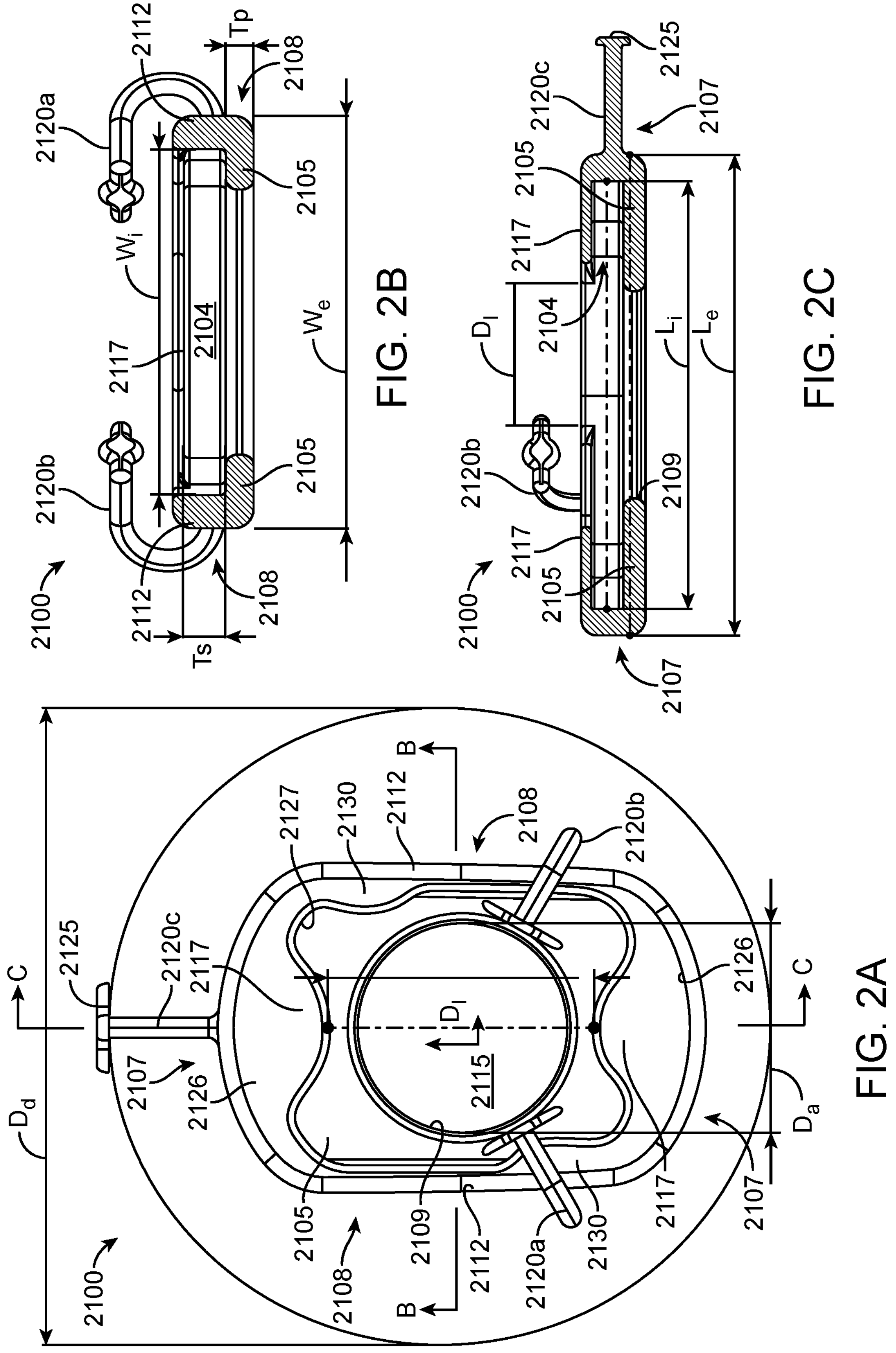
FIG. 2A shows a top-down view of an interrelated implementation of the device incorporating a plurality of transscleral fixation arms.
FIG. 2B shows a cross-sectional view of the device of FIG. 2A taken along line B-B.
FIG. 2C shows a cross-sectional view of the device of FIG. 2A taken along line C-C.
Figure 2D:
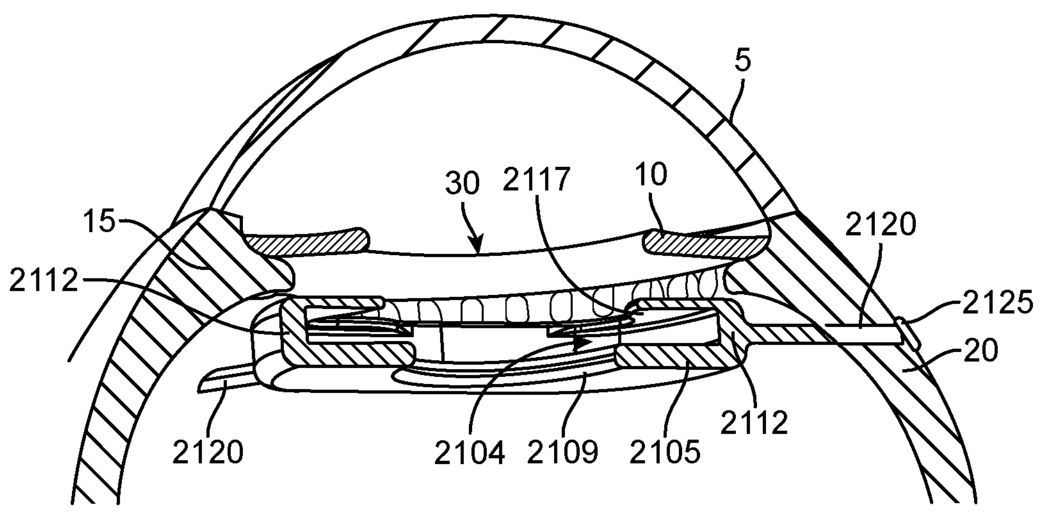
FIG. 2D shows the device of FIG. 2C implanted in an eye.

FIGS. 2A-2C illustrate an implementation of the device 2100 incorporating a plurality of fixation arms 2120. The posterior platform 2105 and the side walls 2112 can be reinforced due to increased material thickness of those regions of the device. FIG. 2B is a cross-sectional view of the device 2100 in FIG. 2A taken along arrow B-B showing an increased cross-sectional thickness Tp of the posterior platform 2105 (e.g., about 0.50 mm) and an increased thickness Ts of the side wall 2112 (e.g., about 0.35 mm up to about 0.60 mm or up to about 1.5 mm). The increased stiffness of the support structure provided by the increased material thickness can facilitate easier insertion of the IOL following implantation. The increased material thickness can additionally increase the hoop strength of the central aperture 2115 extending through the posterior platform 2105, which can limit the risk of the IOL accidentally passing through the aperture 2115 upon implantation of the IOL in the device 2100.

The diameter $D_a$ of the central aperture 2115 also can be reduced to increase the hoop strength of the posterior platform 2105. For example, the central aperture 2115 can have a diameter that is less than about 5.0 mm down to about 4.0 mm, preferably about 4.75 mm so as not to interfere with the optics of the IOL. As discussed elsewhere herein the material of one or more regions of the device can be translucent or opaque for visualization purposes. A platform 2105 that is non-transparent would interfere with the optics of the IOL unless it incorporated a central aperture 2115 to allow light to pass through the IOL unhindered. Thus, the central aperture 2115 is selected to have a size that is large enough to prevent significant interference, but small enough to support the IOL and prevent the optic from falling through the aperture 2115.

The aperture size alone or in combination with the posterior platform thickness and/or side wall thickness can resist distortion of the device that could otherwise be caused by the tensioned fixation arms. The aperture diameter can also limit the risk of accidentally passing the IOL through the aperture 2115 upon implantation due to not just the size, but the increased hoop strength of the aperture 2115. Smaller aperture diameters can increase the hoop strength compared to larger aperture diameters. A stiffer IOL housing limits distortion of the aperture 2115 when placed under tension and/or compression. The increased stiffness of the IOL housing can also facilitate easier insertion of the IOL following fixation in the eye.

The thicker side walls 2112 of the device can reduce the space within which the IOL can be manipulated. To provide more space for IOL manipulation within the recess 2104, the external length along the long axis of the device can be increased to accommodate the thicker side walls 2112 and provide an internal length of the recess along the same axis for IOL insertion and manipulation (see FIG. 2C). The posterior platform 2105 along the long axis of the device can have an external length Le of about 9.2 mm and an internal length Li along the same axis that is about 8.5 mm such that a thickness of each side wall is about 0.35 mm. To provide additional reinforcement to the device 2100, the side wall cross-sectional thickness can be increased to about 0.60 mm. The platform along the long axis can be increased to about 11 mm such that an internal length Li along the same axis is about 9.8 mm. The increased cavity length can provide more space within which the IOL can be manipulated that, combined with the increased side wall thickness, provides an external length Le of the device that is increased. The longer device can be fixated through the pars plana and thus, posterior to the apex of the ciliary body, such that even if the device on the plane of the ciliary apex is too wide, there can still be space for implanting the larger IOL housing (see FIG. 2D). The short axis width can be impacted by the thicker side walls 2112 as well (see FIG. 2B). The posterior platform 2105 along the short axis of the device can have an external width We of about 6.60 mm and an internal width $W_i$ along the same axis that is about 5.90 mm such that a thickness of each side wall 2112 is about 0.35 mm. Each side wall 2112 cross-sectional thickness can be increased to 0.60 mm as discussed above. The platform 2105 along the short axis can be increased to about 7.4 mm such that an internal Width $W_i$ along the same axis is about 6.2 mm.

The devices described herein are used to support an optical element, such as an IOL, within an eye. The devices described herein can incorporate one or more features configured to engage with at least a portion of the capsular bag, if present, for centration or fixation in the eye. The devices described herein can incorporate one or more features configured to fix and center the device in the eye even where capsular bag support is lacking, for example, due to iatrogenically compromised lens support during the time of surgery or as a late complication of a previous surgery. Whether there is capsular bag support or not, visualization of the device during implantation is important. In some implementations, the curved or biased fixation arms 2120 can allow for direct visualization of the device through the pupil such that the arms 2120 may be more readily grasped, which is particularly useful during externalization and fixation of the device within the eye. One or more of the fixation arms 2120 can be non-transparent so that they are more easily visualized through the pupil during implantation. In some implementations, only a portion of the fixation arm 2120 designed to project out from behind the iris so as to be visualized directly through the pupil is non-transparent.

The devices described herein can be viewed directly through the pupil even if there are no fixation arms 2120. In some implementations, the anterior geometry of the device 2100 is modified to improve anterior visualization through the pupil. For example, the anterior awnings 2126 can be sized and shaped to have at least a portion that projects inwardly or more centrally than an adjacent portion (e.g., towards a center axis extending through the central aperture 2115) such that the centrally-projecting portion of the awning 2126 is visible anteriorly through a dilated pupil without being substantially blocked by the iris. The awnings 2126 can be formed of a non-transparent material to improve this direct visualization. The geometry of the awnings 2126 can be visible relative to the IOL being implanted without impacting the optics of the IOL. This can increase the likelihood that the IOL will be properly secured within the recess 2104 of the device 2100. Post-operative lens dislocation can occur when the IOL haptic is left in a position that is anterior to the device 2100. Uncertainty of lens position can increase surgical time and the potential for tissue trauma as surgeons manipulate the device and/or tissue to confirm lens position relative to the device. Direct visualization of the device 2100 through the pupil lessens this uncertainty, particularly where intra-operative pupil diameter decreases mid-surgery.

FIG. 2A illustrates an example of the anterior awnings 2126 having a centrally-projecting visualization feature 2117 and two junction covers 2130. The visualization feature(s) 2117 can project centrally to allow for direct visualization of the device 2100 while avoiding substantially interfering with optics of the IOL after implantation by having a minimum inner diameter of about 4 mm. The junction covers 2130 provide coverage of the IOL haptic 114 where it forms a junction with the optic 112 of the IOL 110 to prevent this region of the IOL from contacting the iris 10. The visualization features 2117 can project sufficiently towards a central axis of the central aperture 2115, for example, at least about 2.5 mm to about 3 mm away from the central axis so that the features 2117 are visible through the pupil during an implantation procedure. The centrally-projecting visualization feature 2117 can narrow an inner dimension of the anterior opening 2127, for example, a distance $D_l$ of the anterior opening 2127 along the long axis of the device (see FIGS. 2B and 2C) while the overall dimensions of the anterior opening 2127 remain relatively large for accessing the internal recess 2104. The distance $D_l$ along the long axis of the device between the central-most edges of the anterior opening 2127 formed by the opposing awnings' visualization features 2117 can be at least about 7.0 mm down to about 5.0 mm, preferably about 6.0 mm. This distance $D_l$ is selected to be larger than the diameter $D_a$ of the central aperture 2115. For example, the diameter $D_a$ of the central aperture 2115 can be about 4.75 mm and the distance $D_l$ between the visualization features 2117 can be about 5.00 mm, about 5.25 mm, about 5.50 mm, about 5.75 mm, about 6.00 mm up to about 7.00 mm. Thus, even where the awnings 2126 incorporate the one or more visualization features 2117, the dimension of the anterior opening 2127 defined by the features 2117 can be larger than the diameter $D_a$ of the central aperture 2115.

The features 2117 shown in FIG. 2A projects centrally away from the leading fixation arm 2120*c* such that coverage provided by the awning 2126 near this arm is greater than coverage provided by the awning 2126 near the ends or corners of the device 2100 where the short sides 2107 meets the long sides 2108. The pair of features 2117 can therefore be positioned on the short sides 2107 of the device and project along the long axis. The visualization features 2117 can alternatively be positioned on the long sides 2108 of the device and project along the short axis (i.e., turned 90 degrees relative to what is shown in the figure). The visualization features 2117 can be located anywhere around the perimeter of the anterior region of the device so long as they extend sufficiently inward to be visible out from behind the iris fringe when the device is positioned in the eye. Discrete visualization features 2117 avoid narrowing the anterior opening 2127 around its full circumference providing anterior visualization without significantly impairing the user's ability to position the IOL through the anterior opening 2127 within the recess 2104 anterior to the platform 2105.

Figure 2E:
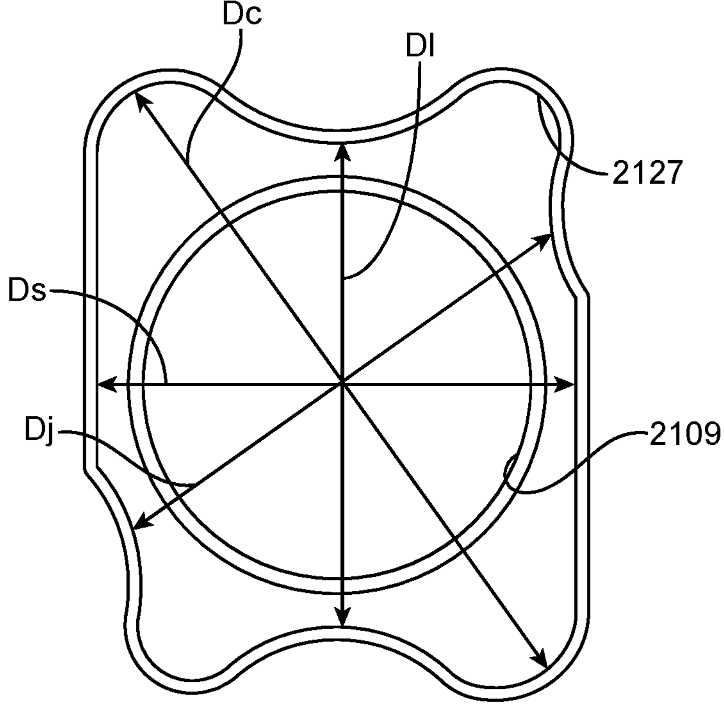
FIG. 2E shows a free-form shape of an anterior opening relative to a posterior opening of the device of FIG. 2A.
Figure 2F:
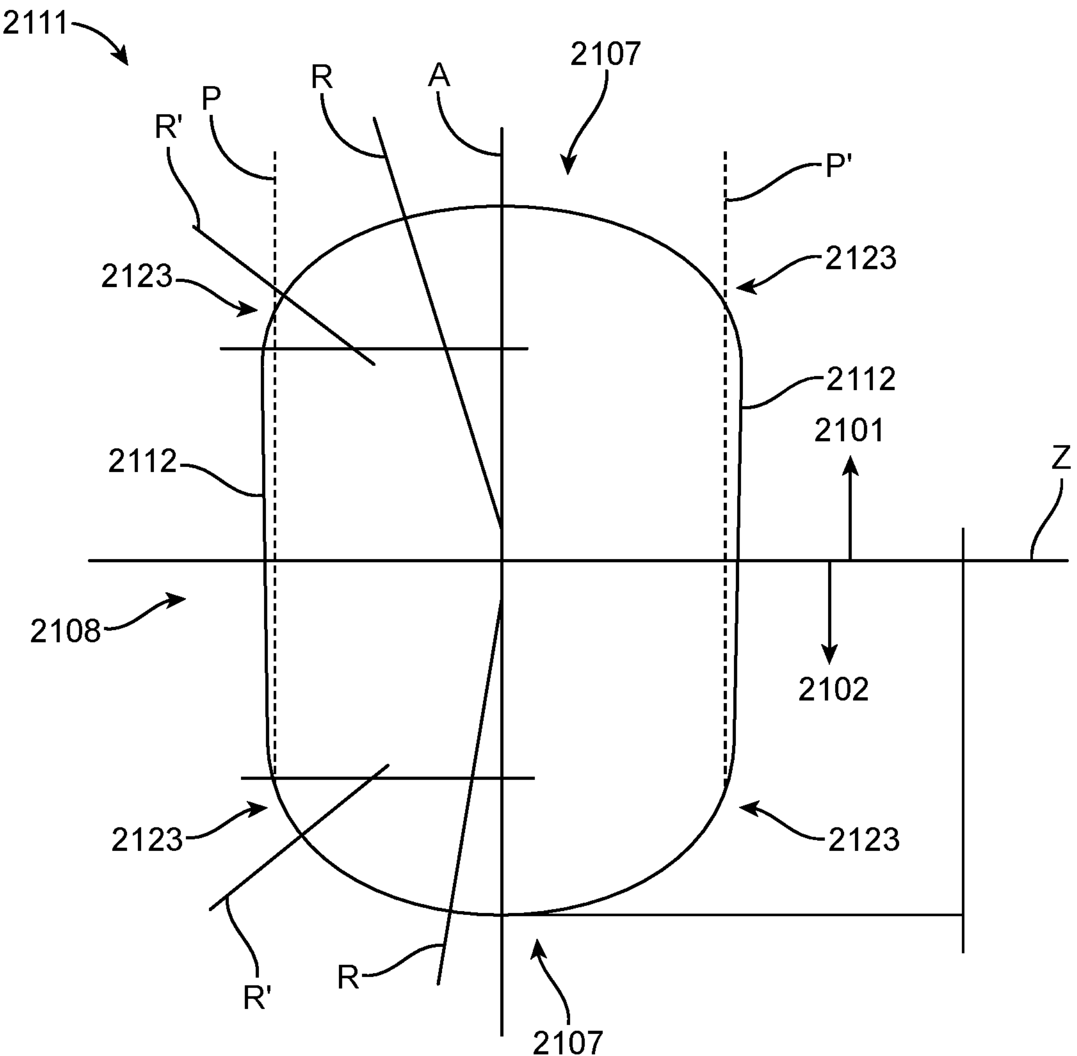
FIG. 2F shows an outer perimeter shape of a device having a major axis and a minor axis.

The discrete visualization features 2117 in combination with the one or more junction covers 2130 create a free-form shape to the anterior opening 2127. The undulating inner perimeter forming the free-form shape of the anterior opening 2127 can be relatively larger along at least one direction (e.g., between the long sides) and relatively smaller along another direction (e.g., between the short sides). The free-form shape also can create an even larger distance between edges of the perimeter in a particular orientation around the anterior opening 2127 that can be leveraged for insertion of the IOL into the recess. FIG. 2E illustrates the free-form shape of an anterior opening 2127 of the device of FIG. 2A relative to the circular shape of the inner perimeter 2109 defining the posterior opening 2115. As discussed above, the distance $D_l$ between the visualization features 2117 projecting inwardly from the short sides 2107 of the device can be less than, for example, a distance Ds between the long sides 2108 of the device. The distance $D_l$ between the visualization features 2117 as well as the distance Ds between the long sides 2108 of the device can be larger than the diameter $D_a$ of the central aperture 2115. For example, the undulating free-form shape of the anterior opening 2127 can also define a distance $D_c$ corner-to-corner across the center of the central aperture 2115 that is larger than the distance $D_l$ between the visualization features 2117, larger than the distance $D_j$ between the junction covers 2130, and also larger than the distance $D_s$ between the long sides 2108 of the device. The IOL can be inserted (or removed) through the anterior opening 2127 taking advantage of the asymmetrical free-form shape of the anterior opening 2127 by orienting the widest dimension of the IOL to slide between the widest part of the anterior opening 2127 (i.e., along line Dc). Once inserted through the anterior opening 2127, the IOL can be rotated or adjusted around the visual axis to orient the IOL within the recess.

As discussed in detail above, the fixation arms 2120 of the device are designed to be placed under tension to locate and stabilize the device within the eye. The geometry of the device can ensure that even when the arms are placed under tension, the device remains substantially within a single Z-plane and does not undergo distortion that causes lift of the awnings 2126 and/or visualization features 2117, particularly at the location of the leading fixation arm 2120*c* or any location of the device with narrowing radius under tension that are particularly prone to lifting of a visualization feature 2117. Each fixation arm 2120 can have a spring force that is a function of elongation of the material when under a load compared to, for example, an open loop haptic or coil spring may have a spring force provided due to bending of a material that has a substantially fixed length. The fixation arms 2120 once anchored in the eye can be under tensile stress and material elongation. For example, each fixation arm 2120 can provide for extension over a radius of between about 7.5 mm to 8.0 mm to accommodate diameters between about 15 mm to about 16 mm. The device has an operable range of tension for function. As an example, the device can be under a first amount of tension once implanted (X tension). The first amount of tension is the amount of tension in the minimum acceptable diameter. In other words, the device is under a minimum amount of tension in order to function, but is capable of being placed under greater tension to accommodate larger diameters. In the example of fixation arms 2120 capable of accommodating both 15 mm and 16 mm extension, each force transfer arm can operate while under the first tension X and while under at least a second tension. The second tension can be the sum of the first tension X plus a distance of tension (e.g., 0.5 mm of tension). The fixation arms can withstand the differential tension available in each extension ratio. To further illustrate the example, if each fixation arm 2120 in this implementation is about 4 mm long, then the second tension (X tension+0.5 mm of tension) can undergo a 12.5% increase in elongation to function at the 15 mm diameter and also function up to the 16 mm diameter. If the fixation arms 2120 in this example are 2 mm long, then the second tension (X tension+0.5 mm of tension) can undergo a 25% increase in elongation to function at the 15 mm diameter and also function up to the 16 mm diameter. If the fixation arms in this implementation that are about 6 mm long, then the second tension (X tension+0.5 mm of tension) can undergo a 6.25% increase in elongation to function at the 15 mm diameter and also function up to the 16 mm diameter. The decreased spring force of the fixation arms 2120 can enhance the safety and function of the device because the tension of the anchor on the ocular tissue is less dependent on variables that are difficult for the surgeon to assess—the eye's inherent dimensions and the specific location of the incisions. Additionally, the length of the fixation arm (e.g., between about 2 mm to 6 mm) as well as the inward curve (anteriorly or posteriorly) of at least one or more fixation arm 2120 improves access and visualization for the surgeon to find and fix the arm during the operation. The device can have a relaxed fixation diameter Dd that is between about 15 mm up to about 20 mm, preferably between about 16.50 mm up to about 18.00 mm, where the radius of the circle is measured from the center of the central aperture 2115 to an inner facing surface of the anchor 2125 of the straight fixation arm 2120 (see FIG. 2A).

The chassis of the device is designed to have minimal bulk allowing for the device to be inserted via small incisions while still providing enough space for the IOL to reside within it. The chassis geometry is also designed to minimally distort under varying loads. The chassis achieves these goals by having an asymmetric geometry (e.g., wider at the leading end 2101 than the trailing end 2106) and three-point fixation with the arms 2120. The leading fixation arm 2120*c* can extend at an angle from the midline of the device (i.e., the midline between the leading and trailing ends) that is about 90 degrees to be substantially perpendicular. The trailing fixation arms 2120*a*, 2120*b* can each extend at an angle from the midline of the device that is about 30 degrees. The leading and trailing fixation arms provide the three-point fixation. The leading fixation arm 2120*c* can pull along the long axis of the chassis (i.e., at about 90 degrees) while the trailing fixation arms 2120*a*, 2120*b* can pull at about 30 degrees from the short axis of the chassis. As discussed elsewhere herein, the leading fixation arm 2120*c* can be straight while the trailing fixation arms 2120*a*, 2120*b* can be biased inward. The fixation arms need not have uniform length due to the shape of the chassis (e.g., two elongate sides and two short sides) and the presence of three-point fixation. The fixation arms can have different lengths to distribute the stress on the arms in different ways around the device perimeter. For example, the straight leading fixation arm 2120*c* can be shorter than the inwardly-biased fixation arms 2120*a*, 2120*b*. This distributes the stress on the shorter leading arm 2120*c* at larger fixation diameters differently than the stress on the inwardly biased arms 2120*a*, 2120*b* at the larger fixation diameter. The tension applied to the chassis causes distortion in select areas around the perimeter resulting in a change in radius. The distortion causes some of those areas to undergo an increase in radius whereas other areas around the perimeter undergo a decrease in radius. The chassis side wall 2112 can be designed to encourage some areas to increase and others to decrease in radii upon the application of tension on the device due to the fixation arms. Areas of the side wall 2112 where tension causes radii to increase can be designed to be thinner whereas areas of the side wall 2112 where tension causes radii to decrease can be designed to be thicker. The wall thickness around the perimeter of the device varies thereby removing another point of symmetry, which will be described in more detail below regarding FIGS. 7A-7B.

Tension applied to the fixation arms 2120 can result in deformation of the chassis that depending on the design and geometry can cause lift of the visualization features 2117 that project centrally from the anterior awnings 2126. The tension can also lift junction covers 2130, but because their length is shorter compared to, for example, the inwardly-projecting length of the visualization feature 2117, the impact of lifting in the eye is less cause for concern. FIG. 4A is a side view and FIG. 4B is a top plan view of an implementation of a device 2100 having two visualization features 2117 and three fixation arms 2120. The fixation arms 2120 are shown placed under a minimal amount of tension sufficient to straighten the biased arms and generate a minimum amount of stretch to a first outer circumference. FIG. 4C is a side view and FIG. 4D is a top plan view of the device 2100 after the fixation arms 2120 are placed under a greater amount of tension resulting in the arms 2120 elongating to a larger outer circumference. FIG. 4D shows regions of the side wall 2112 along the elongate sides 2108 nearest the trailing end 2106 of the device that are stretched outward by the trailing fixation arms 2120*a*, 2120*b* so as to have a wider dimension across the trailing end 2106 of the device while the regions of the side wall 2112 along the elongate sides 2108 nearest the leading fixation arm 2120*c* are drawn inward so as to have a narrower dimension across the leading end 2101 of the device. The result of this distortion is that the visualization feature 2117 nearest the leading fixation arm 2120*c* deflects away from the plane it is intended to lie within (see FIG. 4C). A visualization feature 2117 that lifts upward away from this plane can be problematic if it contacts the iris overhead.

Figure 5A:
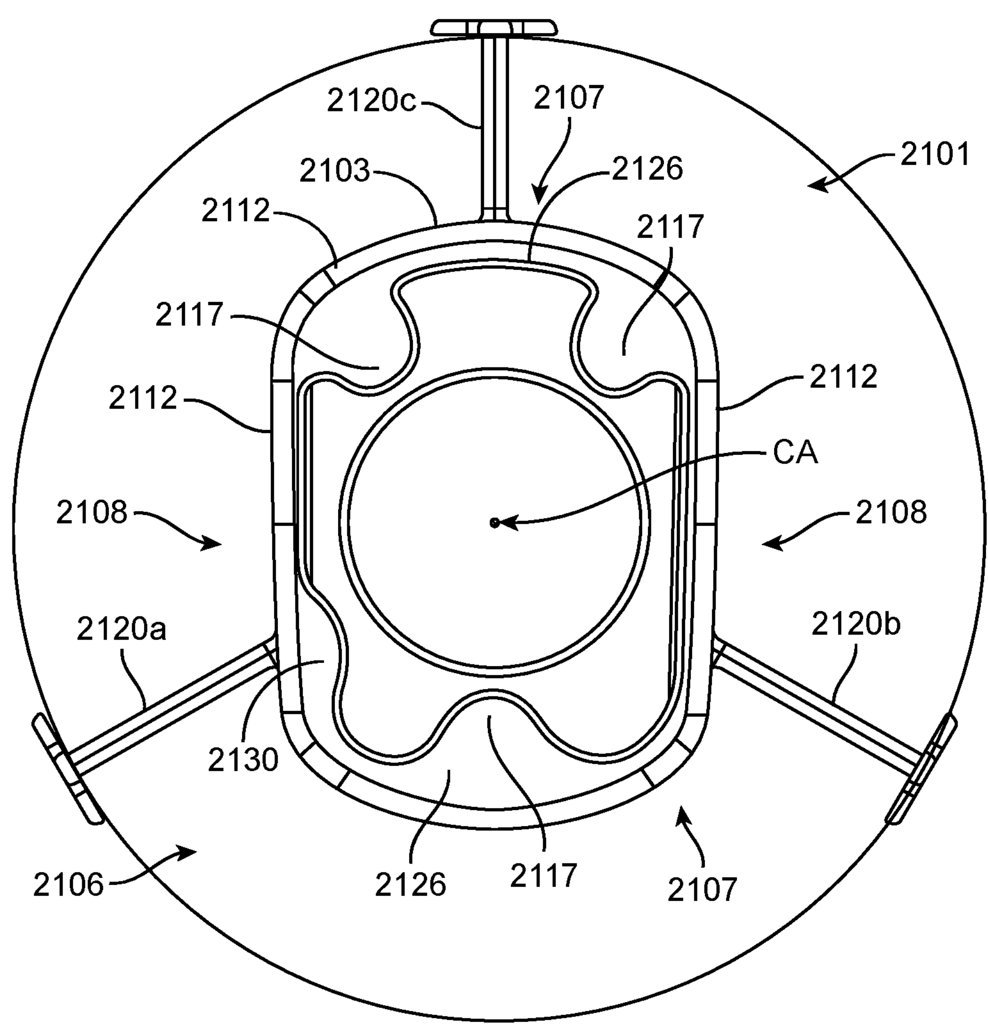
FIG. 5A is a top plan view of a device incorporating an implementation of visualization features.
Figure 5B:
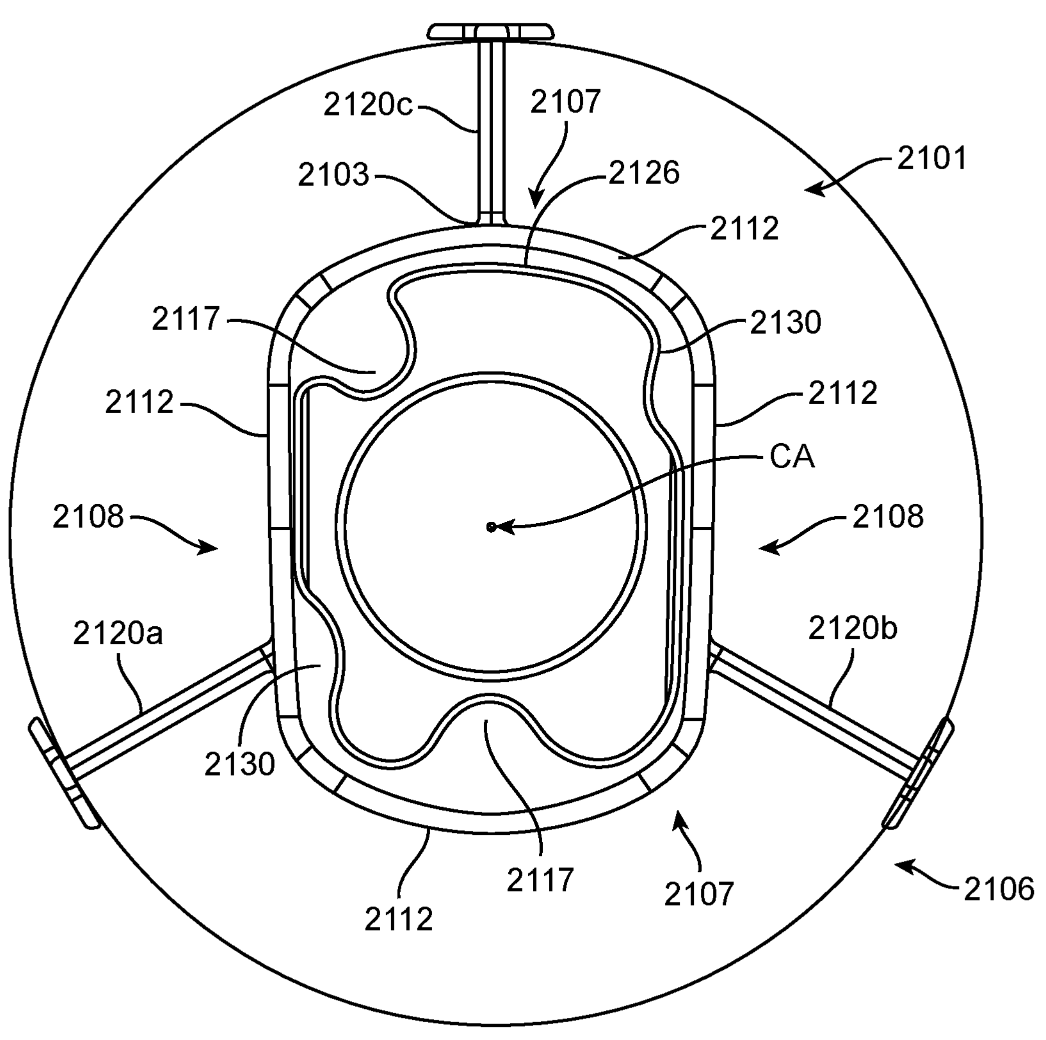
FIG. 5B is a top plan view of a device incorporating another implementation of visualization features.

To mitigate inadvertent distortion of the device such as awning lift, the geometry of the anterior region of the device can be designed to have awnings 2126 that extend minimally toward the central axis CA of the device (e.g., less than about 1 mm) or to have no awnings near the origin 2103 of the fixation arms 2120 or where there is a decrease in radii. The visualization feature(s) can extend radially inwardly from the outer perimeter wall at a location that increases in radius or at a location that does not change in radius when the plurality of fixation arms are placed under tension. FIG. 5A illustrates a device having a leading end 2101 with an awning 2126 located near the origin 2103 of the leading fixation arm 2120*c* that extends minimally inward toward the central axis CA. The awning 2126 is bordered on either side by two visualization features 2117. The trailing end 2106 of the device has an awning 2126 with a centralized visualization feature 2117 that projects toward the central axis CA and is located between the trailing fixation arms 2120*a*, 2120*b*. FIG. 5B illustrates another implementation of a device having a leading end 2101 with an awning 2126 that only minimally projects toward the central axis CA near the origin 2103 of the leading fixation arm 2120*c* and a single visualization feature 2117 located away from the origin 2104 such as on one side of the awning 2126. The visualization feature 2117 of the awning 2126 is located to a side of the origin 2103 of the fixation arm 2120*c* so that it is projecting from a location near the outer perimeter wall having a radius that increases in radius or that does not change in radius upon placing the fixation arm under tension.

Figures 6A, 6B, 6C, 6D:
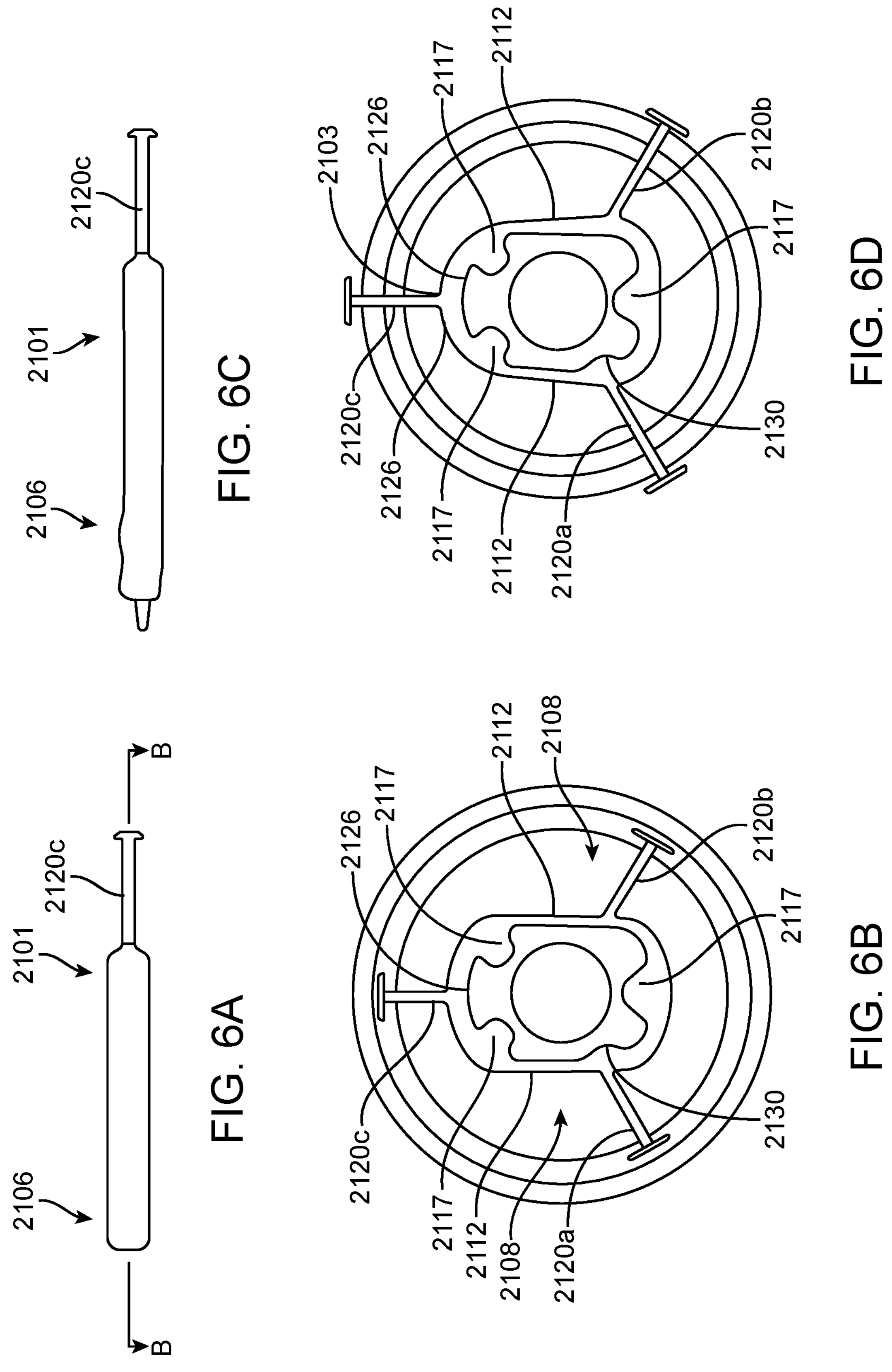
FIG. 6A is a side view of a device placed under a minimum amount of tension.
FIG. 6B is a top plan view of the device of FIG. 6A.
FIG. 6C is a side view of the device of FIG. 6A placed under a maximum amount of tension illustrating distortion, but no lift of the visualization feature.
FIG. 6D is a top plan view of the device of FIG. 6C.

FIG. 6A is a side view and FIG. 6B is a top plan view of the device 2100 having two visualization features 2117 positioned on either side of the origin 2103 of the leading fixation arm 2120*c* and a minimally-projecting awning 2126 centrally between them at the location of the origin 2103. The fixation arms 2120 are placed under a minimal amount of tension sufficient to straighten the biased arms and generate a minimum amount of stretch to a first outer circumference. FIG. 6C is a side view and FIG. 6D is a top plan view of the device 2100 after the fixation arms 2120 are placed under a greater amount of tension resulting in the arms 2120 elongating to a larger outer circumference. FIG. 6D shows regions of the side wall 2112 along the elongate sides 2108 nearest the trailing end 2106 of the device are stretched outward by the trailing fixation arms 2120*a*, 2120*b* to have a wider dimension across the trailing end 2106 of the device. The regions of the side wall 2112 along the elongate sides 2108 nearest the leading fixation arm 2120*c* are drawn inward to have a narrower dimension across the leading end 2101 of the device. Despite this distortion, the visualization features 2117 on either side of the leading fixation arm 2120*c* remain substantially within the same plane as in FIG. 6A and do not deflect or lift (see FIG. 6C). The origin 2103 is drawn outward by the leading fixation arm 2120*c* causing the leading end 2101 of the device to take on a smaller radius and the two visualization features 2117 angle toward one another to accommodate the side wall narrowing. Placing the one or more visualization features 2117 along the elongate sides 2108 away from the location of the fixation arms and/or near the corners where the radius increases while the device is under tension mitigates deflection of the visualization features 2117 away from their plane. The location of the visualization features 2117 off-set from or to the side of the origin of the fixation arms ensures the visualization features 2117 extend substantially within the horizontal plane prior to and after placing the fixation arms under tension.

In some implementations, the visualization features 2117 are designed to deflect upon the application of tension, but they are designed to deflect away from the iris. For example, the geometry of the anterior region of the device can be designed to encourage the visualization features 2117 to deflect towards the IOL within the recess 2104 when the arms 2120 are placed under tension.

Figures 7A, 7B:
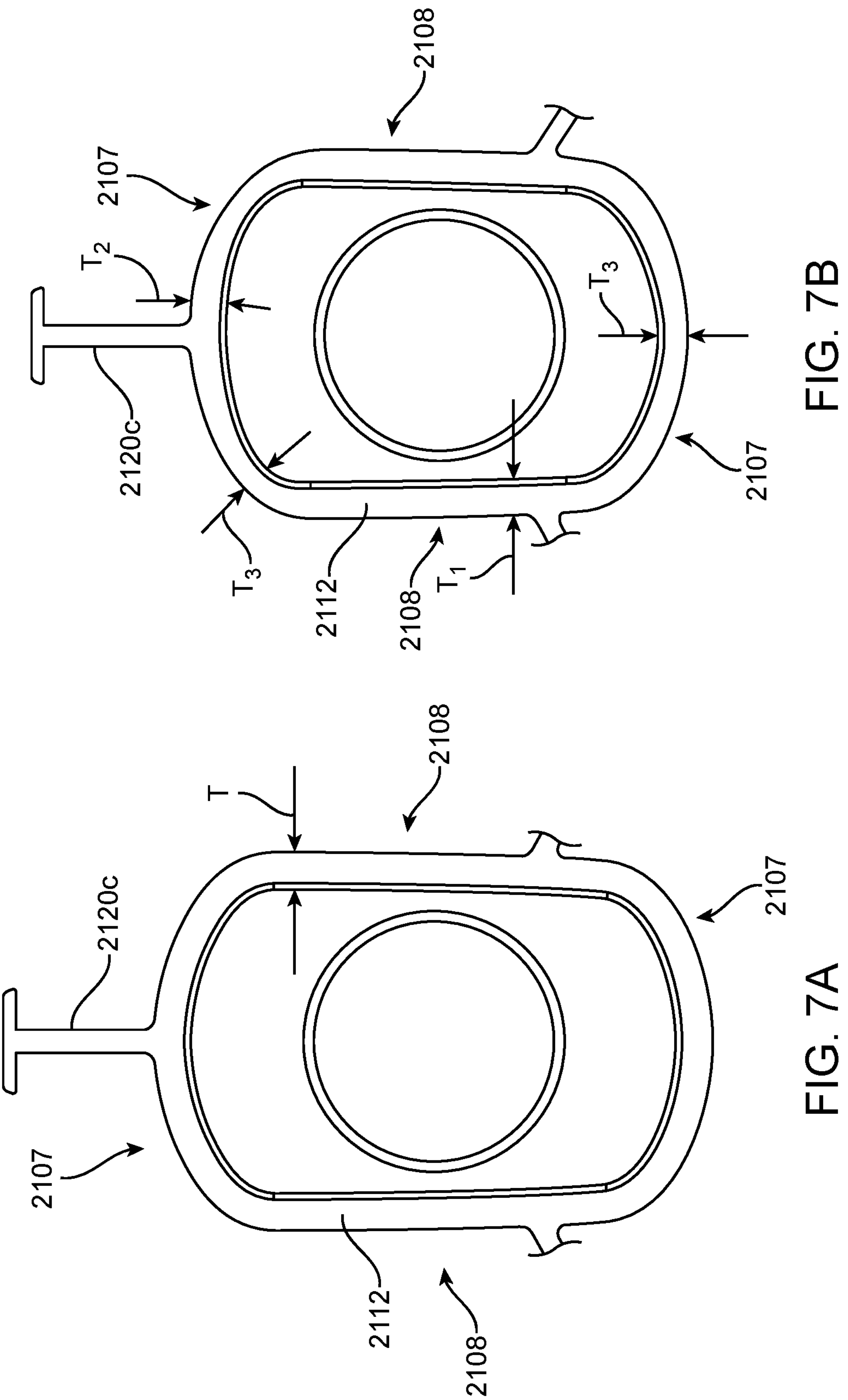
FIG. 7A is a cross-sectional, partial view of the device of FIG. 4A taken along line A-A.
FIG. 7B is a cross-sectional view of the device of FIG. 6A taken along line B-B.

As mentioned above, areas where tension causes side wall 2112 radii to increase can be designed to be thinner whereas areas where tension causes side wall 2112 radii to decrease can be designed to be thicker. FIG. 7A is a cross-sectional view of the device shown in FIG. 4A taken along line A-A. FIG. 7B is a cross-sectional view of another the device shown in FIG. 6A taken along line B-B. The leading fixation arm 2120*c* is shown in each of FIGS. 7A-7B for orientation whereas the other fixation arms are shown only partially. The side wall 2112 of the chassis in FIG. 7A (including along the elongate sides 2108 and along the shorter sides 2107) has a thickness T that is relatively uniform around the perimeter of the device including in the corners and in the location of each fixation arm 2120. In contrast, the side wall 2112 of the chassis shown in FIG. 7B has a thickness T that changes around the perimeter of the device. The greatest thickness T1 of the side walls 2112 is at the location of the two trailing fixation arms 2120*a*. 2120*b* along the elongate sides 2108. The thickness T2 of the side wall 2112 at the location of the leading fixation arm 2120*c* (i.e., along the short side 2107) is less than the thickness T1 of the side wall 2112 at the location of the trailing fixation arms 2120*a*, 2120*b* (i.e., along the elongate sides 2108). The thickness T3 of the side wall 2112 at the location of the visualization feature(s) 2117 is less than the thickness T1 of the side wall 2112 along the elongate sides 2108 and the thickness T2 of the side wall 2112 at the location of the leading fixation arm 2120*c*. The wall thickness around the perimeter of the device varies thereby removing another point of symmetry.

The optical element can be inserted within the device in a variety of ways. The optical element can be injected from an injector that is located anterior to the device so that release of the optical element from the injector positions the optical element on top of the device prior to a user manipulating the device to insert it through the anterior opening 2127. The optical element can be allowed to unfurl prior to inserting the optical element through the anterior opening 2127 of the device. In other methods, the optical element can be manipulated into the device while it is at least partially folded. The optical element can also be injected by the injector through the anterior opening 2127 so that, the case of an IOL, at least one haptic of the IOL is injected directly into the chassis of the device. The optical element can be allowed to unfold while at least partially implanted within the device and then the remainder of the lens manipulated into position within the device. The optical element can be manipulated by a user through one or more trocar cannulae.

Implementations of the support structure may have an outer perimeter wall of various geometrical shapes, axes and symmetries or non-symmetries. For example, the device may have a long axis and a short axis, two shorter sides and two longer sides. FIG. 2F illustrates an outer perimeter wall 2111 having a long axis A and a short axis Z with two longer sides 2108 and two shorter sides 2107. The shorter sides may be straight and parallel to one another, straight and slightly angled with respect to one another, or at least partially or entirely curved outwardly away from the central axis of the device that passes through the aperture. The longer sides may also include both a straight portion and a portion curved outwardly away from the device's central axis. If a longer side includes both a straight portion and a slightly curved portion, then the slightly curved portion may be adjacent the junction between the outer perimeter and the fixation arm associated with the longer side. FIG. 2F shows a region of the elongate sides 2108 on the trailing end 2106 of the device is curved and does not lie parallel to straight lines P, P'. A region of the elongate sides 2108 on the leading end 2101 of the device straightens out so that this segment does lie substantially parallel to straight lines P, P'. Thus, each elongate side 2108 can have both straight and curved portions or can be completely straight or can be completely curved. The trailing end 2106 of the device shown in FIG. 2F is also narrower than the leading end 2101 due to the elongate sides 2108 not being perfectly parallel along their length.

The longer sides may be parallel or nominally parallel (in the case of slight curvature of at least a portion of the longer sides), to produce an outer perimeter akin to a rectangle, with shorter, straight, or rounded sides joined to the longer sides at rounded corners. Or the longer sides may be partially or entirely slightly angled or nominally angled with respect to one another (in the case of slight curvature of at least a portion of the longer sides), to produce an outer perimeter akin to a slightly tapered trapezoid, with shorter straight or rounded sides joined to the longer sides at rounded corners.

As used herein, the term "about" or "nominally" means a range of values including the specified value, which a person of ordinary skill in the art would consider reasonably similar to the specified value. In aspects, about or nominally means within a standard deviation using measurements generally acceptable in the art. In aspects, about or nominally means a range extending to +/−10% of the specified value. In aspects, about or nominally includes the specified value.

A radius of curvature of at least a portion of each longer side may be much larger than a radius of curvature of a shorter side, thereby producing a much more gradual or subtle bowing of the longer side compared to the degree of curvature of the shorter side. The corners may have a radius of curvature smaller or much smaller than a radius of curvature of either the longer sides or shorter sides, thereby providing a support structure with an outer perimeter having at least two or three or more different radii of curvature to produce the desired outer perimetrical shape. In a preferred embodiment, a support structure has longer sides with a large radius of curvature to produce very slight outward bowing (e.g., about 35 mm up to a flat line), shorter sides with a smaller radius of curvature by at least one order of magnitude compared to the radius of curvature of the longer sides, to produce more exaggerated bowing for the shorter sides, and rounder corners having a much smaller radius of curvature (e.g., no radius up to about 3.5 mm or about 5.0 mm).

The support structure may have an outer perimeter that is symmetrical with respect to the long axis of the device such that each side of the outer perimeter is a mirror-image of the other about the long axis and is also symmetrical with respect to the short axis of the device, or may have an outer perimeter that is symmetrical with respect to the long axis of the device, but which is non-symmetrical with respect to the short axis of the device.

A support structure may have opposed awnings on opposite sides of the central axis of the device that passes through the central aperture. Each of these awnings forms a recess underneath the awning for securing one of an IOL's haptics when an IOL engages the support structure. As disclosed herein, each such awning may have a contour formed of various inwardly projecting portions, including, for example, a centrally-projecting visualization feature that extends sufficiently inwardly towards the central axis so as to be visible behind an iris during implantation of the device in the patient's eye, and/or one or more additional projections extending inwardly so as to at least partially cover a portion of an IOL haptic when the haptic is placed underneath the awning. In some embodiments, the awnings are arranged such that each awning is a mirror-image of the other around the device's short axis and symmetrical with respect to the short axis. In these cases, the entire lens support device may be symmetrical with respect to either or both of the device's long axis and short axis. Alternatively, the awnings may be arranged such that they are non-symmetrical with respect to either or both of the device's long axis and short axis, and may be of such configuration that no axis of symmetry exists within the device for the awnings. In addition, when such awnings are coupled with the various outer perimetrical shapes available for the device, a lens support device may have outer perimetrical symmetry about one or both of the device's long axis and short axis, and also have two awnings that are either symmetrical about one or both of the device's long axis and short axis, or which are non-symmetrical with respect to both long and short axes.

The support structure may have an outer perimeter shape that has one configuration with the device at rest before implantation, and a second, different geometrical configuration when the structure is implanted and under tension. For example, with the device at rest, in a device having two shorter sides and two longer sides, the entire length of, or a portion of, each of the longer sides may be slightly angled towards one another so that the lens support body is slightly tapered. When such a slightly tapered device is made of suitable dimensions and suitably flexible materials, the device, when placed under tension through implantation of the fixation arms into contact with the sclera of the eye, the outer perimeter geometrical shape may change from a slightly tapered configuration to a less slightly tapered configuration or a configuration more closely akin to a rectangle, with longer sides that are closer to being, or are actually or nominally, parallel. This modification of outer perimetrical shape may be helpful to create the desired shape of the support structure when implanted, when the device is such that tensioning tends to distort the original at-rest shape of the device.

The devices described herein can serve to support implantable intraocular devices including devices having optical elements, such as intraocular lenses (IOLs) as described above even where there is insufficient or absent capsular support. The devices described herein can support other types of implantable ophthalmic devices that are configured to be implanted long-term within the eye, devices with optical elements including implantable miniature telescope (IMT), magnifiers, cameras, and the like, as well as devices without optical elements such as an artificial iris, drug eluting ring implants for posterior segment drug delivery, biosensors for continuous monitoring of an intraocular characteristic (e.g., pressure, glucose, inflammation), and others. The devices provides this support with minimal-to-no suturing. The devices are particularly useful for supporting heavier implants such as IMTs, which can be difficult to support particularly where capsular bag integrity is compromised, preventing inadvertent tilt and dislocation of the implant relative to the eye anatomy.

Congenital or acquired aniridia leads to visual symptoms and ocular problems such as reduced visual acuity, increased light sensitivity, and glaucoma. Iris prosthetics (CUSTOMFLEX, HumanOptics) are designed to mimic the original appearance of a patient's iris. The artificial iris controls light entry of a fixed pupil aperture to improve vision and reduce light sensitivity as well as provide cosmetic improvements. The prosthetic can be injected into the posterior chamber of the eye after removal of a natural lens and IOL implantation into the capsular bag. However, in the case of absent or insufficient capsular support many artificial iris prosthetics are unable to be implanted or are implanted using suturing techniques that are technically difficult and can lead to pain and other side effects for the patient.

Figure 8A:
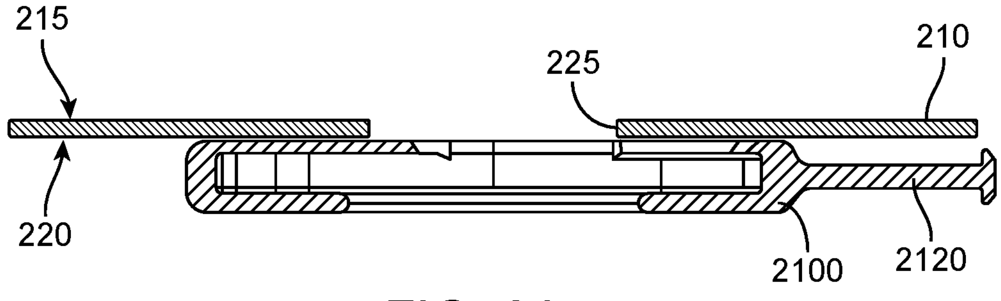
FIG. 8A is a cross-sectional schematic view of a scleral suspension device having an artificial iris attached.
Figure 8B:
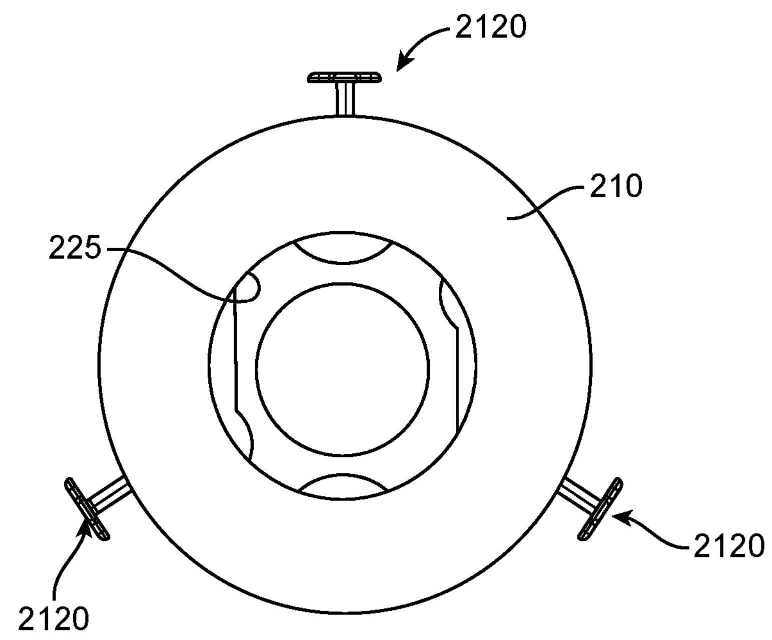
FIG. 8B is a top plan view of the device of FIG. 8A.

FIGS. 8A-8B illustrate an implantable scleral suspension device 2100 supporting an artificial iris prosthetic 210 that is sized and shaped to fill the space of an absent iris. The artificial iris prosthetic 210 can have an anterior side 215 and a posterior side 220 that are each substantially smooth and planar. The anterior and posterior sides 215, 220 need not be planar can also be slightly convex. The anterior side 215 of the artificial iris prosthetic 210 has a pattern of color applied to it such as by painting, coating, printing, or otherwise that is designed to cosmetically match the fellow eye. The artificial iris prosthetic 210 can have an aperture 225 having a diameter sized to a desired fixed aperture to resemble a pupil. The diameter of the aperture 225 can be in a range of about 1 mm to about 8 mm, preferably about 3 mm to 5 mm. The edge design of the aperture 225 can be rough or have notched geometry to resemble a natural pupil.

The artificial iris prosthetic 210 can have an oversized outer diameter (e.g., about 16 mm) that is trephined to size at the time of implantation to a smaller diameter (e.g., 9.0-12.5 mm). The punch can have an internal diameter that corresponds to the desired external diameter of the artificial iris prosthetic 210. The artificial iris prosthetic 210 can be a membrane of silicone elastomer that has a thickness that is between about 100 microns to about 400 microns, preferably about 200 microns.

In some implementations, the artificial iris prosthetic 210 can be a separate component configured to be attached to the device 2100 after being customized for size. If attached as a separate piece, the artificial iris prosthetic 210 can be affixed into place with one or more coupling features 230 on a posterior surface 220 of the artificial iris prosthetic 210 that are configured to engage one or more regions of the device 2100 including a perimeter of the device such as the elongate sides 2108 and/or the short sides 2107, the anterior-facing surfaces of the device such as one or more of the awnings 2126, and/or one or more fixation arms 2120 of the device 2100.

Figure 9:
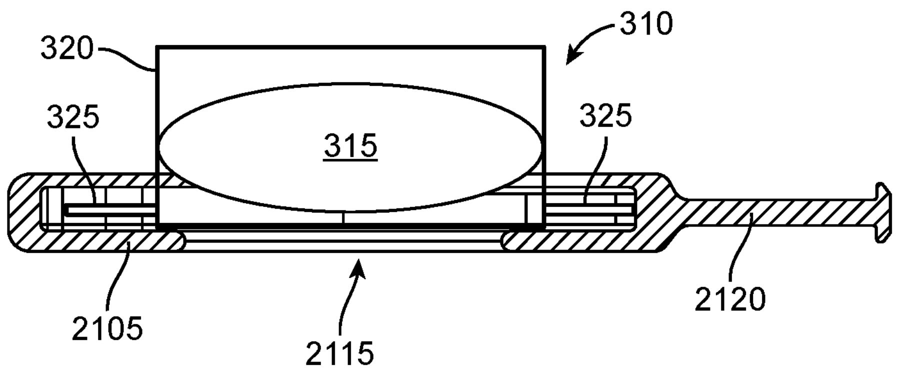
FIG. 9 is a cross-sectional schematic view of a scleral suspension device having an implantable miniature telescope (IMT) positioned within the recess.
Figure 11A:
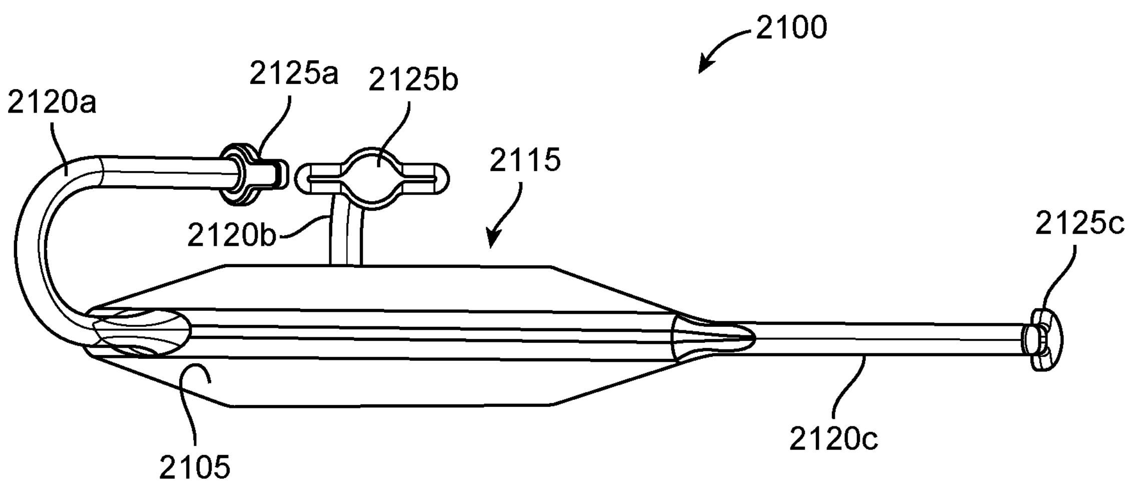
FIG. 11A is a side view of the scleral suspension device of FIG. 10B.
Figure 11B:
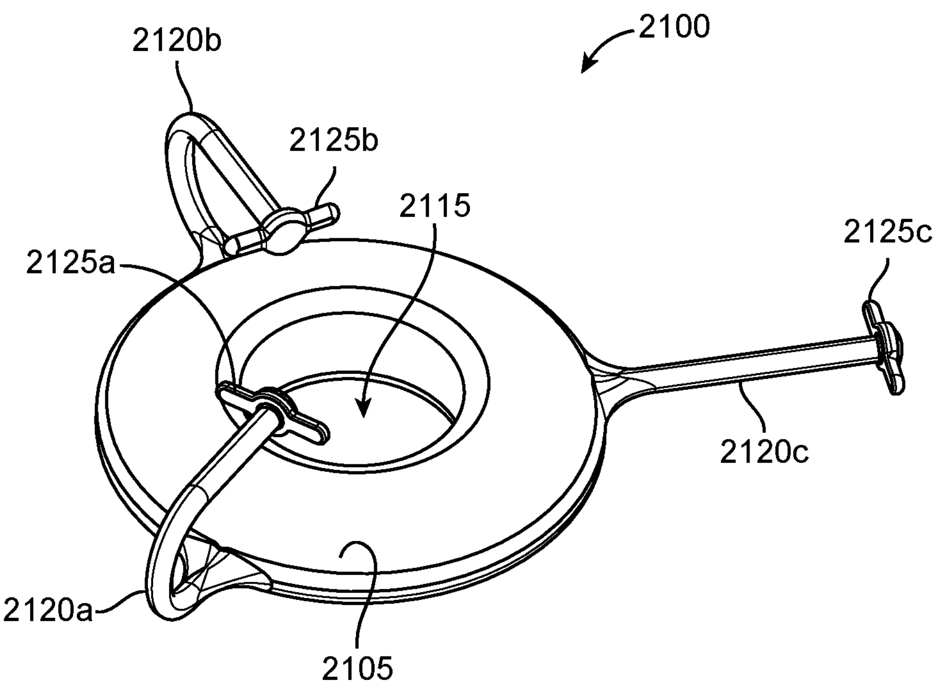
FIG. 11B is a perspective anterior end view of the scleral suspension device of FIG. 11A.

The scleral suspension devices described herein allow for implantation of devices such as implantable miniature telescopes (IMT) in pseudophakic patients in a scleral fixated manner. FIG. 9 shows an IMT 310 in schematic including an optical element 315 such as a glass capsule containing a wide-angle micro-optical element and an outer carrier 320. The outer carrier 320 can be optically clear and have the optical element 315 located within it. The optical element 315 can include at least one lens configured to magnify an image on the retina of the eye. After removal of the eye's natural lens, IMTs are conventionally implanted fully within the capsular bag. The IMTs can incorporate haptics that are designed specifically to engage the capsular bag. The haptics are configured to engage against the inside surface of the capsular bag and in some varieties provide a spring tension in an outward direction or are fully enclosed by the lens capsule. Instead, the devices described herein can provide a platform or scleral suspension system for stabilizing and supporting the IMT 310 within the eye even where the natural lens capsule is completely absent. In some implementations, the IMT 310 received within the devices described herein can be a stand-alone device designed to be implanted in an eye, but instead is implanted within the device 2100. The scleral suspension devices described herein can support a fully implantable IMT system such that the haptic system of the IMT is contained within and mates with at least a region of the device. For example, FIG. 9 shows the IMT can have a haptic 325 such as open loop haptics, fixating the IMT 310 within the scleral suspension device 2100 via the outward spring force of the open loop haptics against an internal surface of the device 2100. The IMT haptics are used to affix the IMT within the device 2100 and the fixation arms 2120 of the scleral suspension device 2100, in turn, affix the entire assembly within the eye without any need for a capsular bag. The haptics 325 of the IMT 310 can engage the device 2100 similarly to how haptics 114 of a standard IOL 110 engages the device as described elsewhere herein such as with regard to FIG. 1C. The planar posterior platform 2105 can act as a support against which a posterior surface of the IMT 310 can be positioned. The IMT 310 can sit against the anterior-facing surface of the posterior platform 2105 so that the optical element 315 of the IMT 310 is aligned with the central aperture 2115 of the device. The aperture 2115 of the device 2100 can be sized to fit most IMT devices or between about 3.5-4.0 mm. The optical element 315 of the IMT may have a diameter and a length that protrudes in one or both anterior and posterior directions relative to the device 2100. The IMT 310 of FIG. 9 is shown with the carrier 320 projecting anteriorly relative to the awning of the device and the posterior end of the carrier 320 remaining within the interior of the device 2100. The IMT 310 may also project posteriorly through the aperture 2115 of the device 2100 so that the posterior end of the carrier 320 is positioned posteriorly relative to the platform 2105, such as shown in FIG. 11E. Still further, FIGS. 11G-11H illustrate an IMT that protrudes from both the anterior and posterior ends of the device 2100.

The IMT 310 can have any of a variety of haptic configurations that can be configured to engage one or more regions of the device 2100. The haptic of the IMT 310 can be an open loop haptic as described above or another form of haptic including traditional compression-based haptic designs like J-Loop, C-Loop, Closed Loop, Kellman Haptics, plate haptics, or other haptic designs. In some implementations, the haptic 325 of the IMT 310 can be a rigid flange that engages a region of the posterior platform 2105 of the device 2100 to stabilize the IMT 310 in all directions. In still other implementations, the IMT may be designed to mate specifically with the scleral suspension device 2100, for example with one or more fixation elements such that the IMT itself need not incorporate any traditional haptic configured to engage with eye tissue, such as the lens capsule. When mated with the scleral suspension device 2100, a posterior surface of the outer carrier of the IMT 310 can engage the anterior surface of the support structure of the scleral suspension device 2100 and the optical element of the IMT 310 is optically aligned with the central aperture of the scleral suspension device 2100. The optical element of the IMT 310 can have a length sized to protrude in one or both anterior and posterior directions relative to the scleral suspension device 2100.

Figure 10A:
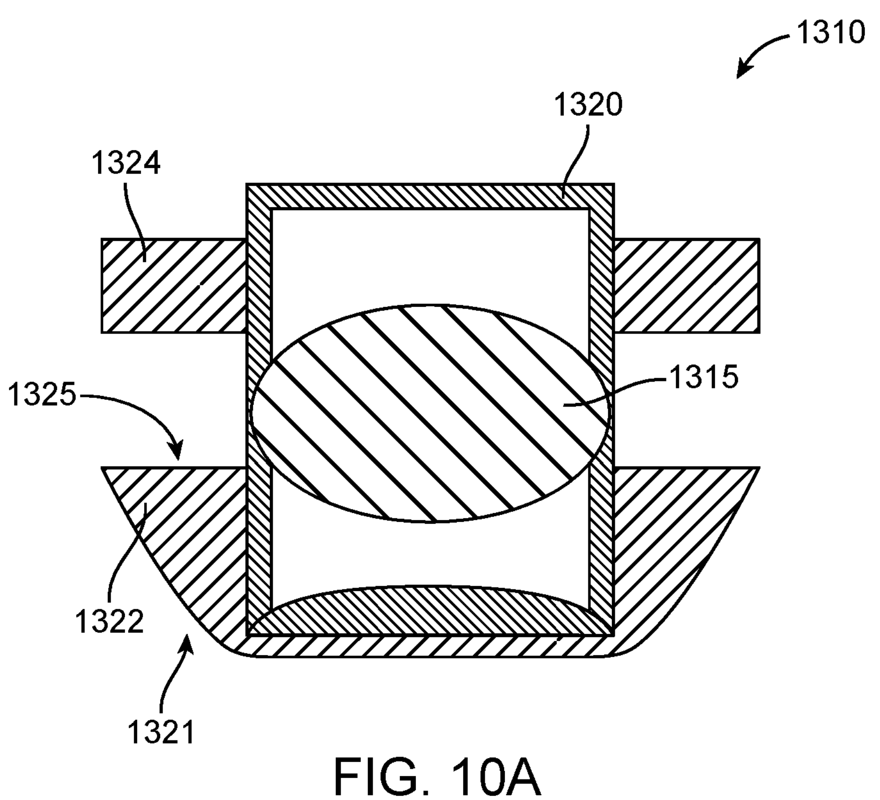
FIG. 10A is a cross-sectional schematic view of an implantable miniature telescope (IMT) having fixation elements for mating with a scleral suspension device.

FIG. 10A is a cross-sectional schematic of an IMT 1310 having an outer carrier 1320 containing an optical element 1315. The outer carrier 1320 can be an optically clear PMMA material. The carrier can be cylindrical having a circular cross-sectional shape or can have another geometric cross-sectional shape. The IMT 1310 is designed specifically to mate, such as by a snap-fit, with a central aperture 2115 of a scleral suspension device 2100, such as the one shown in FIG. 10B and also FIGS. 11A-11K. The outer carrier 1320 of the IMT can be cylindrical and have a circular cross-sectional shape. The outer diameter of the outer carrier 1320 can be sized to extend through the central aperture 2115 of the scleral suspension device 2100. The external surfaces of IMT 1310 can be designed with one or more features, such as a snap-fit feature, designed to allow for easy implantation and secure fixation with the central aperture 2115 of the device 2100. In an implementation, the outer carrier 1320 of the IMT 1310 can incorporate a posterior mating feature 1322 and an anterior stop 1324. The posterior mating feature 1322 is designed to be easily inserted through the central aperture 2115 of the device 2100 in an anterior-to-posterior direction and provide significant resistance from being withdrawn through the central aperture 2115 from a posterior-to-anterior direction.

Any of a variety shapes of the posterior mating feature 1322 is considered herein including a flange having a barbed shape, such as the structure of an arrow or other barbed feature or a ramped shape, such that the device preferentially slides through the central aperture in an anterior-to-posterior direction compared to the posterior-to-anterior direction. The shape of the posterior mating feature(s) 1322 is designed to provide a one-way insertion of the IMT 1310 through the central aperture 2115 of the device due to a ramped posterior-facing surface 1321. The outer diameter at a posterior-most end of the posterior mating feature 1322 can approach the outer diameter of the outer carrier 1320 and gradually increase moving anteriorly. The outer diameter at an anterior-most end of the posterior mating feature 1322 can be sized to approximate the inner diameter of the central aperture 2115 and in some implementations slightly larger than the inner diameter of the central aperture 2115. The material of scleral suspension device 2100 and/or the mating feature 1322 can be flexible and configured to deform upon application of a force against a posterior region of the posterior mating feature 1322 and resist deformation upon application of a force against an anterior region of the posterior mating feature. This allows for the larger outer diameter of the anterior-most end of the mating feature 1322 to be urged through the aperture 2115 while still providing sufficient stiffness that prevents the mating feature 1322 from being withdrawn back through the aperture 2115. Additionally, the anterior-facing surface 1325 of the posterior mating feature 1322 can be at an angle relative to an outer surface of the carrier 1320 and the plane of the aperture 2115 that withdrawing it back through the aperture 2115 is substantially prevented. The angle between the anterior-facing surface 1325 of the posterior mating feature 1322 can be approximately 90 degrees as shown in FIG. 10A or another angle that resists sliding of the posterior mating feature 1322 back through the aperture 2115 in a posterior-to-anterior direction.

The posterior mating feature(s) 1322 can be continuous around the surface of the IMT 1310 at a given plane to be fully annular and surround a full circumference of a posterior end region of the outer carrier 1320. The posterior mating feature 1322 need not be fully annular, however, and instead can be formed by at least two or more distinct mating features 1322 located at multiple points around a circumference of the posterior end region of the outer carrier 1320 (sec, e.g., FIGS. 11I-11K). The anterior stop 1324 is preferentially designed to prevent the IMT 1310 from passing through the central aperture 2115 regardless the direction of motion of the device. The anterior stop 1324 can have a continuous or discontinuous engaging surface. The anterior stop 1324 can be fully annular and surround a full circumference of an anterior end region of the outer carrier or the anterior stop can be formed by at least two or more distinct mating features located at multiple points around a circumference of the anterior end region of the outer carrier 1320. The anterior stop and the posterior mating feature(s) can be integral with the carrier of the IMT or can be assembled with the carrier of the IMT at a time of use. A position of the anterior stop and/or the posterior mating feature(s) relative to the carrier can be adjustable. The anterior stops 1324 can be positioned so that they are aligned directly in an anterior-to-posterior direction with the posterior mating feature 1322. Alternatively, the anterior stops 1324 can be offset from the posterior mating feature 1322. FIGS. 11J-11K illustrate anterior stops 1324 that are off-set around a circumference of the device from the posterior mating features 1322. The anterior end view of the system shown in FIG. 11K illustrates the spacing between the anterior stops 1324 and the posterior mating features 1322 and also the fixation arms 2120. There are three stops 1324 arranged at about 120 degrees around the circumference and three mating features 1322 also arranged at about 120 degrees around the circumference of the IMT 1310 in between the locations of the stops 1324. Notably, the locations of the anterior stops 1324, the posterior mating features 1322, and the fixation arms 2120 are all off-set from one another around the circumference of the device.

The stop/mating features and haptics described herein can be integrated into the carrier 1320 of the IMT 1310 or components that are added at the manufacturing stage. Alternatively, the stop/mating features and haptics can be assembled onto the IMT or otherwise modified in the operating room prior to implantation. The mechanical interaction of device and the device engaging features are such that their relative positions can be adjusted in a surgical setting, but are intended to provide stable fixation of the IMT 1310 in the device 2100 in normal post-operative conditions. In some embodiments, the anterior stop 1324 and posterior mating feature 1322 are specifically designed to be pushed through the central aperture 2115. An instrument can additionally or alternatively be used to manipulate the central aperture 2115 of the device 2100 in a way (e.g. "tire iron") to ease the IMT 1310 through the aperture 2115 in a controlled manner. In implementations, where the IMT 1310 incorporates haptics, the position of the haptics can be tailored based on the desired axial position IMT 1310 and the predicted axial position of the IMT engaging features of the device 2100.

To optimize visual function, the IMT 1310 should engage the device 2100 in a way that prevents or minimizes decentration and tilt. Aligning the external surface of IMT 1310 with the internal surface of the central aperture 2115 across an appreciable thickness aids in preventing or minimizing decentration and tilt. A thicker posterior platform 2105 can form a longer internal surface of the central aperture 2115 that extends along a larger circumferential band of the carrier 1320 of the IMT 1310 to align the IMT 1310 with the optical axis more reliably. At least a central region of the posterior platform 2105 defining the central aperture 2115 can be about 200-2000 microns thick, or about 200-1000 thick, or about 200-500 microns thick. In some implementations, a central region of the posterior platform 2105 defining the central aperture 2115 can be about 1000-1500 microns thick and anywhere in between.

Figures 11C, 11D:
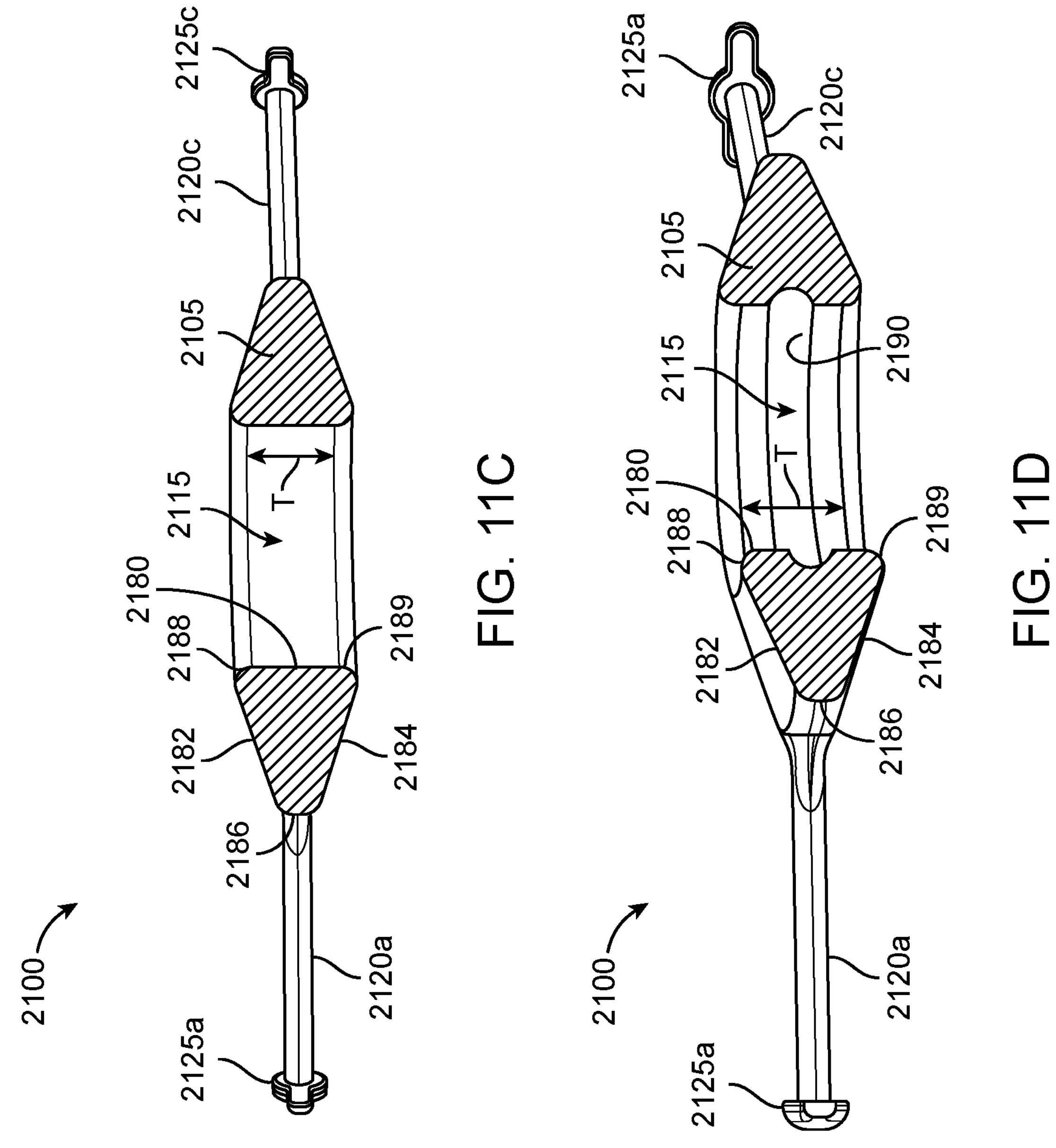
FIG. 11C is a cross-sectional view of the scleral suspension device of FIG. 11A after tensioning of the biased arms.
FIG. 11D is a cross-sectional view of another implementation of a scleral suspension device.
Figure 11E:
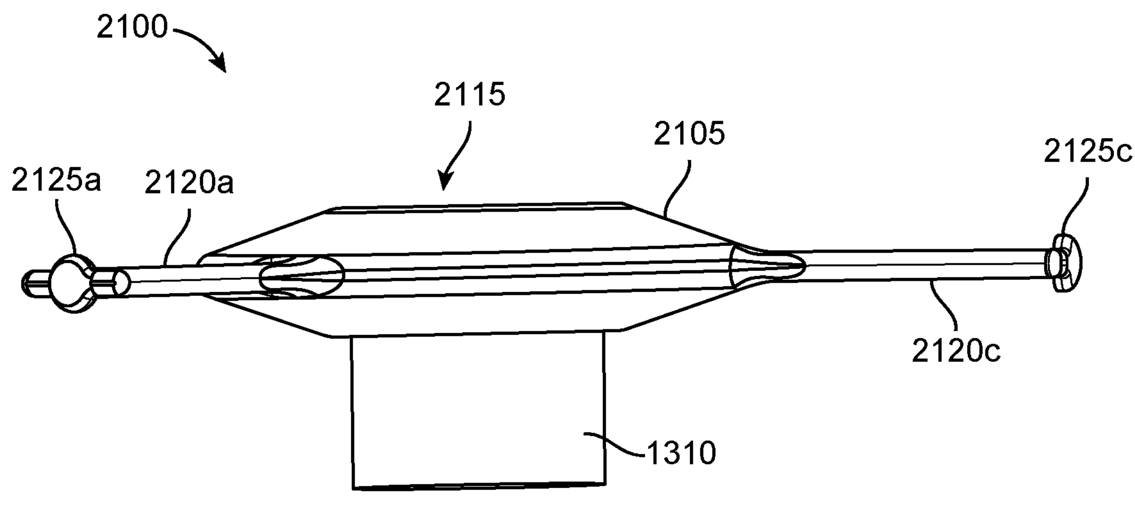
FIG. 11E is a side view of a system formed by an IMT mated with the scleral suspension device of FIG. 11A and after tensioning of the biased arms.

The thickness of the support structure or platform 2105 near the location of the central aperture 2115 can be greater than a thickness of the platform 2105 near its outer periphery (sec, e.g., FIGS. 11C-11D). The central aperture 2115 has a diameter (e.g., 2-6 mm) sized to receive the outer diameter of the IMT and the inner perimeter surface defining the central aperture 2115 has a length that extends along a corresponding length of the outer diameter of the IMT that provides better anterior-to-posterior support. Thus, the inner perimeter surface defining the central aperture 2115 can provide a mating surface against which IMT 1310 engages, which prevents tilt or decentration of the IMT while being supported by the scleral suspension device.

FIG. 11C is a cross-sectional view of the scleral suspension device of FIG. 11A. The cross-sectional shape of the support structure 2105 in FIG. 11C can be substantially three-sided or in the shape of a rounded triangle. A base of the triangle is formed by a surface 2180 of the central aperture 2115, a first side of the triangle is formed by an anterior surface 2182 of the support structure 2105 and a second side of the triangle is formed by a posterior surface 2184 of the support structure 2105. The anterior surface 2182 of the support structure 2105 can be angled posteriorly such that the outer perimeter of the anterior surface 2182 is arranged posterior to the inner perimeter of the anterior surface 2182. The posterior surface 2184 of the support structure 2105 can be angled anteriorly such that the outer perimeter of the posterior surface 2184 is arranged anterior to the inner perimeter of the posterior surface 2184. The anterior surface 2182 and the posterior surface 2182 can meet at a rounded corner 2186 at the perimeter of the support structure 2105. The anterior surface 2182 can meet the surface 2180 of the central aperture 2115 at a second rounded corner 2188 on an anterior end of the central aperture 2115 and the posterior surface 2184 can meet the surface 2180 of the central aperture 2115 at a third rounded corner 2189 on a posterior end of the central aperture 2115. The distance between the anterior end and the posterior end provides a thickness T of the surface 2180 and thus, a thickness of the support structure 2105 at its inner perimeter and the depth of the central aperture 2115. The thickness of the rounded corner 2186 at the perimeter of the support structure 2105 can be less than the thickness T of the surface 2180 to mitigate contact of the device with tissues near the angle, such as the iris, while the greater thickness near the central region at the central aperture 2115 provides sufficient contact and support for the IMT 1310.

FIG. 11D is a cross-sectional view of another implementation of a scleral suspension device. Like the implementation of FIG. 11C, the cross-sectional shape of the support structure 2105 in FIG. 11D can be substantially three-sided or in the shape of a rounded triangle. The first side of the triangle can be formed by the anterior surface 2182 and the second side of the triangle can be formed by the posterior surface 2184. The anterior surface 2182 of the support structure 2105 can be angled posteriorly such that the outer perimeter of the anterior surface 2182 is arranged posterior to the inner perimeter of the anterior surface 2182. The posterior surface 2184 of the support structure 2105 can be angled anteriorly such that the outer perimeter of the posterior surface 2184 is arranged anterior to the inner perimeter of the posterior surface 2184. The anterior surface 2182 and the posterior surface 2182 can meet at the rounded corner 2186 at the outer perimeter of the support structure 2105. The anterior surface 2182 can meet the surface 2180 of the central aperture 2115 at the second rounded corner 2188 on the anterior end of the central aperture 2115 and the posterior surface 2184 can meet the surface 2180 of the central aperture 2115 at the third rounded corner 2189 on the posterior end of the central aperture 2115. The thickness of the rounded corner 2186 at the perimeter of the support structure 2105 can be less than the thickness T of the surface 2180 to mitigate contact of the device with tissues near the angle, such as the iris, while the greater thickness near the central region at the central aperture 2115 provides sufficient contact and support for the IMT 1310. The distance between the anterior end and the posterior end provides an overall thickness T of the surface 2180 and thus, an overall thickness of the support structure 2105 at its inner perimeter and the depth of the central aperture 2115. In the implementation of FIG. 11C, the surface 2180 of the central aperture 2115 can be flat in cross-section so that it forms a uniform annular band configured to contact the outer cylindrical surface of the IMT 1310 along a corresponding surface. In the implementation of FIG. 11D, the surface 2180 of the central aperture 2115 can incorporate a shallow channel 2190. The channel 2190 can aid in fixation of the IMT 1310 to the device 210. As described elsewhere herein, the IMT 1310 can incorporate one or more mating features on its exterior surface. The mating feature(s) can be sized and shaped to project into the channel 2190 to provide a snug fit between the IMT 1310 and the support structure 2105. The channel 2190 in FIG. 11D is shown as having a hemi-spherical concave shape. The mating feature(s) can have a corresponding hemi-spherical convex shape. The cross-sectional shape of the channel 2190 and the mating feature(s) can vary and need not be smooth or spherical.

Figure 10B:
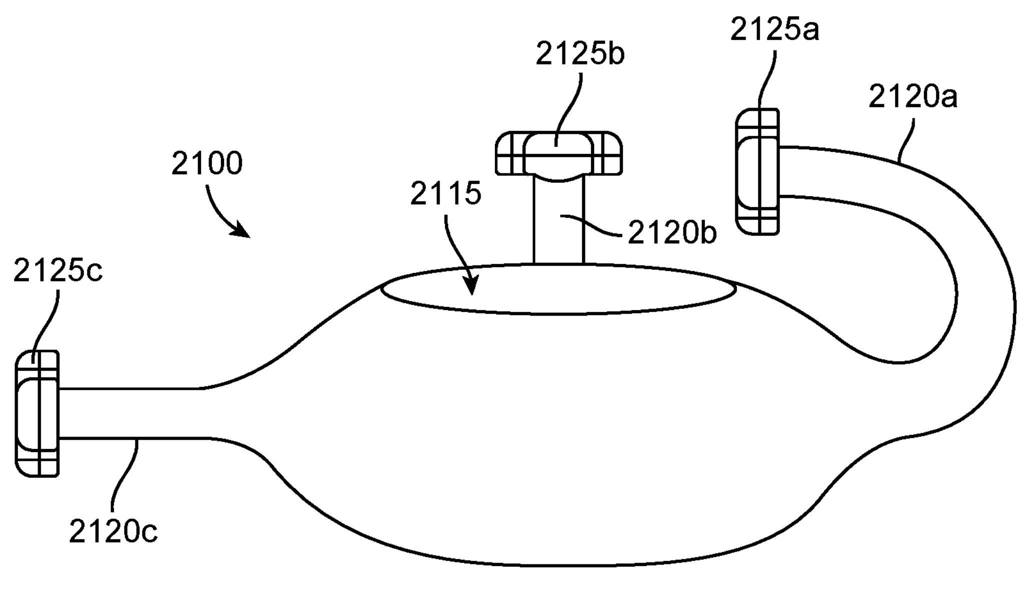
FIG. 10B is a perspective view of a scleral suspension device for mating with the IMT of FIG. 10A.
Figures 10C, 10D:
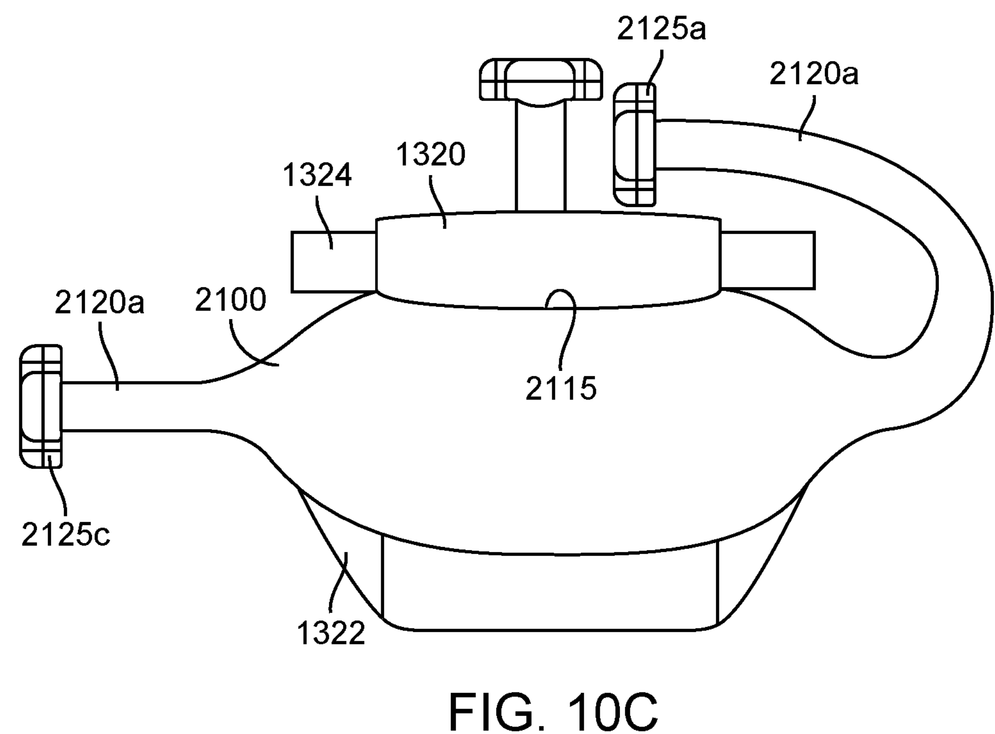
FIG. 10C is a perspective view of a system formed by the IMT of FIG. 10A mated with the scleral suspension device of FIG. 10B.
FIG. 10D is a schematic view of the system of FIG. 10C implanted and sclerally fixated within the eye.
Figure 11F:
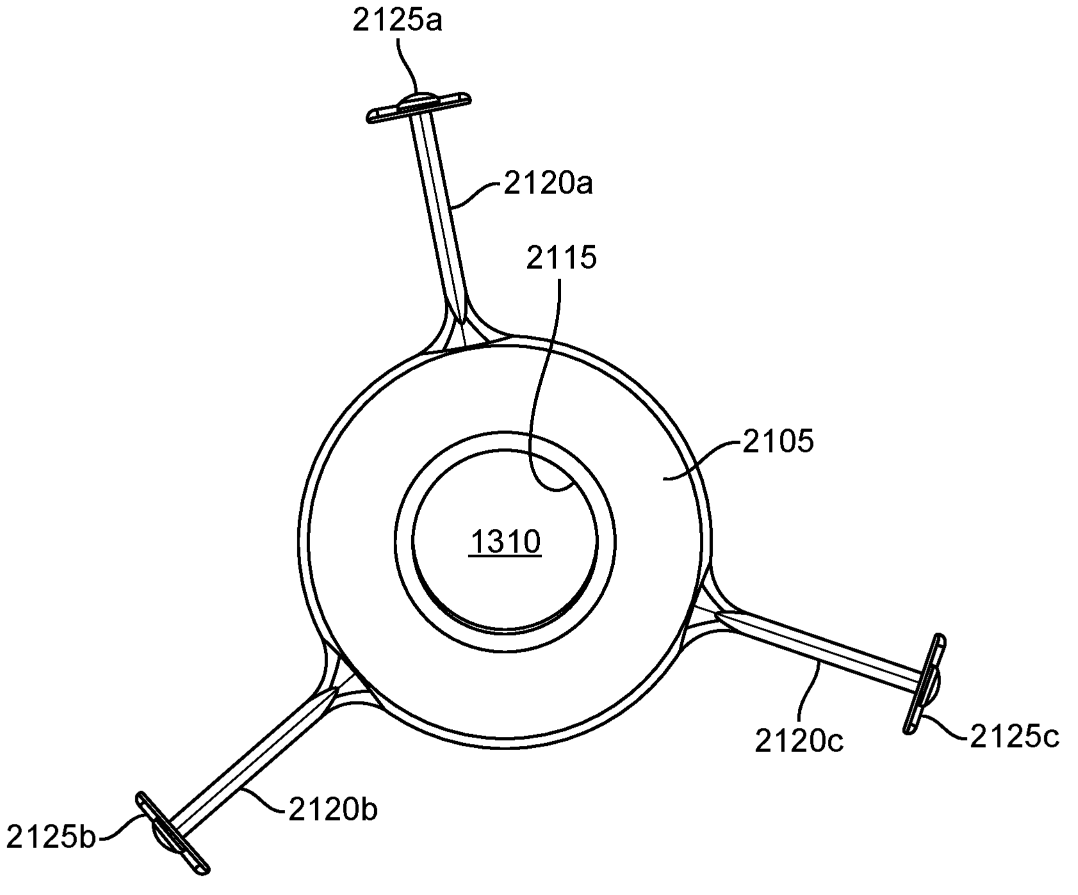
FIG. 11F is an anterior end view of the system of FIG. 11E.
Figures 11G, 11H:
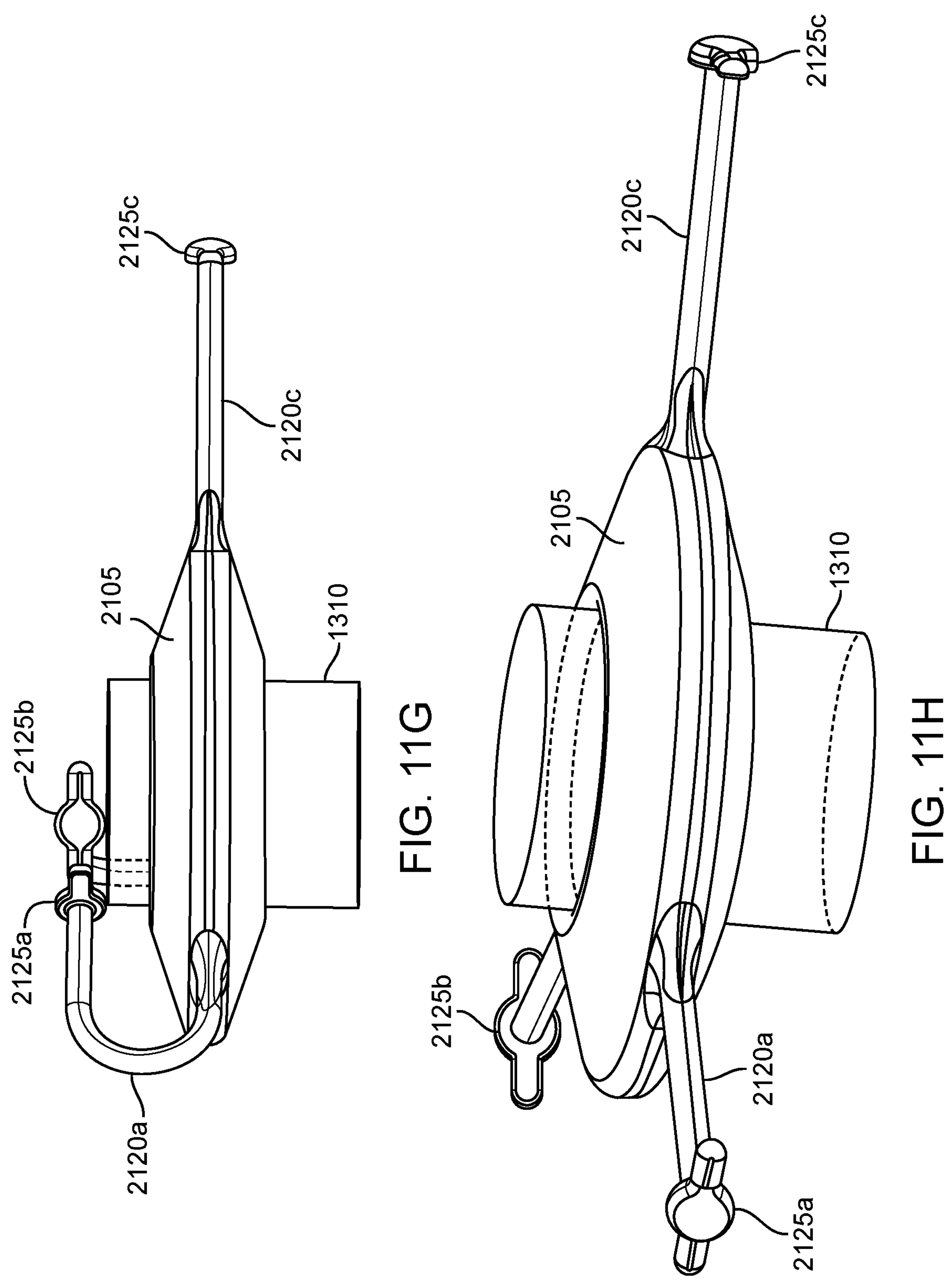
FIG. 11G is a side view of a system formed by an IMT mated with the scleral suspension device of FIG. 11A prior to tensioning of the biased arms.
FIG. 11H is a perspective anterior end view of the system of FIG. 11G after tensioning of the biased arms.
Figures 11I, 11J, 11K:
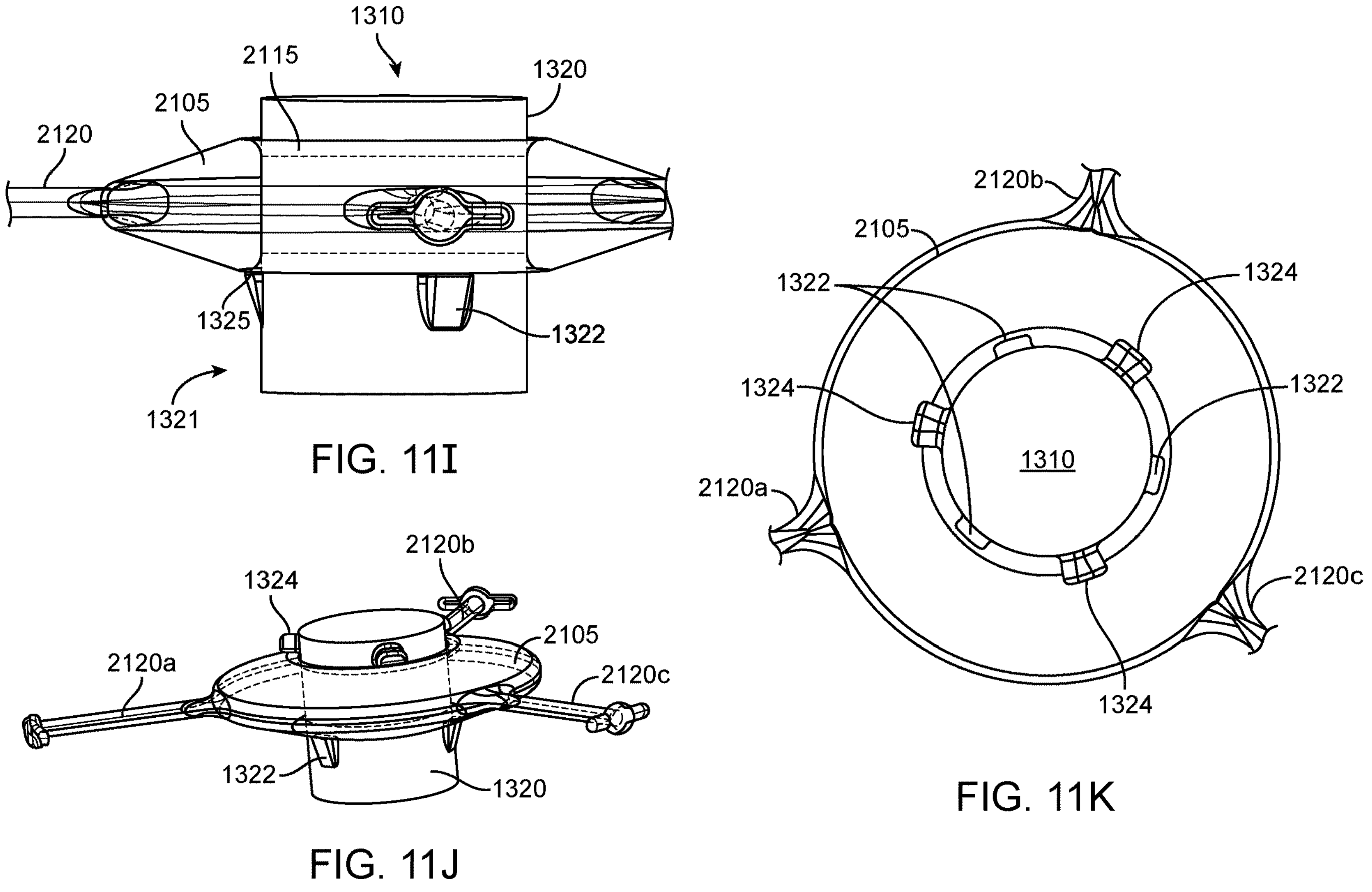
FIG. 11I is a side view of an IMT mated with the scleral suspension device of FIG. 11A, which is shown in transparent view.
FIG. 11J is a perspective anterior end view of the IMT of FIG. 11I mated with the scleral suspension device.
FIG. 11K is an anterior end view of the system of FIG. 11I.

FIG. 10A is a cross-sectional view of the IMT 1310. FIG. 10B is a perspective view of an implementation of the scleral suspension device 2100 configured to mate with the IMT 1310 of FIG. 10A. FIG. 11A is a side view of the scleral suspension device as in FIG. 10B and FIG. 11B is a perspective anterior end view of the scleral suspension device of FIG. 11A. FIG. 10C illustrates the IMT 1310 of FIG. 10A inserted within the central aperture 2115 of the scleral suspension device 2100 showing the anterior stop 1324 positioned anterior to the central aperture 2115 and the posterior mating feature 1322 positioned posterior to the central aperture 2115 of the device 2100. FIG. 11E is a side view of a system formed by an IMT 1310, such as the one of FIG. 10A, mated with the scleral suspension device of FIG. 11A and after tensioning of the biased arms. FIG. 11F is an anterior end view of the system of FIG. 11E. FIG. 11G is a side view of a system formed by an IMT 1310 mated with the scleral suspension device of FIG. 11A prior to tensioning of the biased arms and FIG. 11H is a perspective anterior end view of the system of FIG. 11G after tensioning of the biased arms. FIGS. 10B-10C and FIGS. 11A-11B, 11G-11H show the device 2100 having three fixation arms 2100*a*, 2100*b*, 2100*c* each with corresponding scleral anchors 2125*a*, 2125*b*, 2125*c* as described elsewhere herein. FIG. 10D illustrates the device 2100 mated with the IMT 1310 and anchored within an eye by the fixation arms 2120 with the anchors 2125 located extrasclerally. FIG. 11I is a side view of an IMT mated with the scleral suspension device of FIG. 11A, which is shown in transparent view. FIG. 11J is a perspective anterior end view of the IMT of FIG. 11I mated with the scleral suspension device. FIG. 11K is an anterior end view of the system of FIG. 11I.

Although not reiterated herein regarding FIGS. 10A-10D or FIGS. 11A-11K, the description of the fixation arms above apply to these implementations as well.

The implementation shown in FIGS. 10B-10C and FIGS. 11A-11B show the device 2100 with three fixation arms 2120 where two are biased and one is straight, at rest. The device 2100 can have more than this number of arms 2120 and the arms need not be biased as shown. Regardless the number of arms and whether or not the arms are biased or straight, the arms fixate the device in a trans-scleral manner that involves tensioning as discussed elsewhere herein. Conventional haptics, such as those used in IOLs, often incorporate a curved path of slender loops that, alone with their material properties (e.g., PMMA), provide the haptic with a spring force that is directed in a radially outward direction to engage the device in the eye. The material and the curvature of the haptic along with the radially outward force are intended to center the device and provide fixation. The arms described herein provide a suspension system to the device that allows for tension on the arms to fixation and center the device. The tension of the arms within the plane of the platform provide a superior support system, particularly for heavier implants and for supporting implants in which limited capsular support exists.

The specific design and features of the fixation arms 2120 of the device 2100 can be selected based on the needs of the implant that is being supported by the device 2100. For instance, an IMT such as those described herein are typically much heavier than an artificial iris or intraocular lens or biosensor. Thus, the structural properties of the arms 2120 can be modified to provide sufficient stability to the device being supported. The arms 2120 can be made stronger by adjusting the geometry of the arms, for example, shorter, thicker, wider, or tapered as described elsewhere herein. The arms 2120 can be made stronger by reinforcing a base material with a more rigid plastic, elastomer, or metal material. The arms 2120 can be made effectively stronger by shortening them, thereby reducing the span from the transscleral fixation point to the more robust central housing or platform from which they extend. In some embodiments, the surfaces of the device 2100 that engages the implant are to be minimally deformed by the tensioned scleral fixation arms 2120. This allows for steady engagement with the implant without risk of tilt or flipping anterior-to-posterior. Additionally, the shape of the central aperture 2115 is maintained regardless of the scleral fixation of the arms.

The exact configuration of the chassis of the device can also vary depending on the implant to be positioned in the eye. For example, the chassis for supporting an IOL or an IMT having its own haptic system, may preferably incorporate awnings and recesses for receiving the haptic system. The chassis for supporting an IMT without its own haptic system may not incorporate the awnings and/or recesses and rely instead on a single platform element having a central aperture configured to receive a waist region of the IMT as described elsewhere herein. The chassis can be round or can incorporate a non-round outer perimeter shape (e.g., elongated sides and short ends, triangular, etc.). Similarly, the number of arms may vary from one device to the next depending on the implant to be positioned, including at least 3 arms, 4, 5, 6 or other number.

The IMT 1310 and device 2100 can be co-molded as an integrated implantable device to have a more robust, durable bond and avoid the need for separate insertion of the IMT into the device. The IMT 1310 and device 2100 can also be separate devices configured to be assembled prior to use. The IMT 1310 and device 2100 can be assembled prior to insertion in the eye as a complete implantable system. The IMT 1310 can also be assembled with the device 2100 after insertion of the device 2100 in the eye.

Suitable materials or combinations of materials for the preparation of the various components of the devices disclosed herein are provided throughout. It should be appreciated that other suitable materials are considered. The device can be constructed from any implant grade material that can provide the functions required of the posterior platform, fixation arms, and anchors. Materials that may be employed in this device could be but are not limited to silicone elastomer, fluorosilicone elastomer, polyurethane, hydrophilic or hydrophobic acrylics, polyolefins, nylons, PVDF, PMMA, polyimide, nitinol, titanium, stainless steel, or other implant grade materials. The device may be made from a combination of materials that are geometrically mated together, chemically bonded or welded to one another, overmolded, encapsulated, or other means for joining multiple materials. A given device element may be made of multiple materials. The fixation arms may be constructed from an inelastic or semi-rigid material common to ophthalmic applications such as polypropylene, Nylon, PVDF, polyimide, PMMA, polyurethane, hydrophilic or hydrophobic acrylics, or high durometer silicones. The fixation arms can incorporate or be formed of clastic materials such as acrylics, polyurethanes, silicone elastomers or copolymers thereof that facilitate manipulation of the fixation arm during implantation. In still further implementations, the fixation arm can be formed of a semi-rigid or rigid plastic material such as polypropylene, Nylon, PVDF, polyimide, PMMA, polyurethane, hydrophilic or hydrophobic acrylics, or high durometer silicones embedded or coated with a soft, elastomeric material such as acrylics, polyurethanes, silicone elastomers or copolymers thereof. As discuss elsewhere herein, one or more inorganic pigments or organic dyes can be incorporated into the material of one or more components of the device for visualization purposes to cause the otherwise transparent material to become translucent or opaque. The pigment or dye can vary including white pigments such as titanium dioxide, or pigments of other colors including purple, blue, green, yellow, orange, red, brown, and black.

In various implementations, description is made with reference to the figures. However, certain implementations may be practiced without one or more of these specific details, or in combination with other known methods and configurations. In the description, numerous specific details are set forth, such as specific configurations, dimensions, and processes, to provide a thorough understanding of the implementations. In other instances, well-known processes and manufacturing techniques have not been described in particular detail in order to not unnecessarily obscure the description. Reference throughout this specification to "one embodiment," "an embodiment," "one implementation, "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various placed throughout this specification are not necessarily referring to the same embodiment or implementation. Furthermore, the particular features, structures, configurations, or characteristics may be combined in any suitable manner in one or more implementations.

The devices and systems described herein can incorporate any of a variety of features. Elements or features of one implementation of a device and system described herein can be incorporated alternatively or in combination with elements or features of another implementation of a device and system described herein. For the sake of brevity, explicit descriptions of each of those combinations may be omitted although the various combinations are to be considered herein. Additionally, the devices and systems described herein can be positioned in the eye and need not be implanted specifically as shown in the figures or as described herein. The various devices can be implanted, positioned and adjusted etc. according to a variety of different methods and using a variety of different devices and systems. The various devices can be adjusted before, during as well as any time after implantation. Provided are some representative descriptions of how the various devices may be implanted and positioned, however, for the sake of brevity explicit descriptions of each method with respect to each implant or system may be omitted.

The use of relative terms throughout the description may denote a relative position or direction or orientation and is not intended to be limiting. For example. "distal" may indicate a first direction away from a reference point. Similarly, "proximal" may indicate a location in a second direction opposite to the first direction. Use of the terms "upper," "lower," "top", "bottom," "front," "side," and "back" as well as "anterior," "posterior," "caudal," "cephalad" and the like or used to establish relative frames of reference, and are not intended to limit the use or orientation of any of the devices described herein in the various implementations.

As used herein, the term "about" means a range of values including the specified value, which a person of ordinary skill in the art would consider reasonably similar to the specified value. In aspects, about means within a standard deviation using measurements generally acceptable in the art. In aspects, about means a range extending to +/−10% of the specified value. In aspects, about includes the specified value.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A system comprising:

an implantable miniature telescope (IMT) comprising an outer carrier and an optical element located within the outer carrier; and an implantable scleral suspension device for use with the implantable miniature telescope, the device comprising:

an elastic support structure comprising:

an outer perimeter wall having an outer perimeter surface extending between an anterior surface of the support structure and a posterior surface of the support structure; and a central aperture extending through the support structure between the anterior surface of the support structure and the posterior surface of the support structure, the central aperture defined by an inner perimeter surface of the support structure; and a plurality of fixation arms extending outward from the outer perimeter surface of the support structure, each arm of the plurality of fixation arms is configured for sutureless scleral fixation and to be placed under tension to locate and stabilize the device within an eye, wherein a thickness of the support structure along the inner perimeter surface defining the central aperture is greater than a thickness of the support structure near the outer perimeter surface.

2. The system of claim 1, wherein the thickness of the support structure along the inner perimeter surface defining the central aperture is about 200-2000 microns thick.

3. The system of claim 1, wherein the thickness of the support structure defining the central aperture prevents tilt of the IMT supported by the scleral suspension device.

4. The system of claim 1, wherein the central aperture is sized to receive a carrier of an IMT at least partially therethrough so as to mate the IMT with the support structure.

5. The system of claim 1, wherein the central aperture has a diameter that is about 2 mm to about 6 mm.

6. The system of claim 1, further comprising at least one awning positioned over the anterior surface of the support structure, wherein the at least one awning forms at least one recess anterior to the anterior surface of the support structure, wherein the at least one recess is adapted to receive a portion of the IMT.

7. The system of claim 6, wherein an anterior surface of the IMT projects anterior relative to the awning of the device and a posterior surface of the IMT projects posterior to the device.

8. The system of claim 1, wherein the IMT and the scleral suspension device are separate devices configured to be assembled prior to use.

9. The system of claim 1, wherein the IMT and the scleral suspension device are separate devices configured to be assembled prior to insertion in the eye.

10. The system of claim 1, wherein the IMT and the scleral suspension device are separate devices configured to be assembled after insertion in the eye.

11. The system of claim 1, wherein the IMT further comprises one or more fixation elements configured to mate with at least a region of the scleral suspension device.

12. The system of claim 11, wherein, when mated with the scleral suspension device, a posterior surface of the outer carrier engages the anterior surface of the support structure and the optical element of the miniature telescope optically aligns with the central aperture.

13. The system of claim 1, wherein the optical element of the IMT has a length sized to protrude in one or both anterior and posterior directions relative to the scleral suspension device.

14. The system of claim 1, wherein the outer carrier of the IMT is cylindrical having a circular cross-sectional shape.

15. The system of claim 1, wherein an outer surface of the outer carrier comprises a snap-fit feature configured to mate with the central aperture of the support structure.

16. The system of claim 1, wherein the outer carrier of the IMT incorporates a posterior mating feature and an anterior stop.

17. The system of claim 16, wherein the posterior mating feature is designed to insert through the central aperture in an anterior-to-posterior direction and provide significant resistance to withdrawal from the central aperture from a posterior-to-anterior direction.

18. The system of claim 16, wherein the posterior mating feature is formed by at least two or more distinct mating feature located at multiple points around a circumference of a posterior end region of the outer carrier.

19. The system of claim 16, wherein the anterior stop is formed by at least two or more distinct mating feature located at multiple points around a circumference of an anterior end region of the outer carrier.

20. The system of claim 1, wherein each fixation arm of the plurality of fixation arms is coupled to a trans-scleral anchor for sutureless scleral fixation of the device within the eye.

21. The system of claim 1, wherein the inner perimeter surface defining the central aperture is substantially cylindrical.

* * * * *